(12) United States Patent
Shi et al.

(10) Patent No.: US 11,090,367 B2
(45) Date of Patent: *Aug. 17, 2021

(54) RESTORATION OF TUMOR SUPPRESSION USING MRNA-BASED DELIVERY SYSTEM

(71) Applicants: The Brigham and Women's Hospital, Inc., Boston, MA (US); Children's Medical Center Corporation, Boston, MA (US)

(72) Inventors: Jinjun Shi, Boston, MA (US); Mohammad Ariful Islam, Quincy, MA (US); Yingjie Xu, Newton, MA (US); Omid C. Farokhzad, Waban, MA (US); Bruce Zetter, Wayland, MA (US)

(73) Assignees: The Brigham and Women's Hospital, Inc., Boston, MA (US); Children's Medical Center Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/780,458

(22) Filed: Feb. 3, 2020

(65) Prior Publication Data

US 2020/0261551 A1 Aug. 20, 2020

Related U.S. Application Data

(63) Continuation of application No. 16/348,383, filed as application No. PCT/US2017/060938 on Nov. 9, 2017.

(60) Provisional application No. 62/419,654, filed on Nov. 9, 2016.

(51) Int. Cl.

| *A61K 35/00* | (2006.01) |
| *A61K 38/46* | (2006.01) |
| *A61K 47/59* | (2017.01) |
| *A61P 35/00* | (2006.01) |
| *A61K 9/51* | (2006.01) |

(52) U.S. Cl.
CPC .......... *A61K 38/465* (2013.01); *A61K 9/5146* (2013.01); *A61K 9/5153* (2013.01); *A61K 47/595* (2017.08); *A61P 35/00* (2018.01)

(58) Field of Classification Search
None
See application file for complete search history.

(56) References Cited

U.S. PATENT DOCUMENTS

| 5,543,158 | A | 8/1996 | Gref et al. |
| 5,709,854 | A | 1/1998 | Griffith-Cima et al. |
| 6,129,761 | A | 10/2000 | Hubbell |
| 6,468,798 | B1 | 10/2002 | Debs et al. |
| 6,491,666 | B1 | 12/2002 | Santini, Jr. et al. |
| 6,527,762 | B1 | 3/2003 | Santini, Jr. et al. |
| 6,858,229 | B1 | 2/2005 | Hubbell et al. |
| 6,976,982 | B2 | 12/2005 | Santini, Jr. et al. |
| 7,226,442 | B2 | 6/2007 | Sheppard, Jr. et al. |
| 7,604,628 | B2 | 10/2009 | Santini, Jr. et al. |
| 8,008,449 | B2 | 8/2011 | Korman et al. |
| 8,476,246 | B2 | 7/2013 | Schlingensiepen et al. |
| 8,591,900 | B2 | 11/2013 | Barrett et al. |
| 8,790,655 | B2 | 7/2014 | Carson et al. |
| 8,795,678 | B2 | 8/2014 | Liang et al. |
| 9,073,994 | B2 | 7/2015 | Honjo et al. |
| 9,388,418 | B2 | 7/2016 | Rossi et al. |
| 2003/0165499 | A1 | 9/2003 | Chu et al. |
| 2004/0120948 | A1 | 6/2004 | Mikayama et al. |
| 2006/0002852 | A1 | 1/2006 | Saltzman et al. |
| 2007/0148163 | A1 | 6/2007 | Takahashi et al. |
| 2009/0028910 | A1 | 1/2009 | DeSimone et al. |
| 2011/0271358 | A1 | 11/2011 | Freeman et al. |
| 2013/0011333 | A1 | 1/2013 | Yuan et al. |
| 2013/0011405 | A1 | 1/2013 | Long et al. |
| 2015/0247145 | A1 | 9/2015 | Ozsolak |
| 2016/0206750 | A1 | 7/2016 | Monahan et al. |
| 2016/0243048 | A1 | 8/2016 | Xu et al. |
| 2017/0058033 | A1 | 3/2017 | Lundwig et al. |
| 2018/0296561 | A1* | 10/2018 | Earp, III .......... A61K 39/39541 |

FOREIGN PATENT DOCUMENTS

| WO | WO 2002/088186 | 11/2002 |
| WO | WO 2004/074445 | 9/2004 |
| WO | WO 2007/124299 | 11/2007 |
| WO | WO 2007135195 | 11/2007 |
| WO | WO 2009/114547 | 9/2009 |
| WO | WO 2011/123489 | 10/2011 |
| WO | WO 2012/111762 | 8/2012 |
| WO | WO 2012/149356 | 11/2012 |
| WO | WO 2013/079174 | 6/2013 |
| WO | WO 2013/173223 | 11/2013 |
| WO | WO 2014/070934 | 5/2014 |

(Continued)

OTHER PUBLICATIONS

Tanaka et al. (PTEN gene therapy induces growth inhibition and increases efficacy of chemotherapy in prostate cancer. Cancer Detection and Prevention 29.2 (2005): 170-174).*
Tomioka et al. (Mol Cancer Ther 2008;7(7). Jul. 2008).*
Yamamoto et al. (Current prospects for mRNA gene delivery. Eur. J. Pharm. Biopharm. 71, 484-489 (2009).*
Hadinoto et al. (Lipid-polymer hybrid nanoparticles as a new generation therapeutic delivery platform: a review. European journal of pharmaceutics and biopharmaceutics 85.3 (2013): 427-443), Earp, III (US 20180296561).*
Pilones et al. (Combination of radiotherapy and immune checkpoint inhibitors. Seminars in radiation oncology. vol. 25. No. 1. WB Saunders, 2015).*

(Continued)

*Primary Examiner* — Kimberly Chong
(74) *Attorney, Agent, or Firm* — Fish & Richardson P.C.

(57) ABSTRACT

Compositions and methods for treating cancer that include administering a therapeutically effective amount of a tumor suppressor mRNA complexed with a delivery vehicle as described herein, e.g., a nanoparticle.

17 Claims, 43 Drawing Sheets

(56) References Cited

FOREIGN PATENT DOCUMENTS

| WO | WO 2014/195852 | 12/2014 |
| --- | --- | --- |
| WO | WO 2016/007235 | 1/2016 |
| WO | WO 2016/061142 | 4/2016 |

OTHER PUBLICATIONS

[No Author Listed] "In Situ Cell Death Detection Kit, TMR red; Roche, #12-156-792-910," Roche, Sigma-Aldrich, Mar. 2016, 28 Pages.
Akinc et al., "A combinatorial library of lipid-like materials for delivery of RNAi therapeutics," Nature Biotechnology, May 2008, 26(5):561-9.
Alexandrescu et al., "Immunotherapy for melanoma: current status and perspectives," Journal of immunotherapy (Hagerstown, Md.: 1997), Jul. 2010, 33(6):570, 38 Pages.
Alexis et al., "Factors affecting the clearance and biodistribution of polymeric nanoparticles," Molecular pharmaceutics, Aug. 4, 2008, 5(4):505-15.
Almeida et al., "Temperature and pH stimuli-responsive polymers and their applications in controlled and selfregulated drug delivery," Journal of Applied Pharmaceutical Science, 2012, 2(06):01-10.
Backman et al., "Deletion of Pten in mouse brain causes seizures, ataxia and defects in soma size resembling Lhermitte-Duclos disease," Nature Genetics, Nov. 19, 2001, 29(4):396.
Berezhnoy et al., "A clinically useful approach to enhance immunological memory and antitumor immunity," Oncoimmunology, May 1, 2014, 3(5):e28811.
Bertrand et al., "Cancer nanotechnology: the impact of passive and active targeting in the era of modern cancer biology," Advanced Drug Delivery Reviews, Feb. 1, 2014, 66:2-5, 24 Pages.
Bettinger et al., "Peptide-mediated RNA delivery: a novel approach for enhanced transfection of primary and post-mitotic cells," Nucleic Acids Research, Sep. 15, 2001, 29(18):3882-91.
Campeau et al., "A versatile viral system for expression and depletion of proteins in mammalian cells," PloS one, Aug. 6, 2009, 4(8):e6529, 18 Pages.
Cieslewicz et al., "Targeted delivery of proapoptotic peptides to tumor-associated macrophages improves survival," Proceedings of the National Academy of Sciences, Oct. 1, 2013, 110(40):15919-24.
Coffman et al., "Endothelin receptor-A is required for the recruitment of antitumor T cells and modulates chemotherapy induction of cancer stem cells," Cancer Biology & Therapy. Feb. 1, 2013, 14(2):184-92.
Conde et al., "Self-assembled RNA-triple-helix hydrogel scaffold for microRNA modulation in the tumour microenvironment," Nature Materials, Mar. 2016, 15(3):353-63.
Cox et al., "The hypoxic cancer secretome induces pre-metastatic bone lesions through lysyl oxidase," Nature, Jun. 2015, 522(7554):106-10.
Davis et al., "Evidence of RNAi in humans from systemically administered siRNA via targeted nanoparticles," Nature, Apr. 2010, 464(7291):1067-70.
Di Cristofano et al., "Pten and p27 KIP1 cooperate in prostate cancer tumor suppression in the mouse," Nature Genetics, Feb. 2001, 27(2):222-4.
Dunn et al., "Interferons, immunity and cancer immunoediting," Nature Reviews Immunology, Nov. 2006, 6(11):836-48.
Eggermont et al., "Anti-CTLA-4 antibody adjuvant therapy in melanoma," Seminars in Oncology, Oct. 1, 2010, (37)5:455-59.
Engelman et al., "The evolution of phosphatidylinositol 3-kinases as regulators of growth and metabolism," Nature Reviews Genetics, Aug. 2006, 7(8):606-19.
Escamilla-Tilch et al., "The interplay between pathogen-associated and danger-associated molecular patterns: an inflammatory code in cancer?," Immunology and Cell Biology, Nov. 2013,. 91(10):601-10.

Furnari et al., "Growth suppression of glioma cells by PTEN requires a functional phosphatase catalytic domain," Proceedings of the National Academy of Sciences, Nov. 11, 1997, 94(23):12479-84.
Galluzzi et al., "Trial Watch: Experimental Toll-like receptor agonists for cancer therapy," Oncoimmunology, 2012, 1: 699-716.
Ganesan et al., "Systemic therapy for melanoma," National Medical Journal of India, Jan. 1, 2010, ;23(1):21-7.
Golovina et al., "Regulatory T cells: overcoming suppression of T-cell immunity," The Cancer Journal, Jul. 1, 2010, 16(4):342-7.
Goodrich et al., "The retinoblastoma tumor-suppressor gene, the exception that proves the rule," Oncogene, Aug. 2006, 25(38):5233, 21 Pages.
Grasso et al., "The mutational landscape of lethal castration-resistant prostate cancer," Nature, Jul. 2012, 487(7406):239.
Guo et al., "Interleukin-6 signaling pathway in targeted therapy for cancer," Cancer Treatment Reviews, Nov. 1, 2012, 38(7):904-10.
Guo et al., "Recent advances in nonviral vectors for gene delivery," Accounts of Chemical Research, Aug. 26, 2011, 45(7):971-9.
Guo et al., "Targeting tumor suppressor networks for cancer therapeutics," Current Drug Targets, Jan. 1, 2014, 15(1):2-16.
Hamada et al., "The PTEN/PI3K pathway governs normal vascular development and tumor angiogenesis," Genes & Development, Sep. 1, 2005, 19(17):2054-65.
Han et al., "Fluorescence in situ hybridization study shows association of PTEN deletion with ERG rearrangement during prostate cancer progression," Modern Pathology, Aug. 2009, 22(8):1083, 17 Pages.
Hopkins et al., "A secreted PTEN phosphatase that enters cells to alter signaling and survival," Science, Jul. 26, 2013, 341(6144):399-402.
Huang et al., "PTEN induces chemosensitivity in PTEN-mutated prostate cancer cells by suppression of Bcl-2 expression," Journal of Biological Chemistry, Oct. 19, 2001, 276(42):38830-6.
Islam et al., "Accelerated gene transfer through a polysorbitol-based transporter mechanism," Biomaterials, Dec. 1, 2011, 32(36):9908-24.
Islam et al., "Biomaterials for mRNA delivery," Biomaterials Science, 2015, 3(12):1519-33.
Islam et al., "The role of osmotic polysorbitol-based transporter in RNAi silencing via caveolae-mediated endocytosis and COX-2 expression," Biomaterials, Dec. 1, 2012, 33(34):8868-80.
James et al., "Smart polymers for the controlled delivery of drugs—a concise overview," Acta Pharmaceutica Sinica B., Apr. 1, 2014, 4(2):120-7.
Jeong et al., "Lessons from nature: stimuli-responsive polymers and their biomedical applications," Trends in Biotechnology, Jul. 1, 2002, 20(7):305-11.
Jiang et al., "PI3K/PTEN signaling in angiogenesis and tumorigenesis," Advances in Cancer Research, Jan. 1, 2009, 102:19-65.
Juric et al., "Convergent loss of PTEN leads to clinical resistance to a PI (3) Kα inhibitor," Nature, Feb. 2015, 518(7538):240-4.
Kauffman et al., "Optimization of lipid nanoparticle formulations for mRNA delivery in vivo with fractional factorial and definitive screening designs," Nano Letters, Oct. 20, 2015, 15(11):7300-6.
Kim et al., "Resorbable polymer microchips releasing BCNU inhibit tumor growth in the rat 9L flank model," Journal of Controlled Release, Nov. 6, 2007, 123(2):172-8.
Klinke, "A multiscale systems perspective on cancer, immunotherapy, and Interleukin-12," Molecular Cancer, Dec. 2010, 9(1):242.
Knop K et al., "Poly (ethylene glycol) in drug delivery: pros and cons as well as potential alternatives," Angewandte Chemie International Edition, Aug. 23, 2010,49(36):6288-308.
Kong et al., "Hyperthermia enables tumor-specific nanoparticle delivery: effect of particle size," Cancer Research, Aug. 15, 2000, 60(16):4440-5.
Kormann et al., "Expression of therapeutic proteins after delivery of chemically modified mRNA in mice," Nature Biotechnology, Feb. 2011, 29(2):154.
Krüger et al., "Immune based therapies in cancer," Histol Histopathol, Jun. 2007, 22(6):687-96.
Krzywinski et al., "Points of significance: Nonparametric Tests," Nature Methods, May 2014, 11(5):467-468.

(56) References Cited

OTHER PUBLICATIONS

Lee et al., "Cytokines in cancer immunotherapy," Cancers, Dec. 2011, 3(4):3856-93.
Lee et al., "Programming human dendritic cells with mRNA," Synthetic Messenger RNA and Cell. Metabolism Modulation, Haman Press, 2013, 111-25.
Leonhardt et al., "Single-cell mRNA transfection studies: delivery, kinetics and statistics by numbers," Nanomedicine: Nanotechnology, Biology and Medicine, May 1, 2014, 10(4):679-88.
Li et al., "An orthogonal array optimization of lipid-like nanoparticles for mRNA delivery in vivo," Nano Letters, Nov. 6, 2015, 15(12):8099-107.
Li et al., "PTEN, a putative protein tyrosine phosphatase gene mutated in human brain, breast, and prostate cancer," Science, Mar. 28, 1997, 275(5308):1943-7.
Ligon et al., "Multi-level kinetic model of mRNA delivery via transfection of lipoplexes," PloS one, Sep. 19, 2014, 9(9):e107148.
Liliental et al., "Genetic deletion of the Pten tumor suppressor gene promotes cell motility by activation of Rac1 and Cdc42 GTPases," Current Biology, Apr. 1, 2000, 10(7):401-4.
Liu et al., "Structure-based programming of lymph-node targeting in molecular vaccines," Nature, Mar. 2014, 507(7493):519.
Llorente et al., "Clinical and biologic effects of anti-interleukin-10 monoclonal antibody administration in systemic lupus erythematosus," Arthritis & Rheumatism: Official Journal of the American College of Rheumatology, Aug. 2000, 43(8):1790-800.
Lotan et al, "PTEN protein loss by immunostaining analytic validation and prognostic indicator for a high risk surgical cohort of prostate cancer patients," Clinical Cancer Research, Oct. 15, 2011, 17(20):6563-73.
Lu et al., "Polysaccharide krestin is a novel TLR2 agonist that mediates inhibition of tumor growth via stimulation of CD8 T cells and NK cells," Clinical Cancer Research, Jan. 1, 2011, 17(1):67-76.
Luo et al., "Targeting tumor-associated macrophages as a novel strategy against breast cancer," The Journal of Clinical Investigation, Aug. 1, 2006, 116(8):2132-41.
Luo et al., "Dual-functional lipid-like nanoparticles for delivery of mRNA and MRI contrast agents," Nanoscale, Jan. 26, 2017, 9(4):1575-9.
MacEwan et al., "Stimulus-responsive macromolecules and nanoparticles for cancer drug delivery," Nanomedicine, Jul. 2010, 5(5):793-806.
Maehama et al., "The tumor suppressor, PTEN/MMAC1, dephosphorylates the lipid second messenger, phosphatidylinositol 3, 4, 5-trisphosphate," Journal of Biological Chemistry, May 29, 1998, 273(22):13375-8.
Masson et al., "The intrinsically disordered tails of PTEN and PTEN-L have distinct roles in regulating substrate specificity and membrane activity," Biochemical Journal, Jan. 15, 2016, 473 (2):135-44.
McGillicuddy et al., "Proteasomal and genetic inactivation of the NF1 tumor suppressor in gliomagenesis," Cancer Cell, Jul. 7, 2009, 16(1):44-54.
Melero et al., "IL-12 gene therapy for cancer: in synergy with other immunotherapies," Trends in Immunology, Mar. 1, 2001, 22(3):113-5.
Mineharu et al., "Blockade of mTOR signaling via rapamycin combined with immunotherapy augments antiglioma cytotoxic and memory T-cell functions," Molecular Cancer Therapeutics. Dec. 1, 2014, 13(12):3024-36.
Moschella et al., "Combination strategies for enhancing the efficacy of immunotherapy in cancer patients," Annals of the New York Academy of Sciences, May 1, 2010, 1194(1):169-78.
Munn, "Blocking IDO activity to enhance anti-tumor immunity," Front Biosci (Elite Ed), Jan. 1, 2012, 4:734-45.
NCBI Accession No. NP_001241.1, "tumor necrosis factor receptor superfamily member 5 isoform 1 precursor [Homo sapiens]," Oct. 11, 2019, 4 Pages.

NCBI Accession No. NP_001254635.1, "programmed cell death 1 ligand 1 isoform b precursor [Homo sapiens]," Oct. 14, 2019, 3 Pages.
NCBI Accession No. NP_001289682.1, "tumor necrosis factor receptor superfamily member 5 isoform 3 precursor [Homo sapiens]," Oct. 11, 2019, 3 Pages.
NCBI Accession No. NP_001300958.1, "programmed cell death 1 ligand 1 isoform c precursor [Homo sapiens]," Oct. 14, 2019, 3 Pages.
NCBI Accession No. NP_001309350.1, "tumor necrosis factor receptor superfamily member 5 isoform 4 precursor [Homo sapiens]," Oct. 10, 2019, 4 Pages.
NCBI Accession No. NP_001309351.1, "tumor necrosis factor receptor superfamily member 5 isoform 5 precursor [Homo sapiens]," Oct. 10, 2019, 3 Pages.
NCBI Accession No. NP_005009.2, "programmed cell death protein 1 precursor [Homo sapiens]," Oct. 24, 2019, 4 Pages.
NCBI Accession No. NP_054862.1, "programmed cell death 1 ligand 1 isoform a precursor [Homo sapiens]," Oct. 14, 2019, 3 Pages.
NCBI Accession No. NP_690593.1, "tumor necrosis factor receptor superfamily member 5 isoform 2 precursor [Homo sapiens]," Oct. 10, 2019, 3 Pages.
Needleman et al., "A general method applicable to the search for similarities in the amino acid sequence of two proteins," Journal of Molecular Biology, Mar. 28, 1970, 48(3):443-53.
Newton et al., Anti-interleukin-10 R 1 monoclonal antibody in combination with bacillus Calmette-Guérin is protective against bladder cancer metastasis in a murine orthotopic tumour model and demonstrates systemic specific anti-tumour immunity, Clinical & Experimental Immunology, Jul. 2014, 177(1):261-8.
PCT International Preliminary Report on Patentability in International Appln. PCT/US2017/060938, dated May 23, 2019, 10 pages.
PCT International Search Report and Written Opinion in International Application No. PCT/US2017/060938, dated Mar. 8, 2018, 17 pages.
Pearce et al., "Enhancing CD8 T-cell memory by modulating fatty acid metabolism," Nature, Jul. 2009, 460(7251):103.
Portielje et al., "IL-12: a promising adjuvant for cancer vaccination," Cancer Immunology, Immunotherapy, Mar. 1, 2003, 52(3):133-44.
Pradeu et al., "The danger theory: 20 years later," Frontiers in Immunology, Sep. 17, 2012, 3:287.
Quabius et al., "Synthetic mRNAs for manipulating cellular phenotypes: an overview," New Biotechnology, Jan. 25, 2015, 32(1):229-35.
Radtke et al., "The role of Notch in tumorigenesis: oncogene or tumour suppressor?," Nature Reviews Cancer, Oct. 2003, 3(10):756.
Ramaswamy et al., "Regulation of G1 progression by the PTEN tumor suppressor protein is linked to inhibition of the phosphatidylinositol 3-kinase/Akt pathway," Proceedings of the National Academy of Sciences, Mar. 2, 1999, 96(5):2110-5.
Read et al., "A versatile reducible polycation-based system for efficient delivery of a broad range of nucleic acids," Nucleic Acids Research, Jan. 1, 2005, 33(9):e86-.
Rejman et al., "mRNA transfection of cervical carcinoma and mesenchymal stem cells mediated by cationic carriers," Journal of Controlled Release, Nov. 1, 2010, 147(3):385-91.
Ricci et al., "Sustained release of lidocaine from Poloxamer 407 gels," International Journal of Pharmaceutics, Jan. 20, 2005, 288(2):235-44.
Schmitz et al., "Complete loss of PTEN expression as a possible early prognostic marker for prostate cancer metastasis," International Journal of Cancer, Mar. 15, 2007, 120(6):1284-92.
Schultheis et al., "First-in-human phase I study of the liposomal RNA interference therapeutic Atu027 in patients with advanced solid tumors," Journal of Clinical Oncology, Nov. 17, 2014, 32(36):4141, 11 Pages.
Seton-Rogers, "Tumour suppressors: Different roads to inactivation," Nature Reviews Cancer, Aug. 13, 2009, 9(9):610.
Shi et al., "Cancer nanomedicine: progress, challenges and opportunities," Nature Reviews Cancer, Jan. 2017, 17(1):20, 18 Pages.

(56) References Cited

OTHER PUBLICATIONS

Shiao et al., "Immune microenvironments in solid tumors: new targets for therapy," Genes & development, Dec. 15, 2011, 25(24):2559-72.
Sircar et al., "PTEN genomic deletion is associated with p-Akt and AR signalling in poorer outcome, hormone refractory prostate cancer," The Journal of Pathology: A Journal of the Pathological Society of Great Britain and Ireland, Aug. 2009, 218(4):505-13.
Smukste et al., "Restoring functions of tumor suppressors with small molecules," Cancer Cell, Dec. 1, 2003, 4(6):419-20.
Miller et al., "Non-viral CRISPR/Cas gene editing in vitro and in vivo enabled by synthetic nanoparticle co-delivery of Cas9 mRNA and sgRNA. Angewandte Chemie International Edition," Jan. 19, 2017, 56(4):1059-63.
Moffett et al., "Hit-and-run programming of therapeutic cytoreagents using mRNA nanocarriers," Nature Communications, Aug. 30, 2017, 8(1):389, 13 pages.
Moses et al., "Activating PTEN tumor suppressor expression with the CRISPR/dCas9 system," Molecular Therapy-Nucleic Acids, Mar. 1, 2019, 14:287-300.
Nagata et al., "PTEN activation contributes to tumor inhibition by trastuzumab, and loss of PTEN predicts trastuzumab resistance in patients," Cancer Cell, Aug. 1, 2004, 6(2):117-27.
Nam et al., "Cancer nanomedicine for combination cancer immunotherapy," Nature Reviews Materials, Jun. 2019, 4(6):398-414.
Peng et al., "Loss of PTEN promotes resistance to T cell-mediated immunotherapy," Cancer Discovery, Feb. 1, 2016, 6(2):202-16.
Postow et al., "Immune-related adverse events associated with immune checkpoint blockade," New England Journal of Medicine, Jan. 11, 2018, 378(2):158-68.
Reinhard et al., "An RNA vaccine drives expansion and efficacy of claudin-CAR-T cells against solid tumors," Science, Jan. 24, 2020, 367(6476):446-53.
Ribas et al., "Cancer immunotherapy using checkpoint blockade," Science, Mar. 23, 2018, 359(6382):1350-5.
Schlake et al., "mRNA as novel technology for passive immunotherapy," Cellular and Molecular Life Sciences, Jan. 30, 2019, 76(2):301-28.
Sharabi et al., "Radiation and checkpoint blockade immunotherapy: radiosensitisation and potential mechanisms of synergy," The Lancet Oncology, Oct. 1, 2015, 16(13):e498-509.
Sharma et al., "Primary, adaptive, and acquired resistance to cancer immunotherapy," Cell, Feb. 9, 2017, 168(4):707-23.
Shi et al., "Hybrid lipid-polymer nanoparticles for sustained siRNA delivery and gene silencing," Nanomedicine: Nanotechnology, Biology and Medicine, Jul. 1, 2014, 10(5):e897-900.
Su et al., "Therapeutic antitumor efficacy of tumor-derived autophagosome (DRibble) vaccine on head and neck cancer," International Journal of Nanomedicine, Mar. 10, 2015, 10:1921, 10 pages.
Trepotec et al., "Delivery of mRNA therapeutics for the treatment of hepatic diseases," Molecular Therapy, Apr. 10, 2019, 27(4):794-802.
Viry et al., "Autophagy: an adaptive metabolic response to stress shaping the antitumor immunity," Biochemical Pharmacology, Nov. 1, 2014, 92(1):31-42.
Wang et al., "Autophagy-dependent ATP release from dying cells via lysosomal exocytosis," Autophagy, Oct. 25, 2013, 9(10):1624-5.
Wang et al., "Self-Assembled Autophagy-Inducing Polymeric Nanoparticles for Breast Cancer Interference In-Vivo," Advanced Materials, Apr. 2015, 27(16):2627-34.
Xiong et al., "Biomedical applications of mRNA nanomedicine. Nano research," Oct. 1, 2018, 11(10):5281-309.
Xu et al., "Enhancing tumor cell response to chemotherapy through nanoparticle-mediated codelivery of siRNA and cisplatin prodrug," Proceedings of the National Academy of Sciences, Nov. 12, 2013, 110(46):18638-43.
Xu et al, "Tumor suppressor TET2 promotes cancer immunity and immunotherapy efficacy," The Journal of Clinical Investigation, Sep. 4, 2019, 129(10), 17 pages.
Yang et al., "Tumour YAP1 and PTEN expression correlates with tumour-associated myeloid suppressor cell expansion and reduced survival in colorectal cancer," Immunology, Oct. 2018, 155(2):263-72.
Zabirnyk et al., "Nanoparticles as a novel class of autophagy activators," Autophagy, May 10, 2007, 3(3):278-81.
Zhong et al., "Autophagy, inflammation, and immunity: a troika governing cancer and its treatment," Cell, Jul. 14, 2016, 166(2):288-98.
Zitvogel et al., "The anticancer immune response: indispensable for therapeutic success?," The Journal of Clinical Investigation, Jun. 2, 2008, 118(6):1991-2001.
Zunino et al., "Hyperthermic intraperitoneal chemotherapy leads to an anticancer immune response via exposure of cell surface heat shock protein 90," Oncogene, Jan. 2016, 35(2):261-8.

\* cited by examiner

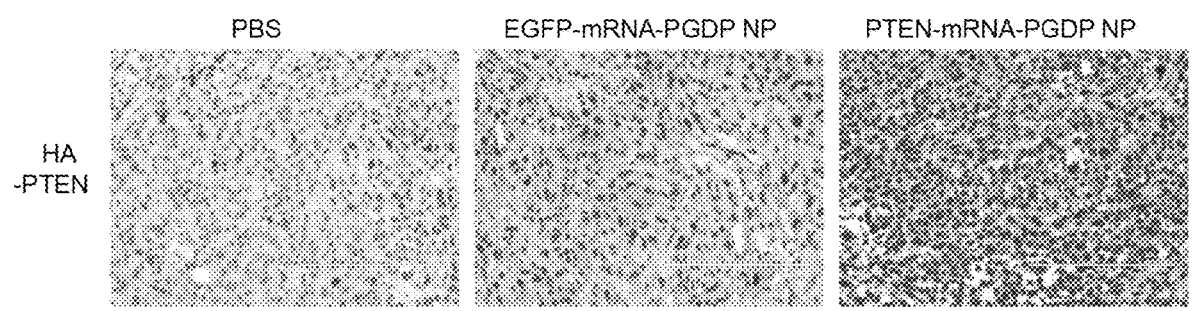
FIG. 5E
FIG. 6A
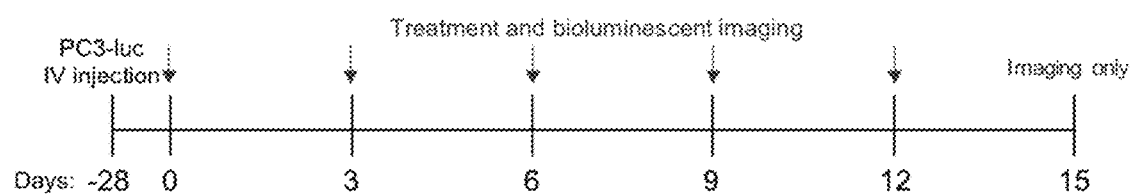
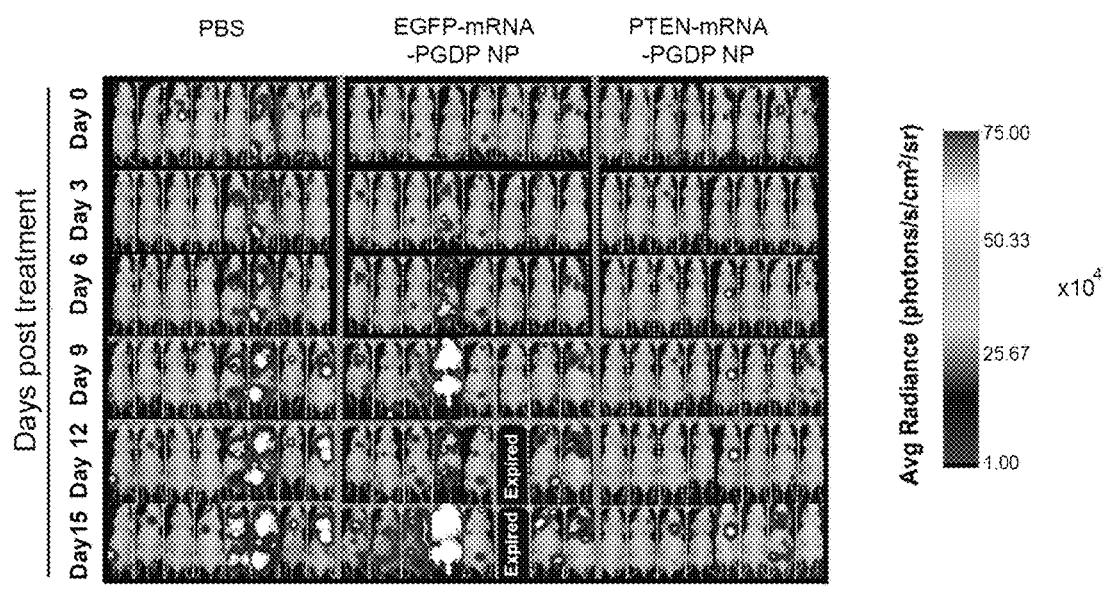
FIG. 6B

Day 28

Day 43

FIG. 9A
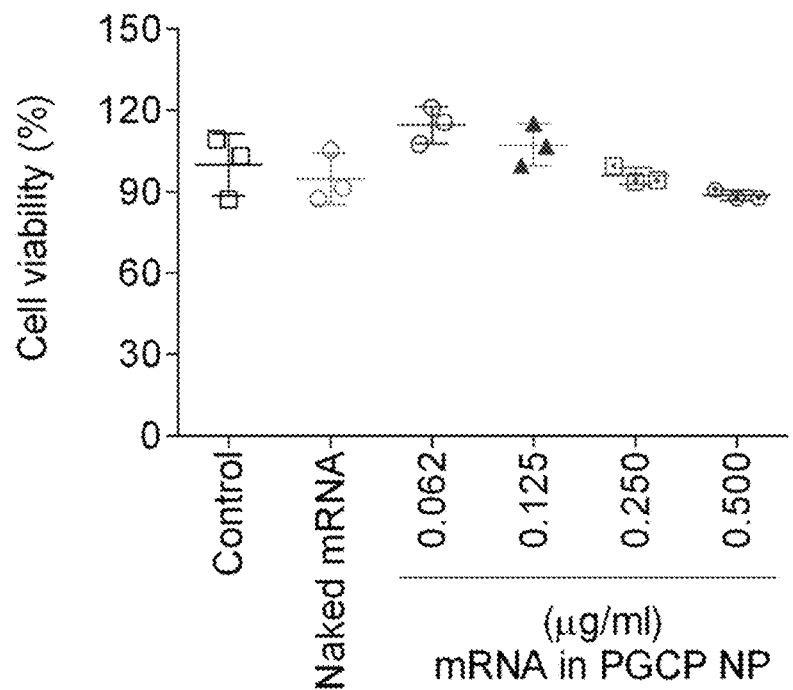
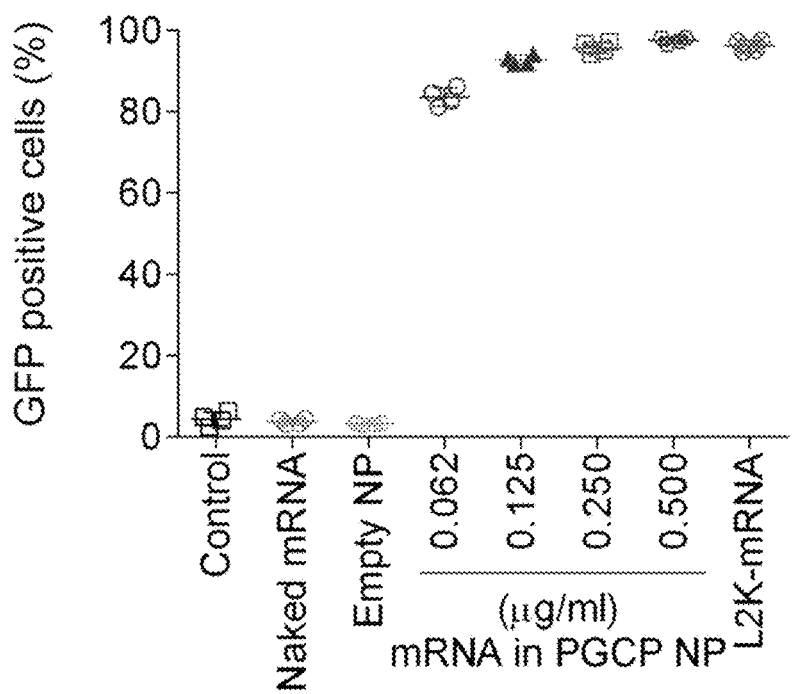
FIG. 9B

LNCaP

Control

L2K PTEN mRNA

Empty PGCP NP

PTEN-mRNA-PGCP NP

FIG. 18A
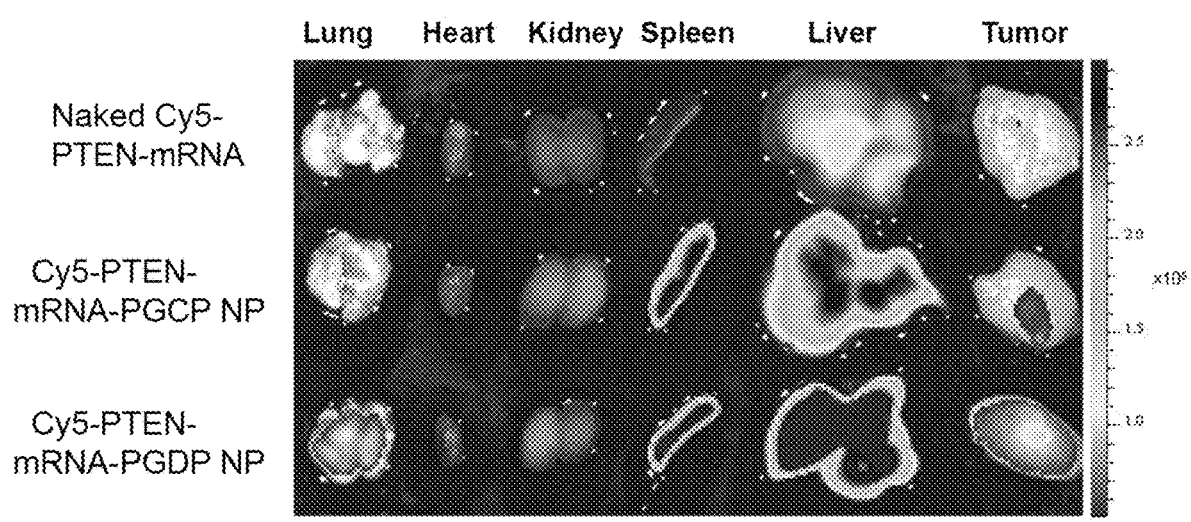
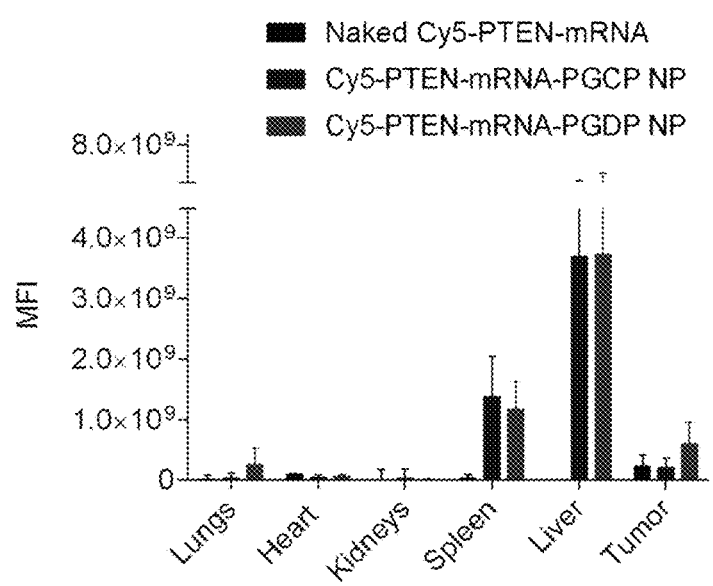
FIG. 18B

RESTORATION OF TUMOR SUPPRESSION USING MRNA-BASED DELIVERY SYSTEM

CLAIM OF PRIORITY

This application is a continuation of U.S. patent application Ser. No. 16/348,383, filed May 8, 2019, which is a § 371 National Stage Application of PCT/US2017/060938, filed Nov. 9, 2017, which claims the benefit of U.S. Provisional Application Ser. No. 62/419,654, filed on Nov. 9, 2016. The entire contents of the foregoing are incorporated herein by reference.

FEDERALLY SPONSORED RESEARCH OR DEVELOPMENT

This invention was made with Government support under Grant Nos. HL127464 and CA200900 awarded by the National Institutes of Health. The Government has certain rights in the invention.

TECHNICAL FIELD

Described herein are compositions and methods for treating cancer that include administering a tumor suppressor mRNA complexed with a delivery vehicle as described herein, e.g., a nanoparticle.

BACKGROUND

The loss or mutation of tumor suppressors contributes to the development and progression of tumors. Stable restoration of tumor suppression has been difficult to achieve.

SUMMARY

Loss and/or mutation of tumor-suppressor genes is a dominant force in tumor development and clinical resistance to a variety of therapies; see, e.g., McGillicuddy et al., Cancer Cell. 2009 Jul. 7; 16(1):44-54; Radtke and Raj, Nat Rev Cancer. 2003 October; 3(10):756-67; Goodrich, Oncogene. 2006 Aug. 28; 25(38):5233-43; Seton-Rogers, Nat Rev Cancer. 2009 September; 9(9):610; Juric et al., Nature. 2015 Feb. 12; 518(7538):240-4; and Peng et al., Cancer Discov. 2016 February; 6(2):202-16. A wide range of tumor suppressors (Table 1) has been identified, along with their association with different types of cancers. For example, phosphatase and tensin homolog on chromosome ten (PTEN) is among the best-characterized tumor suppressors. PTEN mutations have been reported in a variety of human cancers[1], including prostate cancer (PCa). Loss of one PTEN allele is seen in the majority of localized PCa, and homozygous deletion of PTEN is more common in metastatic castration-resistant PCa (mCRPC) (~50%) than in androgen-dependent primary tumors (~10%)[2-8]. Moreover, loss of PTEN protein expression is more frequent than genomic PTEN loss and has been correlated with high Gleason score and faster progression to metastasis[9]. PTEN encodes a dual phosphatase that acts on both lipid and protein substrates. By catalyzing phosphatidylinositol (3,4,5)-trisphosphate (PIP3) dephosphorylation, PTEN negatively regulates the phosphatidylinositol 3-kinase (PI3K)-AKT pathway[10-14], a key signaling mediator of most receptor tyrosine kinases (RTKs)[15]. Recent integrative genomic profiling and whole-exosome sequencing analysis highlight the frequency of alterations of the PI3K-AKT pathway in PCa and are associated with both primary (42%) and metastatic disease (~100%)[16, 17]. Since activation of the PI3K-AKT pathway upon PTEN loss enhances tumor cell survival, proliferation[12, 18], migration[19, 20], angiogenesis[21, 22], and anti-apoptosis[10], blocking this pathway has been proposed to inhibit tumor growth and sensitize tumor cells to apoptosis.

Reversal of the phenotype induced by loss of tumor suppressors has long proven an elusive goal. Two major strategies have been employed for suppressor restoration: restoring a functional copy of a given tumor-suppressor gene via transfection; and the use of small-molecule agents to reactivate tumor-suppressor function via conformational change in the mutated molecule. The latter approach has met with little success and is destined to be ineffective when the suppressor gene has been deleted. For instance, while pharmacological inhibitors of the AKT-mTOR pathway are in clinical development, they cannot compensate fully for the loss of PTEN function, and show a poor toxicity profile. The major limitations of restoring suppressor gene in tumors include inefficient delivery to targeted tumor cells, poor transfection efficacy, insufficient expression, and possible insertional mutagenesis. Consequently, restoring tumor-suppressor activity in cancer cells is highly challenging and requires the design of a functionally improved tumor suppressor with unique therapeutic modality that can withstand the rigors of systemic delivery, especially in the metastatic setting where the tumor burden is widely distributed.

Recently, chemically modified mRNA has emerged as an intriguing alternative to DNA-based gene therapy, as its intrinsic qualities facilitate its ease of use as a genetic material that is independent of nuclear localization and genomic integration for transfection activity[23, 24]. mRNA also provides rapid protein expression even in non-dividing and hard-to-transfect cells (e.g., immune cells), as well as cancer cells. Moreover, mRNA offers more consistent and predictable protein expression kinetics than DNA, whose expression kinetics show random onset[25-28]. However, delivery of mRNA presents several potential challenges, including large size, highly negative charge, susceptibility to degradation, and suboptimal protein translation capacity if it is not effectively modified and delivered into cells[29]. Thus, safe and effective in vivo cytosolic delivery of mRNA to tumor tissues while retaining integrity and functional activity remains elusive.

It is therefore an object of the present invention to provide nanotechnologies which can be used to deliver a therapeutic tumor suppressor mRNA or combinations of different tumor suppressor mRNAs for cancer treatment.

A number of nano-engineered formulations (e.g., polymer-based NPs[30, 31], lipid-based NPs[32-35], and lipidoid NPs[36, 37]) have designed for in vivo delivery of RNAs including siRNA or other small oligonucleotides, and have shown promising results in laboratory or clinical settings[38-41]. The present methods and compositions are exemplified by the use of a lipid-polymer hybrid NP platform for systemic delivery of modified PTEN mRNA to PCa tumors. This system successfully restored functional PTEN protein production, with consequent inhibition of tumor cell growth and induction of apoptosis both in vitro and in vivo. As described herein, tumor suppressor mRNA delivery can be used for the treatment of cancers with a tumor suppressor deficiency, e.g., hybrid NP-mediated delivery of PTEN mRNA in a cancer with a PTEN deficiency.

Thus, provided herein are compositions comprising one or more tumor suppressor-encoding mRNAs complexed with a delivery vehicle.

In some embodiments, the delivery vehicle is selected from the group consisting of protamine complexes, lipid nanoparticles, polymeric nanoparticles, lipid-polymer hybrid nanoparticles, and inorganic nanoparticles, or combinations thereof.

In some embodiments, the delivery vehicle is a lipid-polymer nanoparticle. In some embodiments, the core of the nanoparticle comprises a lipid, a water-insoluble polymer, and the tumor suppressor-encoding mRNAs are complexed with the lipid. In some embodiments, the lipid comprises cationic lipid-like compound G0-C14. In some embodiments, the water-insoluble polymer comprises PLGA.

In some embodiments, the tumor suppressor-encoding mRNAs encodes Phosphatase and tensin homolog on chromosome ten (PTEN).

In some embodiments, the tumor suppressor-encoding mRNAs encode one or more proteins listed in Table 1.

In some embodiments, the tumor suppressor-encoding mRNAs comprise one or more modifications, preferably selected from the group consisting of ARCA capping; enzymatic polyadenylation to add a tail of 100-250 adenosine residues; and substitution of one or both of cytidine with 5-methylcytidine and/or uridine with pseudouridine.

Also provided herein are methods for treating a subject who has cancer. The methods include administering to the subject a therapeutically effective amount of a composition described herein.

Further provided herein are methods for treating a subject who has cancer. The methods include administering to the subject a therapeutically effective amount of a composition comprising mRNA encoding Phosphatase and tensin homolog on chromosome ten (PTEN) protein, wherein the mRNAs are complexed with a delivery vehicle, to a subject in need thereof. In some embodiments, the subject has a cancer associated with loss of PTEN expression or activity. In some embodiments, the subject has prostate cancer, breast cancer, or glioblastoma.

In some embodiments, wherein the delivery vehicle is selected from the group consisting of protamine complexes, lipid nanoparticles, polymeric nanoparticles, lipid-polymer hybrid nanoparticles, and gold nanoparticles.

In some embodiments, the nanoparticle is a lipid-polymer nanoparticle.

In some embodiments, the core of the nanoparticle comprises a lipid, a water-insoluble polymer, and the tumor suppressor-encoding mRNAs are complexed with the lipid. In some embodiments, the lipid comprises cationic lipid-like compound G0-C14. In some embodiments, the water-insoluble polymer comprises PLGA.

In some embodiments, the tumor suppressor-encoding mRNAs comprise one or more modifications, preferably selected from the group consisting of ARCA capping; enzymatic polyadenylation to add a tail of 100-250 adenosine residues; and substitution of one or both of cytidine with 5-methylcytidine and/or uridine with pseudouridine.

Also provided are the compositions as described herein for use in treating a subject who has cancer, e.g., a cancer associated with loss of expression or activity of the tumor suppressor. In some embodiments, the tumor suppressor-encoding mRNAs comprise mRNAs encoding Phosphatase and tensin homolog on chromosome ten (PTEN) protein, and the subject has a cancer associated with loss of expression or activity of PTEN.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control. Other features and advantages of the invention will be apparent from the following detailed description and figures, and from the claims.

DESCRIPTION OF DRAWINGS

FIG. 5E. In vivo therapeutic validation of PTEN restoration using PTEN-mRNA NP in PCa xenograft model. The effect of PTEN-mRNA-PGDP NP treatment in PC3 tumor-bearing xenograft mice was evaluated by Immunohistochemistry staining of HA-PTEN (bar indicates 200 µm) on fixed tumor tissue after PBS, EGFP-mRNA-PGDP NP, or PTEN-mRNA-PGDP NP treatment (scale bar: 200 µm).

FIG. 6A. In vivo therapeutic validation of PTEN restoration using PTEN-mRNA NPs in disseminated metastatic PCa model. Scheme of i.v. tumor inoculation and systemic injection (i.v., tail-vein) of PBS, EGFP-mRNA-PGDP NP, or PTEN-mRNA-PGDP NP (n=8 mice per cohort) in disseminated PC3-luc metastatic male athymic nude mice.

FIG. 6B. In vivo therapeutic validation of PTEN restoration using PTEN-mRNA NPs in disseminated metastatic PCa model. Bioluminescent imaging for disseminated PC3-luc metastatic tumors at different time points post treatment.

FIG. 9A. In vitro toxicity and transfection efficiency of mRNA NP in DU145 cells, which were treated with various mRNA concentrations (at 0.062, 0.125, 0.250, 0.500 μg/mL) of EGFP-mRNA-PGCP NP. AlamarBlue cytotoxicity assay. Percent cell viability was normalized with the untreated control group (mean±SD, n=3).

FIG. 9B. Transfection efficiency percentages were determined using flow cytometry (mean±SD, n=4).

FIG. 18A. Biodistribution of Cy5-PTEN-mRNA NP. Accumulation of naked Cy5-PTEN-mRNA, Cy5-PTEN-mRNA-PGCP NP, and Cy5-PTEN-mRNA-PGDP NP in different organs including tumors in athymic nude mice bearing PC3-xenograft tumor 24 h post-injection.

FIG. 18B. Mean fluorescent intensity (MFI) was analyzed using ImageJ software and graphed using GraphPad Prism (mean±SD, n=3).

DETAILED DESCRIPTION

Figure 1A:
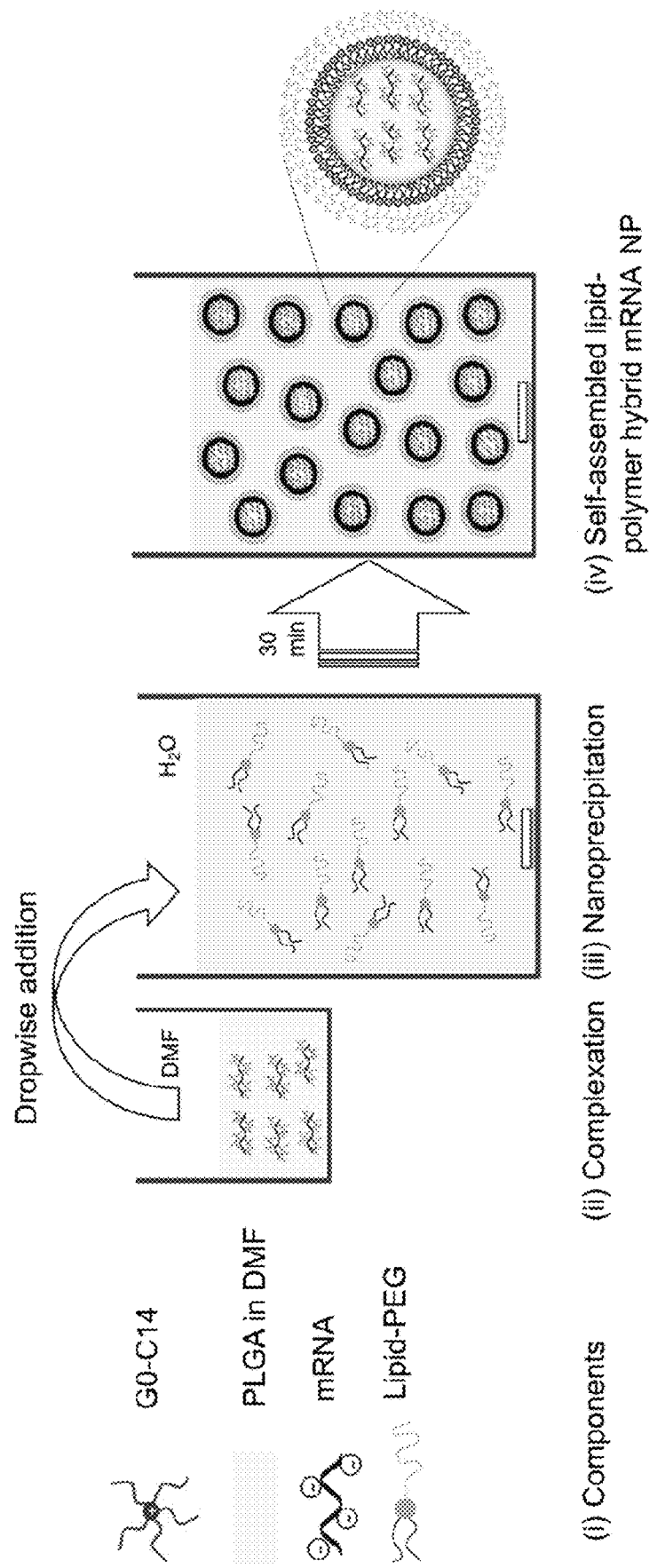
FIG. 1A. Preparation and characterization of mRNA NP. Self-assembly process of polymer-lipid hybrid mRNA NP and schematic representation of NP structure (i-iv). After self-assembly of cationic G0-C14 with anionic mRNA together with PLGA, the formulated polymer-lipid hybrid core was coated with lipid-PEG (EGFP-mRNA was used as reporter mRNA).

Loss and/or mutation of tumor-suppressor genes is a dominant force in tumor development and clinical resistance to a variety of therapies[53]. Reversal of the phenotype induced by loss of tumor suppressors has long proven an elusive goal. Two major strategies have been employed for suppressor restoration: restoring a functional copy of a given tumor-suppressor gene via transfection; and the use of small-molecule agents to reactivate tumor-suppressor function via conformational change in the mutated molecule[54].

Major hurdles in restoring suppressor gene in tumors have included inefficient delivery to targeted tumor cells, poor transfection efficacy, insufficient expression, and possible insertional mutagenesis. Consequently, restoring tumor-suppressor activity in cancer cells is highly challenging and requires the design of a functionally improved tumor suppressor with unique therapeutic modality that can withstand the rigors of systemic delivery, especially in the metastatic setting where the tumor burden is widely distributed.

The tumor suppressor-mRNA delivery platform reported herein is an example of such an approach. To the best of the present inventors' knowledge, this is the first report of any kind of tumor inhibition following direct systemic restoration of tumor-suppressor gene using an mRNA delivery strategy in vivo. Use of an mRNA delivery platform allows rapid gene expression with controlled and predictable expression kinetics, higher transfection efficiency, and (most importantly) can eliminate genomic complexation and mutagenesis due to the inherent cytoplasmic and diminished nuclear expression of the desired protein[29]. In addition, described herein is a delivery system that in some embodiments uses a new-generation lipid-polymer hybrid NP platform that provides effective intravenous delivery of the suppressor mRNA to tumor xenografts. The end result is restoration of function of the exemplary tumor suppressor PTEN as illustrated by inhibited both primary and advanced tumor growth, increased apoptosis, and blockade of the PI3K-AKT signaling pathway. Because PTEN loss is frequent in late-stage PCa, this approach can be useful in this patient population.

In previous reports, the most widely investigated non-viral gene delivery carriers such as polyethylenimine (PEI), DOTAP/cholesterol liposome, and the DOTAP/DOPE system[49, 55-57] provided only suboptimal and variable mRNA transfection efficacy (40-80%) in cancer cells and fibroblasts (e.g., HeLa and NIH 3T3 cells). In addition, in PCa cells (e.g., PC3) it was reported that mRNA transfection efficacy of the PEI/mRNA complex was only 30%, although those researchers found a high in vitro mRNA transfection activity in PC3 cells using a histidine-rich reducible polycation system[58]. The exemplary polymer-lipid hybrid mRNA NPs described herein, which were prepared using a robust self-assembly strategy, provided 86-98.2% mRNA transfection capacity with minimal toxicity in various PCa cell lines (e.g., LNCaP, PC3, and DU145), a new standard for in vitro delivery of mRNA to tumors. Potential reasons for this effective mRNA delivery to tumors may be the relatively small and tunable size of the NPs (about 20-250 nm), as well as their high and tunable mRNA encapsulation efficiency (10-100%) and loading efficiency (0.2-20%), compact shape, and good stability. Whereas smaller particle size could be achieved with small oligonucleotides such as siRNA, it is more difficult with larger payloads such as mRNA. It is worth noting that such small NPs may more efficiently permeate the leaky tumor microvasculature and achieve greater tumor accumulation and deeper tissue penetration compared to larger NPs[59-61].

For systemic in vivo application, PEGylation of NPs is a well-documented strategy to prevent rapid elimination from the circulation, since it reduces the interaction between NPs and serum proteins following recognition by mononuclear phagocytic system-mediated clearance mechanisms[62, 63]. Simultaneously, PEGylation could also hinder NP interactions with the target cell membrane, which may decrease tumor cell-mediated uptake. Therefore, proper dissociation of lipid-PEG molecules is necessary for optimal systemic circulation and extravasation of our mRNA NPs at the tumor site as well as effective uptake by tumor cells. The dissociation kinetics depend on the structure of the lipid-PEG molecules in the hybrid NPs and may be controlled by the length and/or saturation of lipophilic tails[45]. In that context, DSPE-PEG exhibited relatively slow de-PEGylation profile compared to ceramide-PEG, as described earlier from measurements of lipid-PEG's dissociation kinetics from NPs in the presence of serum albumin, which is the most abundant plasma protein and binds with diacyl lipids[64]. Moreover, a quicker release of ceramide-PEG than DSPE-PEG from NPs was observed, and the surface charge of the NPs changed over time after lipid-PEG dissociation: the charge of ceramide-PEG NPs rapidly increased from 2.2 to 31.4 mV in 3 h, but slowly for DSPE-PEG NPs from −4.0 to 11.9 mV over 24 h, although both NPs were initially near neutral. This slow de-PEGylation profile conferred better PK, tumor biodistribution, and therapeutic efficacy for DSPE-PEG NPs[45]. Thus the hybrid mRNA NP coated with DSPE-PEG showed higher stability, longer circulation, and increased tumor accumulation compared to ceramide-PEG NP, indicating more efficient systemic restoration of mRNA to tumors and implications beyond any particular tumor suppressor and cancer type.

PTEN loss has been recognized for two decades as being involved in PCa progression[65-67]; surprisingly, there has been no progress on direct restoration of PTEN function in PTEN-null PCa cells, presumably due to the inefficient delivery and insufficient expression of PTEN at the tumor site. Recently, a secreted form of PTEN called PTEN-long (PTEN-L) that can penetrate cells has been discovered and shown to rescue PTEN function in PTEN-null U87-MG glioblastoma cells and MDA-MB-468 breast cancer cells in vitro and in vivo[68].

The present approach is generalizable to a wide variety of tumor-suppressive molecules. Recent protein structure studies have reported that PTEN and PTEN-L have different properties relating to conformational change, membrane binding, and substrate specificity[69]. Future studies will be necessary to explore the relative efficacy of these two approaches. It is further likely that delivery of mRNA NPs will achieve greater tumor-specific distribution than free protein. It was also recently reported that PTEN loss promotes resistance to clinical therapy as well as T-cell-mediated immunotherapy[70, 71], thus restoring functional PTEN via the PTEN mRNA NP platform described herein can also be used in combination with immunotherapeutic applications and in rescuing chemosensitivity in resistant tumors; delivery of mRNA NPs also holds the potential to potentiate other therapeutic approaches[29]. The present findings provide significant support for the proof-of-concept that the systemic restoration of PTEN rescues PTEN function in PTEN-null PCa and effectively suppresses tumor progression with negligible side-effects.

Thus, provided herein are methods for NP-mediated mRNA delivery of tumor suppressors (e.g., PTEN) as therapeutics for the treatment of cancer.

Methods of Treatment

The methods described herein include methods for the treatment of cancers associated with loss of a tumor suppressor. In some embodiments, the disorder is PTEN-null Prostate Cancer (PCa). Generally, the methods include administering a therapeutically effective amount of one or more tumor suppressor mRNAs complexed with a delivery vehicle as described herein, e.g., a nanoparticle, to a subject who is in need of, or who has been determined to be in need of, such treatment. In some embodiments, the delivery vehicle (e.g., nanoparticle) is complexed with mRNAs that encode a single tumor suppressor; in other embodiments, the vehicle is complexed with mRNAs coding for multiple tumor suppressors. In some embodiments, the methods include administering a plurality vehicle-RNA complexes that include vehicles complexed with two or more mRNAs, e.g., wherein the vehicles are each complexed with only a single kind of mRNA (i.e., each vehicle is complexed with mRNA encoding one tumor suppressor), or wherein the vehicles are each complexed with two or more kinds of mRNAs (i.e., the vehicles are each complexed with mRNAs encoding two or more tumor suppressors).

As used in this context, to "treat" means to ameliorate at least one symptom of the cancer associated with loss of a tumor suppressor. Administration of a therapeutically effective amount of a compound described herein for the treatment of a cancer associated with loss of a tumor suppressor can result in, for example, increased expression of the tumor suppressor, and one or more of reduced tumor size, reduced tumor growth rate, reduced risk of metastasis, decrease risk of reoccurrence, and reduced number of tumors.

As used herein, the terms "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth.

The terms "cancer" or "neoplasms" include malignancies of the various organ systems, such as affecting lung, breast, thyroid, lymphoid, gastrointestinal, and genito-urinary tract, as well as adenocarcinomas that include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Additional examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

In some embodiments, the methods also include administering one or more immunotherapies.

Tumor Suppressor mRNA

The present methods include delivering mRNA encoding a tumor suppressor to a cell (e.g., a tumor cell) lacking that tumor suppressor. As used herein, a tumor suppressor is a protein that acts to reduce the potential for cancer and tumor formation by modulating cell growth, by negative regulation of the cell cycle or by promoting apoptosis. Thus, loss of a tumor suppressor (e.g., through mutation or dysregulation) can lead to unregulated cell growth and tumor development. Mutations and other alterations that are associated with cancer for each of the above are known in the art.

A number of Tumor Suppressors are known in the art. See, e.g., Table 1.

TABLE 1

| GENE | Genetic Alteration(s) | Associated Cancer(s) | GenBank Acc No. mRNA | Protein |
|------|----------------------|---------------------|----------------------|---------|
| PTEN | Point mutation, deletion | Prostate, breast, glioblastoma, melanoma, pancreatic cancer, colorectal cancer, leukemia | AF067844.1 | AAD13528.1 |
| APC | Point mutation, deletion | Adenomatous polyposis and sporadic colorectal cancer tumors, gastric | M74088.1 | AAA03586.1 |
| ARF | Deletion | Breast carcinomas, colorectal, adenoma glioblastoma | AF208864.1 | AAF64278.1 |

TABLE 1-continued

| GENE | Genetic Alteration(s) | Associated Cancer(s) | GenBank Ace No. mRNA | Protein |
|---|---|---|---|---|
| BMPR cancer | Point mutation | Gastrointestinal | NM_009758.4 | NP_033888.2 |
| BRCA1 | Point mutation | Ductal breast cancers, Epithelial ovarian cancers | U14680.1 | AAA73985.1 |
| E-cadherin | Point mutation | Loss of function leads to metastasis | Z13009.1 | CAA78353.1 |
| EXT1,2 | Point mutation, deletion, insertion | Hereditary multiple exostoses, also known as diaphyseal aclasis | S79639.1, U62740.1 | AAB62283.1 AAB07008.1 |
| FBXW7 | Point mutation, deletion | Breast cancer | AF411971.1 | AAL06290.1 |
| FH | Point mutation | Hereditary leiomyomatosis and renal-cell cancer | BC003108.1 | AAH03108.1 |
| GPC3 | Deletions, point mutation | Lung carcinoma | L47125.1 | AAA98132.1 |
| HIPK2 | Point mutation | Metastatic bladder cancer | AF208291 | AAG41236.1 |
| HRPT2 (CDC73) | Point mutation | Hereditary hyperpara-thyroidism-jaw tumor syndrome, Malignancy in sporadic parathyroid tumors | NM_024529.4 | NP_078805.3 |
| INPP4B | Deletion, loss of heterozygosity, reduced expression | Epithelial carcinomas and some human basal-like breast carcinomas | U96922.1 | AAB72153.1 |
| LKB1 | Point mutation, deletion | Human Lung Cancer (especially NSCLC), cervical carcinomas Inherited cancer disorder Peutz-Jeghers Syndrome | U63333.1 | AAB05809.1 |
| MEN1 | Point mutation | Pituitary tumors | U93236.1 | AAC51228.1 |
| MMR (MRC1) | Point mutation, reduced expression | Hereditary non-polyposis colon cancer | NM_002438.3 | NP_002429.1 |
| MUTYH | Point mutation, deletion | Lung and ovarian tumors, and lymphomas | U63329.1 | AAC50618.1 |
| NF1 | Point mutation, deletion | Juvenile myelomonocytic leukemia, Watson syndrome and breast cancer. | NM_000267.3 | NP_000258.1 |
| NF2 | Point mutation, deletion | Meningioma Thyroid cancer, mesothelioma, and melanoma | L11353.1 | AAA36212.1 |
| p15, p16 | Point mutation | Colorectal cancer, leukemia | AB060808.1 L27211.1 | BAB91133.1 AAA92554.1 |
| p53 | Point mutation, deletion | Lung Prostate | AF307851.1 NM_000546.5 | AAG28785.1 NP_000537.3 |
| p57 (CDKN1C) | Point mutation | Beckwith-Wiedemann syndrome | NM_000076.2 | NP_000067.1 |

TABLE 1-continued

| GENE | Genetic Alteration(s) | Associated Cancer(s) | GenBank Acc No. mRNA | Protein |
|---|---|---|---|---|
| Ptch | Point mutation | Cell carcinomas of the skin, ovarian fibromas, and medulloblastomas | NM_000264.4 | NP_000255.2 |
| RB1 | Point mutation, deletion | Prostate cancer Pituitary melanotroph tumors | NM_000321.2 | NP_000312.2 |
| RECQL4 | Point mutation | Osteosarcoma | AB006532.1 | BAA74453.1 |
| SDH | Point mutation, deletion | Paraganglioma, renal cell carcinoma | U17248.1 | AAA81167.1 |
| Smad2/3 | Point mutation, deletions | Breast cancer | U65019.1 BC050743.1 | AAB17054.1 AAH50743.1 |
| Smad4 | Point mutation | Pancreatic Gastric Carcinoma | U44378.1 | AAA91041.1 |
| Su(Fu) | Point mutation, deletion | Brain tumor | NM_016169.3 | NP_057253.2 |
| TGFβR | Point mutation | Head and neck cancers, cervical and ovarian carcinomas | NM_001306210.1 | NP_001293139.1 |
| TSC1/TSC2 | Point mutation | Tuberous sclerosis complex | AF013168.1 AB014460.1 | AAC51674.1 BAA32694.1 |
| VHL | Point mutation, deletion, hyper-methylation | Renal carcinomas | NM_000551.3 | NP_000542.1 |
| WT1 | Point mutation, deletion | Haematological malignancies Pediatric nephroblastoma Wilms tumor | NM_000378.4 | NP_000369.3 |
| XPA | Point mutation | Bladder cancer | NM_000380.3 | NP_000371.1 |
| XPC | Point mutations, splice variants | ESCC, gastric cancer | NM_004628.4 | NP_004619.3 |
| XPD (ERCC2) | Point mutation | Glioma, NSCLC, Sarcoma | NM_000400.3 | NP_000391.1 |
| α-catenin (CTNNA1) | Point mutation | Basal-like breast cancer | NM_001323983.1 | NP_001310912.1 |
| RASSF1A | Hyper-methylation, point mutation | Lung, Cervical Cancer | NM_007182.4 | NP_009113.3 |
| SDHB | Point mutation | Kidney Paragangliomas | NM_003000.2 | NP_002991.2 |
| SIN3B | Point mutation | Prostate cancer | NM_015260.3 | NP_056075.1 |
| RGS12 | Point mutation | Prostate cancer | NM_198227.1 | NP_937870.1 |
| Kai1 metastasis suppressor (CD82) | Deletion, mutation and loss of expression | Prostate cancer | NM_002231.3 | NP_002222.1 |
| ING1B | Point mutation | Prostate cancer, Brain tumors | NM_198218.2 | NP_937861.1 |
| Atg7 | Deletion | Prostate cancer | NM_001349232.1 | NP_001336161.1 |
| JARID1D (KDM5D) | Point mutation | Prostate cancer | NM_001146705.1 | NP_001140177.1 |
| PALB2 | Point mutation | Breast cancer | NM_024675.3 | NP_078951.2 |
| TP53BP1 | Point mutation | Breast cancer | NM_001141980.2 | NP_001135452.1 |
| RAD51 | Point mutation | Breast cancer | NM_133487.3 | NP_597994.3 |
| XRCC4 | Point mutation | Breast cancer | NM_003401.4 | NP_003392.1 |
| KEAP1 | Point mutation | Liver cancer | NM_203500.1 | NP_987096.1 |
| KEAP1 | Point mutation | Liver cancer | NM_012289.3 | NP_036421.2 |
| RPS6KA3 | Point mutation | Liver cancer | NM_004586.2 | NP_004577.1 |
| RARβ | Point mutation | Lung cancer | NM_000965.4 | NP_000956.2 |
| FHIT | Point mutation | Lung cancer | NM_002012.3 | NP_002003.1 |
| PTCH1 | Point mutation | Lung cancer | NM_001083602.2 | NP_001077071.1 |
| DCC | Point mutation | Colorectal cancer | NM_005215.3 | NP_005206.2 |
| BAX | Point mutation | Colorectal cancer | NM_001291428.1 | NP_001278357.1 |
| AML1 (RUNX1) | Point mutation | Acute myeloid leukemia | NM_001754.4 | NP_001745.2 |
| CDKN2A | Point mutation | Bladder | NM_000077.4 | NP_000068.1 |
| CDKN1B | Point mutation | Prostate cancer | NM_004064.4 | NP_004055.1 |

TABLE 1-continued

| GENE | Genetic Alteration(s) | Associated Cancer(s) | GenBank Acc No. mRNA | Protein |
|---|---|---|---|---|
| NKX3-1 | Point mutation | Prostate cancer | NM_006167.3 | NP_006158.2 |
| RPP14 | Point mutation | Melanoma | NM_001098783.2 | NP_001092253.1 |
| CDK4 | Point mutation | Melanoma | NM_000075.3 | NP_000066.1 |
| CDK6 | Point mutation | Melanoma | NM_001259.7 | NP_001250.1 |

The above sequences are exemplary, as some of the above genes may have multiple transcript variants; generally speaking, the methods can include using an mRNA sequence for the variant that is predominantly expressed in a normal, non-cancerous cell of the same type as the tumor. The methods can include using a nucleotide sequence coding for an mRNA that is at least 80% identical to a reference sequence in Table 1. In some embodiments, the nucleotide sequences are at least 85%, 90%, 95%, 99% or 100% identical.

To determine the percent identity of two sequences, the sequences are aligned for optimal comparison purposes (gaps are introduced in one or both of a first and a second amino acid or nucleic acid sequence as required for optimal alignment, and non-homologous sequences can be disregarded for comparison purposes). The length of a reference sequence aligned for comparison purposes is at least 80% (in some embodiments, about 85%, 90%, 95%, or 100%) of the length of the reference sequence. The nucleotides or residues at corresponding positions are then compared. When a position in the first sequence is occupied by the same nucleotide or residue as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent identity between two amino acid sequences can be determined using the Needleman and Wunsch ((1970) J. Mol. Biol. 48:444-453) algorithm which has been incorporated into the GAP program in the GCG software package, using a Blossum 62 scoring matrix with a gap penalty of 12, a gap extend penalty of 4, and a frameshift gap penalty of 5.

As noted above, the delivery vehicle (e.g., nanoparticle) can be complexed with one, two or more mRNAs (e.g., a plurality of mRNAs) that encode a single tumor suppressor, or encoding multiple tumor suppressors.

In some embodiments, e.g., wherein the cancer is prostate cancer, the mRNA is PTEN. In some embodiments, the mRNA is p53. In some embodiments, the mRNA is RB. In some embodiments, the mRNAs are PTEN and p53. In some embodiments, the mRNAs are PTEN and RB. In some embodiments, the mRNAs are RB and p53. In some embodiments, the mRNAs are PTEN, p53 and RB.

In preferred embodiments, the mRNA encodes the human PTEN tumor suppressor, and in some embodiments, the cancer is breast cancer, prostate cancer, or glioblastoma. In some embodiments, the methods include determining that a subject has a cancer that is associated with loss of a tumor suppressor, and then delivering an mRNA encoding that tumor suppressor to the subject, e.g., to the tumor in the subject. Determining that a subject has a cancer that is associated with loss of a tumor suppressor can be done using any method known in the art, e.g., obtaining a sample comprising tumor cells, and detecting the presence of a mutation or loss of a tumor suppressor in the cells, e.g., by sequencing DNA of the tumor cells and detecting a mutation that is known to be associated with oncogenesis, or by detecting a decreased level or activity of the tumor suppressor protein as compared to a reference, e.g., a reference that represents a level or activity of the protein in a normal, non-cancerous cell of the same type as the tumor cell (i.e., a cell from the same kind of tissue, a non-cancerous part of the same tissues in the same individual or in an individual who doesn't have cancer).

A mature mRNA is generally comprised of five distinct portions (see FIG. 1a of Islam et al., Biomater Sci. 2015 December; 3(12):1519-33): (i) a cap structure, (ii) a 5' untranslated region (5' UTR), (iii) an open reading frame (ORF), (iv) a 3' untranslated region (3' UTR) and (v) a poly(A) tail (a tail of 100-250 adenosine residues). Typically, the mRNA will be in vitro transcribed using methods known in the art. The mRNA will typically be modified, e.g., to extend half-life or to reduce immunogenicity. For example, the mRNA can be capped with an anti-reverse cap analog (ARCA), in which OCH3 is used to replace or remove natural 3' OH cap groups to avoid inappropriate cap orientation. Tetraphosphate ARCAs or phosphorothioate ARCAs can also be used (Islam et al. 2015). The mRNA is preferably enzymatically polyadenylated (addition of a poly adenine (A) tail to the 3' end of mRNA), e.g., to comprise a poly-A tail of at least 100 or 150 As. Typically poly(A) polymerase is used; E. coli poly(A) polymerase (E-PAP) I has been optimized to add a poly(A) tail of at least 150 adenines to the 3' terminal of in vitro transcribed mRNA. Preferably, any adenylate-uridylate rice elements (AREs) are removed or replaced with 3' UTR of a stable mRNA species such as β-globin mRNA. Iron responsive elements (IREs) can be added in the 5' or 3' UTR. In some embodiments, the mRNAs include full or partial (e.g., at least 50%, 60%, 70%, 80%, or 90%) substitution of cytidine triphosphate and uridine triphosphate with naturally occurring 5-methylcytidine and pseudouridine (ψ) triphosphate. See Islam et al., 2015, and references cited therein.

mRNA Delivery Vehicles

In the present methods and compositions, the mRNA encoding a tumor suppressor is complexed with a delivery vehicle. The delivery vehicle can include, inter alia, protamine complexes and particles such as lipid nanoparticles, polymeric nanoparticles, lipid-polymer hybrid nanoparticles, and inorganic (e.g., gold) nanoparticles, e.g., as described in Islam et al., 2015.

Particles may be microparticles or nanoparticles. Nanoparticles are preferred for intertissue application, penetration of cells, and certain routes of administration. The nanoparticles may have any desired size for the intended use. The nanoparticles may have any diameter from 10 nm to 1,000 nm. The nanoparticle can have a diameter from 10 nm to 900 nm, from 10 nm to 800 nm, from 10 nm to 700 nm, from 10 nm to 600 nm, from 10 nm to 500 nm, from 20 nm from 500 nm, from 30 nm to 500 nm, from 40 nm to 500 nm, from 50 nm to 500 nm, from 50 nm to 400 nm, from 50 nm to 350 nm, from 50 nm to 300 nm, or from 50 nm to 200 nm. In preferred embodiments the nanoparticles can have a diameter less than 400 nm, less than 300 nm, or less than 200 nm. The preferred range is between 50 nm and 300 nm.

A. Nanoparticle as Delivery Vehicles

Nanoparticles can be polymeric particles, non-polymeric particles (e.g., a metal particle, quantum dot, ceramic, inorganic material, bone, etc.), liposomes, micelles, polymeric micelles, viral particles, hybrids thereof, and/or combinations thereof. In some embodiments, the nanoparticles are, but not limited to, one or a plurality of lipid-based nanoparticles, polymeric nanoparticles, metallic nanoparticles, surfactant-based emulsions, dendrimers, buckyballs, nanowires, virus-like particles, peptide or protein-based particles (such as albumin nanoparticles) and/or nanoparticles that are developed using a combination of nanomaterials such as lipid-polymer nanoparticles. In some embodiments, nanoparticles can comprise one or more polymers.

Nanoparticles may be a variety of different shapes, including but not limited to spheroidal, cubic, pyramidal, oblong, cylindrical, toroidal, and the like. Nanoparticles can comprise one or more surfaces. Exemplary nanoparticles that can be adapted for use include (1) the biodegradable nanoparticles disclosed in U.S. Pat. No. 5,543,158 to Gref et al., (2) the polymeric nanoparticles of Published US Patent Application 20060002852 to Saltzman et al., or (4) the lithographically constructed nanoparticles of Published US Patent Application 20090028910 to DeSimone et al.

Additional delivery forms include biodegradable, or non-biodegradable polymeric units in a form of an implant such as a rod, disc (wafer), or microchip, or in particulate form, such as microparticle or nanoparticle form. The delivery forms typically have dimensions suitable for implantation into tissues. These local delivery forms are placed at a desired site in a subject's body and release the agent(s) locally in a dosage not sufficient to cause systemic efficacy or side effects. For example, discs may have a diameter of between 1 mm and 10 mm and a thickness of between 0.5 mm and 3 mm. The rods may have a length of between 1 mm and 10 mm, and a width of between 0.5 mm and 3 mm.

Polymeric microchips for multi-dose delivery are described by Richards, et al., *Nat Mater.* (2003) 2(11):709-10 and Kim, et al. *J Control Release.* (2007) 123(2):172-8. Biodegradable polymeric microchips can be fabricated as described in these studies for release of the nucleic acids over an extended period, for example, 142 day. As described in these papers, the microchips were 1.2 cm in diameter, 480-560 microm thick and had 36 reservoirs that could each be filled with a different chemical. The devices were fabricated from poly(L-lactic acid) and had poly(D,L-lactic-co-glycolic acid) membranes of different molecular masses covering the reservoirs.

A drug delivery system can be designed to release pulses of different drugs at intervals after implantation in a patient by using different molecular masses or materials for the membrane. The devices can also be designed to have differential degradation rates in vivo and in vitro, using different polymer composition and/or molecular weights, such as biocompatible poly(lactic acid) and poly(glycolic acid) homo- and co-polymers for a polymeric drug-delivery microchip. See U.S. Pat. Nos. 6,491,666, 6,527,762, 6,976,982, 7,226,442, and 7,604,628. Suitable devices can be obtained from Microchips Biotech.

1. Lipid-Based Delivery Vehicles

In some embodiments, nanoparticles may optionally comprise one or more lipids. In some embodiments, a nanoparticle may comprise a liposome. In some embodiments, a nanoparticle may comprise a lipid bilayer. In some embodiments, a nanoparticle may comprise a lipid monolayer. In some embodiments, a nanoparticle may comprise a micelle. In some embodiments, a nanoparticle may comprise a core comprising a polymeric matrix surrounded by a lipid layer (e.g., lipid bilayer, lipid monolayer, etc.). In some embodiments, a nanoparticle may comprise a non-polymeric core (e.g., metal particle, quantum dot, ceramic particle, bone particle, viral particle, etc.) surrounded by a lipid layer (e.g., lipid bilayer, lipid monolayer, etc.).

The percent of lipid in nanoparticles can range from 0% to 99% by weight, from 10% to 99% by weight, from 25% to 99% by weight, from 50% to 99% by weight, or from 75% to 99% by weight. In some embodiments, the percent of lipid in nanoparticles can range from 0% to 75% by weight, from 0% to 50% by weight, from 0% to 25% by weight, or from 0% to 10% by weight. In some embodiments, the percent of lipid in nanoparticles can be approximately 1% by weight, approximately 2% by weight, approximately 3% by weight, approximately 4% by weight, approximately 5% by weight, approximately 10% by weight, approximately 15% by weight, approximately 20% by weight, approximately 25% by weight, or approximately 30% by weight.

In some embodiments, lipids are oils. In general, any oil known in the art can be included in nanoparticles. In some embodiments, oil may comprise one or more fatty acid groups or salts thereof. In some embodiments, a fatty acid group may comprise digestible, long chain (e.g., C8-C50), substituted or unsubstituted hydrocarbons. In some embodiments, a fatty acid group may be a C10-C20 fatty acid or salt thereof. In some embodiments, a fatty acid group may be a C15-C20 fatty acid or salt thereof. In some embodiments, a fatty acid group may be a C15-C25 fatty acid or salt thereof. In some embodiments, a fatty acid group may be unsaturated. In some embodiments, a fatty acid group may be monounsaturated. In some embodiments, a fatty acid group may be polyunsaturated. In some embodiments, a double bond of an unsaturated fatty acid group may be in the cis conformation. In some embodiments, a double bond of an unsaturated fatty acid may be in the trans conformation.

In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linolenic, gamma-linoleic, arachidonic, gadoleic, arachidonic, eicosapentaenoic, docosahexaenoic, or erucic acid. In some embodiments, the oil is a liquid triglyceride.

Suitable oils for use include plant oils and butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

In some embodiments, a lipid is a hormone (e.g. estrogen, testosterone), steroid (e.g., cholesterol, bile acid), vitamin (e.g. vitamin E), phospholipid (e.g. phosphatidyl choline), sphingolipid (e.g. ceramides), or lipoprotein (e.g. apolipoprotein).

In certain embodiments, a lipid to be used in liposomes can be, but is not limited to, one or a plurality of the following: phosphatidylcholine, lipid A, cholesterol, dolichol, sphingosine, sphingomyelin, ceramide, glycosylceramide, cerebroside, sulfatide, phytosphingosine, phosphatidyl-ethanolamine, phosphatidylglycerol, phosphatidylinositol, phosphatidylserine, cardiolipin, phosphatidic acid, and lyso-phophatides. In certain embodiments, a targeting moiety can be conjugated to the surface of a liposome.

In some embodiments, nanoparticle-stabilized liposomes are used to deliver the disclosed nucleic acid content. By allowing small charged nanoparticles (1 nm-30 nm) to adsorb on liposome surface, liposome-nanoparticle complexes have not only the merits of bare liposomes, but also tunable membrane rigidity and controllable liposome stability. When small charged nanoparticles approach the surface of liposomes carrying either opposite charge or no net charge, electrostatic or charge-dipole interaction between nanoparticles and membrane attracts the nanoparticles to stay on the membrane surface, being partially wrapped by lipid membrane. This induces local membrane bending and globule surface tension of liposomes, both of which enable tuning of membrane rigidity. Moreover, adsorbed nanoparticles form a charged shell which protects liposomes against fusion, thereby enhancing liposome stability. In certain embodiments, small nanoparticles are mixed with liposomes under gentle vortex, and the nanoparticles stick to liposome surface spontaneously. In specific embodiments, small nanoparticles can be, but are not limited to, polymeric nanoparticles, metallic nanoparticles, inorganic or organic nanoparticles, hybrids thereof, and/or combinations thereof.

In some embodiments, liposome-polymer nanoparticles are used to deliver a combination of one or more inhibitory nucleic acids and one or more nucleic acids encoding a protein or polypeptide.

2. Lipid-Polymer Delivery Vehicles

In some embodiments, nanoparticles comprise one or more polymers associated covalently, or non-covalently with one or more lipids. In the preferred embodiments, nanoparticles comprise one or more phospholipids.

In some embodiments, a polymeric matrix can be surrounded by a coating layer (e.g., liposome, lipid monolayer, micelle, etc.). In one embodiment, the lipid monolayer shell comprises an amphiphilic compound. In another embodiment, the amphiphilic compound is lecithin. In another embodiment, the lipid monolayer is stabilized.

Specific examples of amphiphilic compounds include, but are not limited to, phospholipids, such as 1,2 distearoyl-sn-glycero-3-phosphoethanolamine (DSPE), dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), and dilignoceroylphosphatidylcholine (DLPC), incorporated at a ratio of between 0.01-60 (weight lipid/w polymer), most preferably between 0.1-30 (weight lipid/w polymer). Phospholipids which may be used include, but are not limited to, phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and β-acyl-y-alkyl phospholipids. Examples of phospholipids include, but are not limited to, phosphatidylcholines such as dioleoylphosphatidylcholine, dimyristoylphosphatidylcholine, dipentadecanoylphosphatidylcholine dilauroylphosphatidylcholine, dipalmitoylphosphatidylcholine (DPPC), distearoylphosphatidylcholine (DSPC), diarachidoylphosphatidylcholine (DAPC), dibehenoylphosphatidylcho-line (DBPC), ditricosanoylphosphatidylcholine (DTPC), dilignoceroylphosphatidylcholine (DLPC); and phosphatidylethanolamines such as dioleoylphosphatidylethanolamine or 1-hexadecyl-2-palmitoylglycerophosphoethanolamine. Synthetic phospholipids with asymmetric acyl chains (e.g., with one acyl chain of 6 carbons and another acyl chain of 12 carbons) may also be used.

In a particular embodiment, an amphiphilic component that can be used to form an amphiphilic layer is lecithin, and, in particular, phosphatidylcholine. Lecithin is an amphiphilic lipid and, as such, forms a phospholipid bilayer having the hydrophilic (polar) heads facing their surroundings, which are oftentimes aqueous, and the hydrophobic tails facing each other. Lecithin has an advantage of being a natural lipid that is available from, e.g., soybean, and already has FDA approval for use in other delivery devices.

In certain embodiments, the amphiphilic layer of the nanoparticle, e.g., the layer of lecithin, is a monolayer, meaning the layer is not a phospholipid bilayer, but exists as a single continuous or discontinuous layer around, or within, the nanoparticle. A monolayer has the advantage of allowing the nanoparticles to be smaller in size, which makes them easier to prepare. The amphiphilic layer is "associated with" the nanoparticle, meaning it is positioned in some proximity to the polymeric matrix, such as surrounding the outside of the polymeric matrix (e.g., PLGA), or dispersed within the polymers that make up the nanoparticle.

By covering the polymeric nanoparticles with a thin film of small molecule amphiphilic compounds, the nanoparticles have merits of both polymer- and lipid-based nanoparticles, while excluding some of their limitations. The amphiphilic compounds form a tightly assembled monolayer around the polymeric core. This monolayer effectively prevents the carried agents from freely diffusing out of the nanoparticle, thereby enhancing the encapsulation yield and slowing drug release. Moreover, the amphiphilic monolayer also reduces water penetration rate into the nanoparticle, which slows hydrolysis rate of the biodegradable polymers, thereby increasing particle stability and lifetime.

In further embodiments, targeting ligands can be conjugated to the amphiphilic component prior to incorporating them into the nanoparticle, the composition of the nanoparticle and its surface properties can be more accurately quantified. Alternatively, targeting ligands can be conjugated the polymeric component of the nanoparticles.

a. Lipid-Conjugated Polymers

In some embodiments, the nanoparticle comprises a polymeric matrix, wherein the polymeric matrix comprises a lipid-terminated polymer such as polyalkylene glycol and/or a polyester. In some embodiments, the nanoparticle comprises an amphiphilic lipid-terminated polymer, where a cationic and/or an amniotic lipid is conjugated to a hydrophobic polymer. In one embodiment, the polymeric matrix comprises lipid-terminated PEG.

In some embodiments, the polymeric matrix comprises lipid-terminated copolymer. In another embodiment, the polymeric matrix comprises lipid-terminated PEG and PLGA.

In one embodiment, the lipid is 1,2 distearoyl-sn-glycero-3-phosphoethanolamine (DSPE), and salts thereof. In a preferred embodiment, the polymeric matrix comprises DSPE-terminated PEG. The lipid-terminated PEG can then, for example, be mixed with PLGA to form a nanoparticle.

3. Amphiphilic Polymers

In some embodiments, long-circulating, optionally cell-penetrating, and stimuli-responsive nanoparticles for effective in vivo delivery of therapeutic, prophylactic and/or diagnostic agents are used. In the preferred embodiment, the NPs are made of an amphiphilic polymer, most preferably a PEGylated polymer, which shows a response to a stimulus such as pH, temperature, or light, such as an ultra pH-responsive characteristic with a pKa close to the endosomal pH (6.0-6.5) (Wang Y et al, *Nat Mater,* 13, 204-212 (2014)). The polymer may include a targeting or cell penetrating or adhesion molecule such as a tumor-penetrating peptide iRGD.

Stimuli responsive polymers are well known in the art. Stimuli responsive amphiphilic polymers, especially those that can self-assembly to form nanoparticles, are not. However, it is possible to make stimuli responsive amphiphilic copolymers through selection of a hydrophilic or hydrophobic polymer component of the copolymer, or by modification of the hydrophilic or hydrophobic polymers.

The nanoparticles can be formed by self-assembly in an emulsion of a non-aqueous solvent with an aqueous solvent of a first amphiphilic polymer containing a polymer represented by Formula I:

$$(X)_m\text{—}(Y)_n \qquad \text{Formula I}$$

wherein, m and n are independently integers between one and 1000, inclusive. X is a hydrophobic polymer and Y is a hydrophilic polymer, and at least one of X, Y, or both, is stimuli-responsive. Optionally the nanoparticles are formed by self-assembly of a mixture of polymers represented by Formula I and a second polymer containing a polymer represented by Formula II:

$$(Q)_c\text{-}(R)_d \qquad \text{Formula II}$$

wherein, c and d are independently integers between zero and 1000, inclusive, with the proviso that the sum (c+d) is greater than one. Q and R are independently hydrophilic or hydrophobic polymers. Optionally, the nanoparticles are formed by self-assembly of a mixture of polymers represented by Formula I and Formula II, wherein the polymer represented by Formula I, Formula II, or both, contains a ligand, wherein the ligand is a targeting ligand, an adhesion ligand, a cell-penetrating ligand, or an endosomal-penetrating ligand, with the proviso that the ligand is conjugated to the hydrophilic polymer.

In some embodiments, the nanoparticles are formed by self-assembly of a mixture of first stimuli-responsive hydrophobic polymer and a second polymer containing a polymer represented by Formula III:

$$(S)_e\text{-}(T)_f \qquad \text{Formula III}$$

wherein, e and f are independently integers between zero and 1000, inclusive, with the proviso that the sum (e+f) is greater than one. S and T are independently a hydrophilic polymer or a hydrophobic polymer. Optionally, the first stimuli-response hydrophobic polymer, the polymer represented by Formula III, or both contains a ligand, wherein the ligand is a targeting ligand, an adhesion ligand, a cell-penetrating ligand, or an endosomal-penetrating ligand, with the proviso that the ligand is conjugated to the hydrophilic polymer.

In some embodiments, the nanoparticles are formed by self-assembly of a mixture of first stimuli-responsive hydrophilic polymer and a second polymer containing a polymer represented by Formula III:

$$(S)_e\text{-}(T)_f \qquad \text{Formula III}$$

wherein, e and f are independently integers between zero and 1000, inclusive, with the proviso that the sum (e+f) is greater than one. S and T are independently a hydrophilic polymer or a hydrophobic polymer. Optionally, the first stimuli-response hydrophilic polymer, the polymer represented by Formula III, or both contains a ligand, wherein the ligand is a targeting ligand, an adhesion ligand, a cell-penetrating ligand, or an endosomal-penetrating ligand, with the proviso that the ligand is conjugated to the hydrophilic polymer.

Optionally, the polymers that form the nanoparticles contain linkers between the blocks of hydrophilic and hydrophobic polymers, between the hydrophilic polymer and ligand, or both.

Amphiphilic copolymers can spontaneously self-assemble in aqueous solution to form NPs with hydrophobic inner core and hydrophilic outer shells. The hydrophobic inner core can be used to deliver therapeutic and diagnostic agents including genes, proteins, chemotherapeutic drugs, or other small molecules. The incorporation of stimuli-responsive moieties to the hydrophobic core can easily accomplish the spatiotemporal control over the macroscopic properties of NPs, and thereby the release of the encapsulated cargo at the desired site.

The amphiphilic polymers are responsive to a stimulus. This may be a pH change, redox change, temperature change, exposure to light or other stimuli, including binding to a target. The responsiveness may be imparted solely by the hydrophilic polymer, the hydrophobic polymer or the conjugate per se. The nanoparticles are formed of a mixture or blend of polymers. Some may be the amphiphilic polymers, preferably copolymers of modified polyethylene glycol (PEG) and polyesters, such as various forms of PLGA-PEG or PLA-PEG copolymers, collectively referred to herein as "PEGylated polymers", some hydrophobic polymer such as PLGA, PLA or PGA, and/or some may be hydrophilic polymer such as a PEG or PEG derivative. Some will be modified by conjugation to a targeting agent, a cell adhesion or a cell penetrating peptide.

Besides amphiphilic copolymers, hydrophobic polymers can be also used to develop stimuli-responsive NPs for various biomedical applications. For these hydrophobic polymers, their NPs are prepared by using the mixture of the hydrophobic polymer and amphiphilic polymer or amphiphilic compound. The amphiphilic compound can include, but is not limited to, one or a plurality of naturally derived lipids, lipid-like materials, surfactants, or synthesized amphiphilic compounds.

The length of hydrophilic and/or hydrophobic polymers can be optimized to optimize encapsulation of agent to be delivered, i.e., encapsulation efficiency (EE %). As demonstrated in the examples, as the PDPA length increases, the EE % and size of the resulting NPs increase (Table 3), possibly because the increased PDPA length leads to an increase in the size of the hydrophobic core. Specifically, the EE % reaches almost 100% for the polymer with 80 (PDPA80) or 100 (PDPA100) DPA repeat units. Notably, using a mixture of Meo-PEG-b-P(DPA-co-GMA-TEPA-C14) (90 mol %) and tumor-penetrating polymer (iRGD-PEG-b-PDPA, 10 mol %) to prepare NPs does not cause obvious change in the EE % or particle size.

The amphiphilic polymers include a hydrophilic polymer. This is preferably at an end which can orient to the exterior of the nanoparticles when formed by emulsion techniques such as self-assembly.

Polymers and copolymers that can be used to make the nanoparticles disclosed herein include, but are not limited to, polymers including glycolic acid units, referred to herein as "PGA", and lactic acid units, such as poly-L-lactic acid, poly-D-lactic acid, poly-D,L-lactic acid, poly-L-lactide, poly-D-lactide, and poly-D,L-lactide, collectively referred to herein as "PLA", and caprolactone units, such as poly(δ-caprolactone), collectively referred to herein as "PCL"; and copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA"; polyacrylates, polyanhydrides, poly (ester anhydrides), poly-4-hydroxybutyrate (P4HB) combinations and derivatives thereof.

The polymer is preferably a biocompatible polymer. One simple test to determine biocompatibility is to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise uptaken by such cells.

The biocompatible polymer is preferably biodegradable, i.e., the polymer is able to degrade, chemically and/or biologically, within a physiological environment, such as within the body.

In some embodiments, the delivery vehicles comprise amphiphile-polymer particles, e.g., comprising a water-insoluble polymeric core and a payload and at least one amphiphile within the core, as described in WO2016/065306, which is incorporated herein by reference in its entirety.

In preferred embodiments, the nanoparticles comprise a core of mRNA complexed with cationic lipid-like compound G0-C14 and poly(lactic-co-glycolic acid) (PLGA) polymer, coated with a lipid-poly(ethylene glycol) (lipid-PEG) shell, e.g., (e.g., DSPE-PEG (1,2-distearoyl-sn-glycero-3-phosphoethanolamine-N-[methoxy {polyethylene glycol]}) or ceramide-PEG (N-palmitoyl-sphingosine-1-(succinyl{methoxy[polyethylene glycol]}) with PEG molecular weight (MW) 2000-5000)[45] (see, e.g., FIG. 1A herein). G0-C14 can be used for mRNA complexation, and PLGA, a widely clinically used biodegradable and biocompatible polymer, provides a stable NP core.

a. Stimuli that the Polymers can be Responsive to

The polymers can be responsive to changes in pH-, redox-, light-, temperature-, enzyme-, ultrasound-, or other stimuli such as a conformation change resulting from binding.

Almeida, et al. *J. Applied Pharm.l Sci.* 02 (06)01-10 (2012) is an excellent review of stimuli responsive polymers. The signs or stimuli that trigger the structural changes on smart polymers can be classified in three main groups: physical stimuli (temperature, ultrasound, light, mechanical stress), chemical stimuli (pH and ionic strength) and biological stimuli (enzymes and bio molecules).

Stimuli can be artificially controlled (with a magnetic or electric field, light, ultrasounds, etc.) or naturally promoted by internal physiological environment through a feedback mechanism, leading to changes in the polymer net that allow the drug delivery without any external intervention (for example: pH changes in certain vital organs or related to a disease; temperature change or presence of enzymes or other antigens) or by the physiological condition. In the presence of a sign or stimuli, changes can happen on the surface and solubility of the polymer as well as on sol-gel transition.

Smart polymers can be classified according to the stimuli they respond to or to their physical features. Regarding the physical shape, they can be classified as free linear polymer chain solutions, reversible gels covalently cross-linked and polymer chain grafted to the surface.

Stimuli responsive polymers are also reviewed by James, et al., Acta Pharma. Sinica B 4(2):120-127 (2014). The following is a list of exemplary polymers categorized by responsive to various stimuli:

Temperature: POLOXAMERS, poly(N-alkylacrylamide)s, poly(N-vinylcaprolactam)s, cellulose, xyoglucan, and chitosan pH: poly(methacrylic acid)s, poly(vinylpyridine)s, and poly(vinylimmidazole)s light: modified poly(acrylamide)s electric field: sulfonated polystyrenes, poly(thiophene)s, and poly(ethyloxazoline)s ultrasound: ethylenevinylacetate These transitions are reversible and include changes in physical state, shape and solubility, solvent interactions, hydrophilic and lipophilic balances and conductivity. The driving forces behind these transitions include neutralization of charged groups by the addition of oppositely charged polymers or by pH shift, and change in the hydrophilic/lipophilic balance or changes in hydrogen bonding due to increase or decrease in temperature. Responses of a stimulus-responsive polymer can be of various types. Responsiveness of a polymeric solution initiated by physical or chemical stimuli is limited to the destruction and formation of various secondary forces including hydrogen bonding, hydrophobic forces, van der Waals forces and electrostatic interaction. Chemical events include simple reactions such as oxidation, acid-base reaction, reduction and hydrolysis of moieties attached to the polymer chain. In some cases, dramatic conformational change in the polymeric structure occurs, e.g., degradation of the polymeric structure due to irreversible bond breakage in response to an external stimulus.

b. pH Dependent Polymers

Exemplary pH dependent polymers include dendrimers formed of poly(lysine), poly(hydroxyproline), PEG-PLA, Poly(propyl acrylic acid), Poly(ethacrylic acid), CARBOPOLL®, Polysilamine, EUDRAGIT® S-100 EUDRAGIT® L-100, Chitosan, PMAA-PEG copolymer, sodium alginate (Ca2+). The ionic pH sensitive polymers are able to accept or release protons in response to pH changes. These polymers contain acid groups (carboxylic or sulfonic) or basic groups (ammonium salts) so that the pH sensitive polymers are polyelectrolytes that have in their structure acid or basic groups that can accept or release protons in response to pH changes in the surrounding environment. pH values from several tissues and cell compartments can be used to trigger release in these tissues. For example, the pH of blood is 7.4-7.5; stomach is 1.0-3.0; duodenum is 4.8-8.2; colon is 7.0-7.5; lysosome is 4.5-5.0; Golgi complex is 6.4; tumor-extracellular medium is 6.2-7.2.

Examples of these polymers include poly(acrylic acid) (PAA) (CARBOPOL1®) and derivatives, poly(methacrylic acid) (PMAA), poly (2-(diisopropylamino) ethylmethacrylate) (PDPA), poly (2-(hexamethyleneimino) ethyl methacrylate), poly(2-diethylaminoethyl methacrylate) (PDEAEMA), poly(ethylene imine), poly(L-lysine) and poly(N,N-dimethylaminoethylmetha crylate) (PDMAEMA). Polymers with functional acid groups pH sensitive polymers include poly(acrylic acid) (PAA) or poly(methacrylic) acid (PMAA) are polyanions that have in their structure a great number of ionizable acid groups, like carboxylic acid or sulfonic acid. The pH in which acids become ionized depends on the polymer's pKa (depends on the polymer's composition and molecular weight). Polymers with functional basic groups include polycations such as poly(4-vinylpyridine), poly(2-vinylpyridine) (PVP) and poly(vinylamine) (PVAm), are protonated at high pH values and positively ionized at neutral or low pH values, i.e., they go through a phase transition at pH 5 due to the deprotonation of the pyridine groups. Other polybases are poly(N,N-dimethylaminoethyl methacrylate) (PDMAEMA) and poly (2-diethylaminoethyl methacrylate) (PDEAEMA), with amino groups in their structure which in acid environments gain protons, and in basic environments release the protons. Examples of polycationic polyelectrolyte polymers are poly (N,N-diakyl aminoethyl methacrylate), poly(lysine) (PL), poly(ethylenimine) (PEI) and chitosan. Commercially available polymers include EUDRAGIT L® and EUDRAGIT S® from Röhm Pharma GmBH (with methacrylic acid and methylmethacrylate in their composition), CMEC (a cellulose derivative) from Freund Sangyo Co., CAP by Wako Pure Chemicals Ltd., HP-50 and ASM by Shin-Etsu Chemical Co., Ltd.

There are several natural polymers (for example, albumin, gelatin and chitosan) that present pH sensibility. Chitosan is a cationic amino polysaccharide, derivative from chitin, which is biocompatible and resorbable. Additional examples include the anionic polymer PEAA (polyethacrylic acid) or by PPAA (polypropyl acrylic acid), Polypropylacrylic acid (PPAA) and polyethacrylic acid (PEAA), and poly(ethylene glycol)-poly(aspartame hydrazine doxorubicin) [(PEG-p (Asp-Hid-dox), and polycationic polymers, such as poly(2-diethylaminoethyl methacrylate) (PDEAEMA).

c. Temperature Dependent Polymers

Temperature dependent polymers are sensitive to the temperature and change their microstructural features in response to change in temperature. Thermo-responsive polymers present in their structure a very sensitive balance between the hydrophobic and the hydrophilic groups and a small change in the temperature can create new adjustments. If the polymeric solution has a phase below the critical solution temperature, it will become insoluble after heating. Above the critical solution temperature (LCST), the interaction strengths (hydrogen linkages) between the water molecules and the polymer become unfavorable, it dehydrates and a predominance of the hydrophobic interaction occurs, causing the polymer to swell. The LSCT is the critical temperature in which the polymeric solution shows a phase separation, going from one phase (isotropic state) to two phases (anisotropic state). The accumulation of temperature sensitive polymeric systems in solid tumors is due to the increased impermeability effect to the tumor vascular net retention and to the use of an external impulse (heat source) on the tumor area. This temperature increase promotes the changing of the microstructure of the polymeric system, turning it into gel and releasing the drug, thus increasing the drug in the intra-tumoral area and the therapeutic efficiency, and reducing the side effects (MacEwan et al., 2010).

Examples of thermosensitive polymers include the poly (N-substituted acrylamide) polymers such as poly(N-isopoprylacrilamide) (PNIPAAm), poly (N,N'-diethyl acrylamide), poly (dimethylamino ethyl methacrylate and poly (N-(L)-(1-hydroxymethyl) propyl methacrylamide). Other examples of thermo-responsive polymers are: copolymers blocks of poly(ethylene glycol)/poly(lactide-coglicolide) (PEG/PLGA, REGEL®), polyoxyethylenepolyoxypropylene (PEO/PPO), triple blocks of copolymers polyoxyethylene-polyoxypropylene-polyoxyethylene (PEO-PPOPEO) and poly(ethylene glycol)-poly(lactic acid)-poly(ethylene glycol) (PEG-PLA-PEG). Exemplary polymers and their LCST: PNIPAAm, LCST 32° C.; PDEAAm, LCST 26-35° C.; PDMAEMA, LCST 50° C.; poly(N-(L)-(hydroxymethyl)propylmethacrylamide), LCST 30° C.

An increase of the hydrophobic monomers (as, for example, the butyl methacrylate) or on the molecular weight, results in a LCST decrease (Jeong, Gutowska, 2002). The incorporation of hydrophilic monomers such as acrylic acid or hydroxyethyl methacrylate) fosters the creation of increases LCST. The co-polymers NIPAAm conjugated with hydrophilic unities such as acrylic acid promotes the increase of LCST to temperatures around 37° C., i.e., the body temperature. Polymers with 2-hydroxyethyl (meth-acrylate) (HEMA) promote the increase of LCST above the body temperature POLOXAMERs and derivatives are well known temperature sensitive polymers. The copolymer blocks based on PEO-PPO sequences constitutes one family of triple blocks of commercialized copolymers with the following names: PLURONICS®, POLOXAMERS® AND TETRONICS®. POLOXAMERS® are non-ionic polymers polyoxyethylenepolyoxypropylene-polyoxyethylene (PEOn-PPOn-PEOn), with many pharmaceutical uses (Ricci et al., 2005). The triple block of copolymers PEO—PPO-PEO (PLURONICS® or POLOXAMERS®) get into gel at body temperature in concentrations above 15% (m/m). The POLOXAMERs® normally used are: 188 (F-68), 237 (F-87), 338 (F-108) and 407 (F-127). "F" refers to the polymer in the form of flakes. PLURONICS® and TETRONICS® are polymers approved by FDA to be used as food additives, pharmaceutical ingredients, drug carriers in parenteral systems, tissue engineering and agricultural products. PLURONIC F-127 (Polaxamer 407, PF-127) can also be used as carrier in several routes of administration, including oral, cutaneous, intranasal, vaginal, rectal, ocular and parenteral. PLURONIC® F127 (PF-127) or POLOXAMER 407 (P407) (copolymer polyoxyethylene 106-polyoxypropylene 70-polyoxyethylene106) contains about 70% of ethylene oxide which contributes to its hydrophilicity.

d. Polymers with Dual Stimuli-Responsiveness

To obtain a temperature and pH sensitive polymer it is only necessary to combine temperature sensitive monomers (as, for example, poly(N-isopropylacrylamide-co-methacrylic acid and PNIPAm) with pH sensitive monomers (as, for example, AA and MAA).

e. Polymers with Binding or Biological Responsiveness

Biologically responsive polymer systems are increasingly important in various biomedical applications. The major advantage of bioresponsive polymers is that they can respond to the stimuli that are inherently present in the natural system. Bioresponsive polymeric systems mainly arise from common functional groups that are known to interact with biologically relevant species, and in other instances the synthetic polymer is conjugated to a biological component. Bioresponsive polymers are classified into antigen-responsive polymers, glucose-sensitive polymers, and enzyme-responsive polymers.

Glucose-responsive polymeric-based systems have been developed based on the following approaches: enzymatic oxidation of glucose by glucose oxidase, and binding of glucose with lectin or reversible covalent bond formation with phenylboronic acid moieties. Glucose sensitivity occurs by the response of the polymer toward the byproducts that result from the enzymatic oxidation of glucose. Glucose oxidase oxidises glucose resulting in the formation of gluconic acid and $H_2O_2$. For example, in the case of poly (acrylicacid) conjugated with the GOx system, as the blood glucose level is increased glucose is converted into gluconic acid which causes the reduction of pH and protonation of PAA carboxylate moieties, facilitating the release of insulin. Another system utilizes the unique carbohydrate binding properties of lectin for the fabrication of a glucose-sensitive system. Concanavalin A (Con A) is a lectin possessing four binding sites and has been used frequently in insulin-modulated drug delivery. In this type of system the insulin moiety is chemically modified by introducing a functional group (or glucose molecule) and then attached to a carrier or support through specific interactions which can only be interrupted by the glucose itself. The glycosylated insulin-Con A complex exploits the competitive binding behaviour of Con A with glucose and glycosylated insulin. The free glucose molecule causes the displacement of glycosylated Con A-insulin conjugates.

Another approach includes polymers with phenylboronic groups and polyol polymers that form a gel through complex formation between the pendant phenylborate and hydroxyl groups. Instead of polyol polymers, short molecules such as diglucosylhexadiamine have been used. As the glucose concentration increases, the crosslinking density of the gel decreases and as a result insulin is released from the eroded gel. The glucose exchange reaction is reversible and reformation of the gel occurs as a result of borate-polyol cross-linking.

Field-responsive polymers respond to the application of electric, magnetic, sonic or electromagnetic fields. The additional benefit over traditional stimuli-sensitive polymers is their fast response time, anisotropic deformation due to directional stimuli, and also a controlled drug release rate simply by modulating the point of signal control.

f. Light-Sensitive Polymers

A light-sensitive polymer undergoes a phase transition in response to exposure to light. These polymers can be classified into UV-sensitive and visible-sensitive systems on the basis of the wavelength of light that triggers the phase transition.

A variety of materials are known, such as a leuco-derivative molecule, bis(4-dimethylamino)phenylmethyl leucocyanide, which undergoes phase transition behaviour in response to UV light. Triphenylmethane-leuco derivatives dissociate into ion-pairs such as triphenylmethyl cations upon UV irradiation. At a fixed temperature these hydrogels swell discontinuously due to increased osmotic pressure in response to UV irradiation but shrink when the stimulus is removed. Another example is a thermosensitive diarylated pluronic F-127.

Visible light-sensitive polymeric materials can be prepared by incorporating photosensitive molecules such as chromophores (e.g., trisodium salt of copper chlorophyllin). When light of appropriate wavelength is applied, the chromophore absorbs light which is then dissipated locally as heat by radiationless transition, increasing the local temperature of the polymeric material, leading to alteration of the swelling behavior. The temperature increase directly depends on the chromophore concentration and light intensity.

g. Electric Field-Sensitive Polymers

Electric field-sensitive polymers change their physical properties in response to a small change in electric current. These polymers contain a relatively large concentration of ionisable groups along the back bone chain that are also pH-responsive. Electro-responsive polymers transform electric energy into mechanical energy. The electric current causes a change in pH which leads to disruption of hydrogen bonding between polymer chains, causing degradation or bending of the polymer chain. Major mechanisms involved in drug release from electro-responsive polymer are diffusion, electrophoresis of charged drug, forced convection of drug out of the polymer or degradation of the polymer.

Naturally occurring polymers such as chitosan, alginate and hyalouronic acid are commonly employed to prepare electro-responsive materials. Major synthetic polymers that have been used include allyl amine, vinyl alcohol, acrylonitrile, methacrylic acid and vinylacrylic acid. In some cases, combinations of natural and synthetic polymers have been used. Most polymers that exhibit electro-sensitive behavior are polyelectrolytes and undergo deformation under an electric field due to anisotropic swelling or deswelling as the charged ions move towards the cathode or anode. Neutral polymers that exhibit electro-sensitive behavior require the presence of a polarisable component with the ability to respond to the electric field. Another example of a material which can be used is poly(2-acrylamido-2-methylpropane sulphonic acid-co-n-butylmethacrylate).

4. Hydrogel-Forming Polymers

In some embodiments, the delivery vehicles for the nucleic acids are formed from a biocompatible, hydrogel-forming polymer encapsulating the nucleic acids to be delivered. In some embodiments, the hydrogel is an anionic polymer that is cross-linked with a polycationic polymer. In some embodiments the nanoparticles are conFIG.d with a core and envelope structure. In these embodiments, the nucleic acids are preferably encapsulated in the core hydrogel and the drug-loaded polymeric particles are encapsulated within the envelope hydrogel. In preferred embodiments, the core and envelope hydrogels are separated by a membrane or shell.

Examples of materials which can be used to form a suitable hydrogel include polysaccharides such as alginate, polyphosphazines, poly(acrylic acids), poly(methacrylic acids), poly(alkylene oxides), poly(vinyl acetate), polyvinylpyrrolidone (PVP), and copolymers and blends of each. See, for example, U.S. Pat. Nos. 5,709,854, 6,129,761 and 6,858,229.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups and sulfonic acid groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

The biocompatible, hydrogel-forming polymer is preferably a water-soluble gelling agent. In preferred embodiments, the water-soluble gelling agent is a polysaccharide gum, more preferably a polyanionic polymer.

In some embodiments, the targeting ligands are covalently attached to hydrogel-forming polymers. In some embodiments, the nucleic acids to be targeted are attached to the hydrogel forming polymer via a linking moiety that is designed to be cleaved in vivo. The composition of the linking moiety can also be selected in view of the desired release rate of the nucleic acids.

5. Moieties Attached to Particles

The nanoparticles or other delivery vehicles can include binding moieties or targeting moieties that specifically bind to a target cell or tissue. Representative targeting moieties include, but are not limited to, antibodies and antigen binding fragments thereof, aptamers, peptides, and small molecules. The binding moiety can be conjugated to a polymer that forms the nanoparticle. Typically the binding moiety is displayed on the outer shell of the nanoparticle. The outer shell serves as a shield to prevent the nanoparticles from being recognized by a subject's immune system thereby increasing the half-life of the nanoparticles in the subject. The nanoparticles also contain a hydrophobic core. In preferred embodiments, the hydrophobic core is made of a biodegradable polymeric material. The inner core carries therapeutic payloads and releases the therapeutic payloads at a sustained rate after systemic, intraperitoneal, oral, pulmonary, or topical administration. The nanoparticles also optionally include a detectable label, for example a fluorophore or NMR contrast agent that allows visualization of nanoparticles within plaques.

The targeting moiety of the nanoparticle can be an antibody or antigen binding fragment thereof. The targeting moieties should have an affinity for a cell-surface receptor or cell-surface antigen on the target cells. The targeting moieties may result in internalization of the particle within the target cell.

The targeting moiety can specifically recognize and bind to a target molecule specific for a cell type, a tissue type, or an organ. The target molecule can be a cell surface polypeptide, lipid, or glycolipid. The target molecule can be a receptor that is selectively expressed on a specific cell surface, a tissue or an organ. Cell specific markers can be for specific types of cells including, but not limited to stem cells, skin cells, blood cells, immune cells, muscle cells, nerve cells, cancer cells, virally infected cells, and organ specific cells. The cell markers can be specific for endothelial, ectodermal, or mesenchymal cells. Representative cell specific markers include, but are not limited to cancer specific markers.

Exemplary targets include PSMA; GAH; HER2; Tf receptor; EpCAM; gC1qR (p32); Nucleolin; $\alpha v\beta 3/5$; Collagen IV; Fibronectin; FA receptor; and Mitochondria. Exemplary methods and moieties for targeting cancer cells, including proteins, peptides, nucleic acid-based ligands and small molecules, are described below and in Bertrand et al., Adv Drug Deliv Rev. 2014 February; 66: 2-25 (see esp. table 2 and section 3.4, "Targeting Ligands").

a. Peptide Targeting Moieties

In a preferred embodiment, the targeting moiety is a peptide. Specifically, the plaque targeted peptide can be, but is not limited to, one or more of the following: RGD, iRGD(CRGDK/RGPD/EC), LyP-1, P3(CKGGRAKDC), or their combinations at various molar ratios. The targeting peptides can be covalently associated with the polymer and the covalent association can be mediated by a linker. The peptides target to actively growing (angiogenic) vascular endothelial cells. Those angiogenic endothelial cells frequently appear in metabolic tissues such as adipose tissues.

b. Antibody Targeting Moieties

The targeting moiety can be an antibody or an antigen-binding fragment thereof. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. The antigen binding portion of the antibody can be any portion that has at least one antigen binding site, such as Fab, $F(ab')_2$, dsFv, sFv, diabodies, and triabodies. In certain embodiments, the antibody is a single chain antibody.

c. Aptamer Targeting Moieties

Aptamers are oligonucleotide or peptide sequences with the capacity to recognize virtually any class of target molecules with high affinity and specificity. Aptamers bind to targets such as small organics, peptides, proteins, cells, and tissues. Unlike antibodies, some aptamers exhibit stereoselectivity. The aptamers can be designed to bind to specific targets expressed on cells, tissues or organs.

d. Additional Moieties

The nanoparticles can contain one or more polymer conjugates containing end-to-end linkages between the polymer and a moiety. The moiety can be a targeting moiety, a detectable label, or a therapeutic, prophylactic, or diagnostic agent. For example, a polymer conjugate can be a PLGA-PEG-phosphonate. The additional targeting elements may refer to elements that bind to or otherwise localize the nanoparticles to a specific locale. The locale may be a tissue, a particular cell type, or a subcellular compartment. The targeting element of the nanoparticle can be an antibody or antigen binding fragment thereof, an aptamer, or a small molecule (less than 500 Daltons). The additional targeting elements may have an affinity for a cell-surface receptor or cell-surface antigen on a target cell and result in internalization of the particle within the target cell.

Pharmaceutical Compositions and Methods of Administration

The methods described herein include the use of pharmaceutical compositions comprising an mRNA encoding a tumor suppressor complexed with a delivery vehicle as an active ingredient.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions, e.g., an immunotherapy agent as described herein.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

The pharmaceutical compositions can be included in a container, pack, or dispenser together with instructions for administration.

Immunotherapy

In some embodiments, the methods also include co-administering an immunotherapy agent to a subject who is treated with a method or composition described herein. Immunotherapy agents include those therapies that target tumor-induced immune suppression; see, e.g., Stewart and Smyth, Cancer Metastasis Rev. 2011 March; 30(1):125-40.

Examples of immunotherapies include, but are not limited to, adoptive T cell therapies or cancer vaccine preparations designed to induce T lymphocytes to recognize cancer cells, as well as checkpoint inhibitors such as anti-CD137 (BMS-663513), anti-PD1 (e.g., Nivolumab, pembrolizumab/MK-3475, Pidilizumab (CT-011)), anti-PDL1 (e.g., BMS-936559, MPDL3280A), or anti-CTLA-4 (e.g., ipilumimab; see, e.g., Krüger et al., Histol Histopathol. 2007 June; 22(6):687-96; Eggermont et al., Semin Oncol. 2010 October; 37(5):455-9; Klinke D J., Mol Cancer. 2010 Sep. 15; 9:242; Alexandrescu et al., J Immunother. 2010 July-August; 33(6):570-90; Moschella et al., Ann N Y Acad Sci. 2010 April; 1194:169-78; Ganesan and Bakhshi, Natl Med J India. 2010 January-February; 23(1):21-7; Golovina and Vonderheide, Cancer J. 2010 July-August; 16(4):342-7.

Exemplary anti-PD-1 antibodies that can be used in the methods described herein include those that bind to human PD-1; an exemplary PD-1 protein sequence is provided at NCBI Accession No. NP_005009.2. Exemplary antibodies are described in U.S. Pat. Nos. 8,008,449; 9,073,994; and US20110271358, including PF-06801591, AMP-224, BGB-A317, BI 754091, JS001, MEDI0680, PDR001, REGN2810, SHR-1210, TSR-042, pembrolizumab, nivolumab, avelumab, pidilizumab, and atezolizumab.

Exemplary anti-CD40 antibodies that can be used in the methods described herein include those that bind to human CD40; exemplary CD40 protein precursor sequences are provided at NCBI Accession No. NP_001241.1, NP_690593.1, NP_001309351.1, NP_001309350.1 and NP_001289682.1. Exemplary antibodies include those described in WO2002/088186; WO2007/124299; WO2011/123489; WO2012/149356; WO2012/111762; WO2014/070934; US20130011405; US20070148163; US20040120948; US20030165499; U.S. Pat. No. 8,591,900; including dacetuzumab, lucatumumab, bleselumab, teneliximab, ADC-1013, CP-870,893, Chi Lob 7/4, HCD122, SGN-4, SEA-CD40, BMS-986004, and APX005M. In some embodiments, the anti-CD40 antibody is a CD40 agonist, and not a CD40 antagonist.

Exemplary anti-PD-L1 antibodies that can be used in the methods described herein include those that bind to human PD-L1; exemplary PD-L1 protein sequences are provided at NCBI Accession No. NP_001254635.1, NP_001300958.1, and NP_054862.1. Exemplary antibodies are described in US20170058033; WO2016/061142A1; WO2016/007235A1; WO2014/195852A1; and WO2013/079174A1, including BMS-936559 (MDX-1105), FAZ053, KNO35, Atezolizumab (Tecentriq, MPDL3280A), Avelumab (Bavencio), and Durvalumab (Imfinzi, MEDI-4736).

In some embodiments, these immunotherapies may primarily target immunoregulatory cell types such as regulatory T cells (Tregs) or M2 polarized macrophages, e.g., by reducing number, altering function, or preventing tumor localization of the immunoregulatory cell types. For example, Treg-targeted therapy includes anti-GITR monoclonal antibody (TRX518), cyclophosphamide (e.g., metronomic doses), arsenic trioxide, paclitaxel, sunitinib, oxaliplatin, PLX4720, anthracycline-based chemotherapy, Daclizumab (anti-CD25); Immunotoxin eg. Ontak (denileukin diftitox); lymphoablation (e.g., chemical or radiation lymphoablation) and agents that selectively target the VEGF-VEGFR signaling axis, such as VEGF blocking antibodies (e.g., bevacizumab), or inhibitors of VEGFR tyrosine kinase activity (e.g., lenvatinib) or ATP hydrolysis (e.g., using ectonucleotidase inhibitors, e.g., ARL67156 (6-N,N-Diethyl-D-β,γ-dibromomethyleneATP trisodium salt), 8-(4-chlorophenylthio) cAMP (pCPT-cAMP) and a related cyclic nucleotide analog (8-[4-chlorophenylthio] cGMP; pCPT-cGMP) and those described in WO 2007135195, as well as mAbs against CD73 or CD39). Docetaxel also has effects on M2 macrophages. See, e.g., Zitvogel et al., Immunity 39:74-88 (2013).

In another example, M2 macrophage targeted therapy includes clodronate-liposomes (Zeisberger, et al., Br J Cancer. 95:272-281 (2006)), DNA based vaccines (Luo, et al., J Clin Invest. 116(8): 2132-2141 (2006)), and M2 macrophage targeted pro-apoptotic peptides (Cieslewicz, et al., PNAS. 110(40): 15919-15924 (2013)). Some useful immunotherapies target the metabolic processes of immunity, and include adenosine receptor antagonists and small molecule inhibitors, e.g., istradefylline (KW-6002) and SCH-58261; indoleamine 2,3-dioxygenase (IDO) inhibitors, e.g., Small molecule inhibitors (e.g., 1-methyl-tryptophan (1MT), 1-methyl-d-tryptophan (D1MT), and Toho-1) or IDO-specific siRNAs, or natural products (e.g., Brassinin or exiguamine) (see, e.g., Munn, Front Biosci (Elite Ed). 2012 Jan. 1; 4: 734-45) or monoclonal antibodies that neutralize the metabolites of IDO, e.g., mAbs against N-formyl-kynurenine.

In some embodiments, the immunotherapies may antagonize the action of cytokines and chemokines such as IL-10, TGF-beta, IL-6, CCL2 and others that are associated with immunosuppression in cancer. For example, TGF-beta neutralizing therapies include anti-TGF-beta antibodies (e.g. fresolimumab, Infliximab, Lerdelimumab, GC-1008), antisense oligodeoxynucleotides (e.g., Trabedersen), and small molecule inhibitors of TGF-beta (e.g. LY2157299), (Wojtowicz-Praga, Invest New Drugs. 21(1): 21-32 (2003)). Another example of therapies that antagonize immunosuppression cytokines can include anti-IL-6 antibodies (e.g. siltuximab) (Guo, et al., Cancer Treat Rev. 38(7):904-910 (2012). mAbs against IL-10 or its receptor can also be used, e.g., humanized versions of those described in Llorente et al., Arthritis & Rheumatism, 43(8): 1790-1800, 2000 (anti-IL-10 mAb), or Newton et al., Clin Exp Immunol. 2014 July; 177(1):261-8 (Anti-interleukin-10R1 monoclonal antibody).

mAbs against CCL2 or its receptors can also be used. In some embodiments, the cytokine immunotherapy is combined with a commonly used chemotherapeutic agent (e.g., gemcitabine, docetaxel, cisplatin, tamoxifen) as described in U.S. Pat. No. 8,476,246.

In some embodiments, immunotherapies can include agents that are believed to elicit "danger" signals, e.g., "PAMPs" (pathogen-associated molecular patterns) or "DAMPs" (damage-associated molecular patterns) that stimulate an immune response against the cancer. See, e.g., Pradeu and Cooper, Front Immunol. 2012, 3:287; Escamilla-Tilch et al., Immunol Cell Biol. 2013 November-December; 91(10):601-10. In some embodiments, immunotherapies can agonize toll-like receptors (TLRs) to stimulate an immune response. For example, TLR agonists include vaccine adjuvants (e.g., 3M-052) and small molecules (e.g., Imiquimod, muramyl dipeptide, CpG, and mifamurtide (muramyl tripeptide)) as well as polysaccharide krestin and endotoxin. See, Galluzi et al., Oncoimmunol. 1(5): 699-716 (2012), Lu et al., Clin Cancer Res. Jan. 1, 2011; 17(1): 67-76, U.S. Pat. Nos. 8,795,678 and 8,790,655. In some embodiments, immunotherapies can involve administration of cytokines that elicit an anti-cancer immune response, see Lee & Margolin, Cancers. 3: 3856-3893(2011). For example, the cytokine IL-12 can be administered (Portielje, et al., Cancer Immunol Immunother. 52: 133-144 (2003)) or as gene therapy (Melero, et al., Trends Immunol. 22(3): 113-115 (2001)). In another example, interferons (IFNs), e.g., IFN-gamma, can be administered as adjuvant therapy (Dunn et al., Nat Rev Immunol. 6: 836-848 (2006)).

In some embodiments, immunotherapies can antagonize cell surface receptors to enhance the anti-cancer immune response. For example, antagonistic monoclonal antibodies that boost the anti-cancer immune response can include antibodies that target CTLA-4 (ipilimumab, see Tarhini and Iqbal, Onco Targets Ther. 3:15-25 (2010) and U.S. Pat. No. 7,741,345 or Tremelimumab) or antibodies that target PD-1 (nivolumab, see Topalian, et al., NEJM. 366(26): 2443-2454 (2012) and WO2013/173223A1, pembrolizumab/MK-3475, Pidilizumab (CT-011)).

Some immunotherapies enhance T cell recruitment to the tumor site (such as Endothelin receptor-A/B (ETRA/B) blockade, e.g., with macitentan or the combination of the ETRA and ETRB antagonists BQ123 and BQ788, see Coffman et al., Cancer Biol Ther. 2013 February; 14(2):184-92), or enhance CD8 T-cell memory cell formation (e.g., using rapamycin and metformin, see, e.g., Pearce et al., Nature. 2009 Jul. 2; 460(7251):103-7; Mineharu et al., Mol Cancer Ther. 2014 Sep. 25. pii: molcanther.0400.2014; and Berezhnoy et al., Oncoimmunology. 2014 May 14; 3: e28811). Immunotherapies can also include administering one or more of: adoptive cell transfer (ACT) involving transfer of ex vivo expanded autologous or allogeneic tumor-reactive lymphocytes, e.g., dendritic cells or peptides with adjuvant; cancer vaccines such as DNA-based vaccines, cytokines (e.g., IL-2), cyclophosphamide, anti-interleukin-2R immunotoxins, and/or Prostaglandin E2 Inhibitors (e.g., using SC-50). In some embodiments, the methods include administering a composition comprising tumor-pulsed dendritic cells, e.g., as described in WO2009/114547 and references cited therein. See also Shiao et al., Genes & Dev. 2011. 25: 2559-2572.

Unless explicitly defined elsewhere, the following definitions apply in the present application.

A "biocompatible polymer" is used here to refer to a polymer that does not typically induce an adverse response when inserted or injected into a living subject, for example, without significant inflammation and/or acute rejection of the polymer by the immune system, for instance, via a T-cell response.

A "copolymer" herein refers to more than one type of repeat unit present within the polymer defined below.

"Encapsulation efficiency" (EE) as used herein is the fraction of initial drug that is encapsulated by the nanoparticles (NPs).

"Loading" as used herein refers to the mass fraction of encapsulated agent in the NPs.

A "polymer," as used herein, is given its ordinary meaning as used in the art, i.e., a molecular structure including one or more repeat units (monomers), connected by covalent bonds. The polymer may be a copolymer. The repeat units forming the copolymer may be arranged in any fashion. For example, the repeat units may be arranged in a random order, in an alternating order, or as a "block" copolymer, i.e., including one or more regions each including a first repeat unit (e.g., a first block), and one or more regions each including a second repeat unit (e.g., a second block), etc. Block copolymers may have two (a diblock copolymer), three (a triblock copolymer), or more numbers of distinct blocks.

A "polymeric conjugate" as used herein refers to two or more polymers (such as those described herein) that have been associated with each other, usually by covalent bonding of the two or more polymers together. Thus, a polymeric conjugate may comprise a first polymer and a second polymer, which have been conjugated together to form a block copolymer where the first polymer is a first block of the block copolymer and the second polymer is a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. In some embodiments, the polymeric conjugate is amphiphilic, for example by conjugating a hydrophilic polymer, or a cationic/anionic lipid to a hydrophobic polymer.

As used herein, the term "amphiphilic" refers to a property where a molecule has both a polar portion and a non-polar portion. Often, an amphiphilic compound has a polar head attached to a long hydrophobic tail. In some embodiments, the polar portion is soluble in water, while the non-polar portion is insoluble in water. In addition, the polar portion may have either a formal positive charge, or a formal negative charge. Alternatively, the polar portion may have both a formal positive and a negative charge, and be a zwitterion or inner salt. The amphiphilic compound can be, but is not limited to, one or a plurality of the following: naturally derived lipids, surfactants, or synthesized compounds with both hydrophilic and hydrophobic moieties.

A "particle" refers to any entity having a diameter of less than 10 microns (μm). Typically, particles have a longest dimension (e.g., diameter) of 1000 nm or less. In some embodiments, particles have a diameter of 300 nm or less. Particles include microparticles, nanoparticles, and picoparticles. In some embodiments, particles can be a polymeric particle, non-polymeric particle (e.g., a metal particle, quantum dot, ceramic, inorganic material, bone, etc.), liposomes, micelles, hybrids thereof, and/or combinations thereof. As used herein, the term "nanoparticle" refers to any particle having a diameter of less than 1000 nm. In preferred embodiments, a nanoparticle is a polymeric particle that can be formed using a solvent emulsion, spray drying, or precipitation in bulk or microfluids, wherein the solvent is removed to no more than an insignificant residue, leaving a solid (which may, or may not, be hollow or have a liquid filled interior) polymeric particle, unlike a micelle whose form is dependent upon being present in an aqueous solution.

"Hydrogel" refers to a substance formed when an organic polymer (natural or synthetic) is cross-linked via covalent, ionic, or hydrogen bonds to create a three-dimensional open-lattice structure which entraps water molecules to form a gel. Biocompatible hydrogel refers to a polymer forms a gel which is not toxic to living cells, and allows sufficient diffusion of oxygen and nutrients to the entrapped cells to maintain viability.

As used herein, the term "carrier" or "excipient" refers to an organic or inorganic ingredient, natural or synthetic inactive ingredient in a formulation, with which one or more active ingredients are combined.

As used herein, the term "pharmaceutically acceptable" means a non-toxic material that does not interfere with the effectiveness of the biological activity of the active ingredients.

As used herein, the terms "effective amount" or "therapeutically effective amount" means a dosage sufficient to alleviate one or more symptoms of a disorder, disease, or condition being treated, or to otherwise provide a desired pharmacologic and/or physiologic effect. The precise dosage will vary according to a variety of factors such as subject-dependent variables (e.g., age, immune system health, etc.), the disease or disorder being treated, as well as the route of administration and the pharmacokinetics of the agent being administered.

The term "modulate" as used herein refers to the ability of a compound to change an activity in some measurable way as compared to an appropriate control. As a result of the presence of compounds in the assays, activities can increase or decrease as compared to controls in the absence of these compounds. Preferably, an increase in activity is at least 25%, more preferably at least 50%, most preferably at least 100% compared to the level of activity in the absence of the compound. Similarly, a decrease in activity is preferably at least 25%, more preferably at least 50%, most preferably at least 100% compared to the level of activity in the absence of the compound.

The terms "inhibit" and "reduce" means to reduce or decrease in activity or expression. This can be a complete inhibition or reduction of activity or expression, or a partial inhibition or reduction. Inhibition or reduction can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

As used herein, the term "prevention" or "preventing" means to administer a composition to a subject or a system at risk for or having a predisposition for one or more symptom caused by a disease or disorder to cause cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

The terms "sufficient" and "effective", as used interchangeably herein, refer to an amount (e.g. mass, volume, dosage, concentration, and/or time period) needed to achieve one or more desired result(s).

The term "protein" "polypeptide" or "peptide" refers to a natural or synthetic molecule comprising two or more amino acids linked by the carboxyl group of one amino acid to the alpha amino group of another.

The term "polynucleotide" or "nucleic acid sequence" refers to a natural or synthetic molecule comprising two or more nucleotides linked by a phosphate group at the 3' position of one nucleotide to the 5' end of another nucleotide. The polynucleotide is not limited by length, and thus the polynucleotide can include deoxyribonucleic acid (DNA) or ribonucleic acid (RNA).

EXAMPLES

The invention is further described in the following examples, which do not limit the scope of the invention described in the claims.

Materials and Methods

The following materials and methods were used in the Examples below.

Materials. Ester-terminated poly(D,L-lactide-co-glycolide) (PLGA, viscosity 0.26-0.54 dL/g) was purchased from Durect Corporation. Cationic ethylenediamine core-poly(amidoamine) (PAMAM) generation 0 dendrimer (G0), bafilomycin A1 (Baf A1) were purchased from Sigma-Aldrich. Filipin III, chlorpromazine (CPZ) and 5-(N-ethyl-N-isopropyl)-amiloride (EIPA) were purchased from Cayman Chemicals (Ann Arbor, Mich., USA). DSPE-PEG (1,2-distearoyl-sn-glycero-3-phosphoethanolamine-N-[methoxy {polyethylene glycol}]) with PEG molecular weight (MW) 5000, and ceramide-PEG (N-palmitoyl-sphingosine-1-(succinyl{methoxy[polyethylene glycol]}) with PEG MW of 2000 were obtained from Avanti Polar Lipids. Lipofectamine 2000 (L2K) was purchased from Invitrogen. EGFP mRNA (EGFP mRNA; modified with 5-methylcytidine and pseudouridine) and Cyanine 5 fluorescent dye-labeled EGFP mRNA (Cy5 EGFP mRNA; modified with 5-methylcytidine and pseudouridine modification) were purchased from TriLink Biotechnologies. Sequence-verified human PTEN wildtype, G129E, and G129R open reading frame were cloned into pENTR223 followed by recombination into the Gateway destination vector pHAGE (MSCV—N-Flag-HA-IRES-PURO, long terminal repeat [LTR]-driven expression) using λ recombinase. pLenti CMV Puro LUC (W168) was a gift from Eric Campeau (Addgene plasmid #17477)[72]. ViraPower Lentiviral packaging mix was purchased from Thermo Fisher Scientific. D-luciferin-K+ salt bioluminescent substrate (#122799) was obtained from PerkinElmer. Primary antibodies used in this work included the following: anti-PTEN (138G6), anti-p-Akt-ser473 (#9271), anti-p-70S6K-Thr389 (108D2), anti-p-FOXO3a-Ser318/321 (#9465), anti-p-PARS40-Thr246 (D4D2), p-4E-BP1-Thr37/46 (236B4), p-4E-BP1-Ser65 (#9451) and anti-PARP (#9542) antibodies (rabbit, Cell Signaling); anti-HA antibody (3F10) (rat, Roche); anti-HA-HRP conjugated antibody (A00169) (goat, GenScript); Anti-GFP antibody (A-6455) (rabbit, Life Technologies).

Preparation of modified PTEN mRNA. Vector carrying open-reading frame (ORF) of PTEN was a gift from William Sellers[73] (pSGSL HA PTEN wt; Addgene #10750). The vector was linearized by ApaI/EcoRI digestion and purified. HA-PTEN ORF under the regulation of T7 promoter was then amplified by PCR reaction. The amplicons were further purified and used as templates for in vitro transcription (IVT). The modified PTEN-mRNA was synthesized as described previously[48, 49] In brief, IVT was conducted using MEGAscript T7 kit (Ambion) with 1-2 µg template and 7.5 mM ATP, 1.5 mM GTP, 7.5 mM 5-methyl-CTP, 7.5 mM pseudo-UTP (TriLink Biotechnologies), and 6 mM 3'-0-Me-m$^7$G(5')ppp(5')G (anti-reverse cap analog, ARCA) (TriLink Biotechnologies). Reactions were incubated at 37° C. for 4 hours, followed by Turbo DNase treatment for 15 min. 3' poly(A)-tails were further added to IVT RNA products using a poly(A) tailing kit (Ambion). mRNA was purified by using the MEGAclear kit (Ambion), then treated with Antarctic Phosphatase (New England Biolab) at 37° C. for 30 min, and further purified. Large-scale PTEN mRNA was custom-prepared by TriLink Biotechnologies as above (ARCA capped and enzymatically polyadenylated; fully substituted with Pseudo-U and 5'-Methyl-C; DNase and phosphatase treatment; Silica membrane purification) using 100-150 µg template containing T7 promoter and HA-PTEN ORF.

Synthesis of cationic lipid compound (G0-C14). The cationic lipid-like compound (G0-C14) was synthesized from ethylenediamine core-poly(amidoamine) (PAMAM) generation 0 dendrimer (G0) using a ring-opening reaction by reacting with 1,2 epoxytetradecane according to previously described procedure[45, 74]. Briefly, 1,2 epoxytetradecane was mixed with PAMAM dendrimers G0 at a molar ratio of 7:1, where substoichiometric amounts of 1,2 epoxytetradecane were added to increase the proportion of products with one less tail than the total possible for a given amine monomer. The reaction was carried out for 2 days under vigorous stirring, and the crude mixture was separated on silica with gradient elution from $CH_2Cl_2$ to 75:22:3 $CH_2Cl_2$/MeOH/$NH_4$OH using chromatography.

mRNA complexation ability of G0-C14 and its stability in organic solvent. To assess the mRNA complexation ability of G0-C14 and its stability in organic solvent (DMF), naked EGFP-mRNA or EGFP-mRNA complexed with G0-C14 (in varying weight ratios from 1 to 20) were incubated with or without DMF for 30 min. For mRNA samples in DMF, electrophoresis was run without extracting mRNA from DMF into aqueous solution. The volumes of samples were then adjusted with loading dye (Invitrogen) and run into an E-Gel® 2% agarose (Invitrogen) gel for 30 min at 50 V. The Ambion® Millennium™ markers-formamide (Thermo Fisher Scientific) was used as a ladder. Finally the gel was imaged under UV and the bands were analyzed.

Preparation of mRNA NP. We employed a robust, innovative self-assembly method to prepare mRNA-encapsulated polymer-lipid hybrid NPs as we previously described[45], but with significant modification and optimization in ratios of reagents used in NP formulation. In brief, PLGA and G0-C14 were dissolved separately in dimethylformamide (DMF) at concentrations of 5 mg/ml and 2.5 mg/ml, respectively. Then PLGA (250 µg in 50 µl) and G0-C14 (250 µg in 100 µl) were mixed at a weight ratio of 1:1 in a small glass vial. mRNA (16 µg at 1 mg/ml concentration) in aqueous solution was mixed into the PLGA/G0-C14 organic solution (weight ratio of mRNA:PLGA:G0-C14 was 1:15:15) to form cationic lipid/mRNA nanocomplexes. This solution was then quickly nanoprecipitated into 10 ml of lipid-PEG (e.g., ceramide-PEG or DSPE-PEG) aqueous solution (0.1 mg/ml concentration in DNase/RNase-free Hypure water) for ~20 seconds. The weight ratio of lipid-PEG to PLGA was 4:1. Upon nanoprecipitation, NPs formed instantly and were kept for 30 min at 600 rpm stirring at room temperature to stabilize. The NPs were then washed three times with ice-cold Hypure water using Amicon tubes (MWCO 100 kDa; Millipore) to remove organic solvent and free compounds and finally concentrated into 1 ml PBS solution. The NPs were used fresh or kept at −80° C. to use later for various in vitro and in vivo studies. The mRNA NPs were run through gel electrophoresis as described above to check for any unencapsulated mRNA leaching. The NPs prepared with ceramide-PEG and DSPE-PEG were termed PGCP and PGDP NPs, respectively.

Physicochemical characterization and stability of mRNA NPs in serum condition. mRNA NPs were characterized by assessing their size, surface charge, and morphology. Sizes were measured by NanoSIGHT (Malvern, NS300) at 20° C. and analyzed using Nanoparticle Tracking Analysis (NTA), which utilizes the properties of both light scattering and Brownian motion to determine the particle size distribution of samples in liquid suspension. The surface charge of the NPs was determined by dynamic light scattering (DLS) with 15-mW laser and an incident beam of 676 nm (Brookhaven Instrument Corporation). A transmission electron microscope (TEM) was used to assess the NPs' morphology and shape. For TEM, NPs were stained with 1% uranyl acetate and imaged using a Tecnai $G^2$ Spirit BioTWIN microscope (FEI Company) at 80 kV. To check the in vitro stability of polymer-lipid hybrid mRNA NPs in serum as a means to mimic in vivo conditions, mRNA NPs were incubated in 10% serum containing PBS solution at 37° C. in triplicate for various time periods (0, 2, 4, 8, 12, 24, and 48 h) with 100 rpm shaking. At each time point, an aliquot of NPs solution was taken for particle size measurement using NanoSIGHT and analyzed as described above to evaluate any change in size distribution at various time intervals. EGFP mRNA NPs were used in this study.

Cell culture. Human PCa cell lines (PC3, DU145, LNCaP and its invasive subclone LNCaP LN3) and prostate epithelial cells (PreC) along with two breast cancer cell lines (MDA-MB-468 and MDA-MB-231) were used in various in vitro studies. All cells were purchased from American Type Culture Collection (ATCC). Cells were maintained in F-12K (ATCC), Eagle's Minimum Essential Medium (EMEM; ATCC), Roswell Park Memorial Institute (RPMI) 1640 (ATCC), or Leibovitz's L-15 (ATCC) cell-culture medium, according to the culture method for each cell type per the instructions from ATCC, supplemented with high-glucose, 10% fetal bovine serum (FBS; Gibco®) and 1% penicillin/streptomycin antibiotic (Thermo-Fisher Scientific). Cell culture and all biological experiments were performed at 37° C. in 5% $CO_2$ conditions in a cell-culture incubator. All cells were authenticated (using the "DDC Biomedical" or "Genetica DNA Laboratories" cell line authentication test) and checked for mycoplasma contamination before in vitro cell experiments and in vivo xenograft tumor model preparation.

Generation of luciferase-tagged PC3 cells. The lentiviral vector pLenti CMV Puro LUC encoding the firefly Luciferase was transfected with Virapower Lentiviral packing mix to 293T cells using lipofectamine 2000. After 48 h, lentiviral supernatant was collected and added into 20-40% confluent PC3 cells. Polybrene (8 µg/ml) was added during the transduction. Two days after transduction, PC3 cells were selected by puromycin at 2 µg/ml concentration. Luciferase expression was analyzed by immunofluorescence staining and western blot. PC3-luc cells were maintained in media containing 1 µg/ml puromycin.

In vitro cytotoxicity and transfection activity of mRNA NP. Cells were seeded at a density of 3~5×10$^4$ cells per well on 24-well plate and allowed to attach and grow until ~80% confluence. Cells were transfected with mRNA NPs at various mRNA concentrations (0.062, 0.125, 0.250, and 0.500 µg/ml) for 16 h followed by washing with fresh complete medium and further incubated for 24 h to check cytotoxicity as well as transfection efficiency. Lipofectamine 2000 (L2K) was used as a standard transfection reagent (according to manufacturer's protocol) to form L2K-mRNA complexes for comparison with the mRNA NPs. Cytotoxicity was measured by AlamarBlue® assay according to the manufacturer's protocol using a microplate reader (TECAN, Infinite M200 Pro). AlamarBlue is a non-toxic assay that allowed us to continuously check real-time cell proliferation. For transection efficiency measurement, cells were harvested with 25% EDTA trypsin and washed two times and resuspended in PBS followed by measuring GFP expression using flow cytometry. The percentages of GFP-positive cells were calculated, and histograms were prepared using Flowjo software.

RNase Protection Assay. To test whether the NPs protected the mRNA from RNase, naked EGFP mRNA and EGFP-mRNA PGCP NPs were incubated in RNase at two mRNA-to-RNase weight ratios (1:1 and 1:10) for 30 min at 37° C., shaking at 100 rpm. A concentration of 0.250 µg/ml EGFP mRNA was used in this study. After incubation, RNase was separated from the EGFP-mRNA PGCP NPs and naked mRNA by washing with water via centrifugation in 100 kDa Amicon filter tubes at 1300 rcf for 10 min. The post RNase-treated EGFP-mRNA PGCP NPs were then diluted in media, while the naked mRNA was complexed with L2K, and the PC3 cells were then transfected as described above and incubated for 16 h. The medium was replaced and incubated for an additional 24 h. The naked EGFP mRNA and EGFP-mRNA PGCP NPs without RNase treatment were used as negative controls. Cells were then harvested to measure EGFP expression by flow cytometry and analyzed using Flowjo as described above.

Mechanism of cellular uptake and endosomal escape of mRNA NPs. To determine the mRNA NPs' uptake and intracellular transport mechanism, 24-well plates were used to seed PC3 cells at an initial density of 5×10$^4$ cells/ml in 1 ml of growth medium and incubated for 24 h at 37° C. in 5% $CO_2$ to allow the cells to attach. The cells were then pre-incubated for 30 min in serum-free medium containing inhibitors (Filipin at 1 µg/ml, CPZ at 10 µg/ml, EIPA at 10 µg/ml, and Baf A1 at 200 nM was used to block caveolae-mediated endocytosis, clathrin-mediated endocytosis, macropinocytosis, and intracellular proton pump inhibitor effects, respectively, alone and in combination). The cells were then transfected with EGFP-mRNA PGCP NPs at mRNA concentration of 0.250 µg/ml. After 16 h, the old medium was replaced with fresh complete medium and incubated for an additional 24 h. The cells were then harvested to check EGFP expression by flow cytometry and analyzed by Flowjo as described above.

Cell growth inhibition assay with PTEN mRNA NP. Cell growth inhibition was determined by CyQUANT assay in 96-well plates. First, 3~5×10$^3$ cells per well per 100 µl were seeded in 96-well plates. The next day, cells were treated with mRNA NP or the L2K-mRNA mixture. After 72 h incubation under standard cell-culture conditions, the culture medium was removed and plates were kept at −80° C. for >24 h. Cells were counted using the CyQUANT kit (Life Technologies) per the manufacturer's instructions. Fluorescence measurements were made using a microplate reader with excitation at 485 nm and emission detection at 530 nm. Cell-growth inhibition was also determined using a 3-(4,5-dimethylthiazol-2-yl)-2,5-diphenyltetrazolium (MTT) bromide assay. Briefly, 3~5×10$^3$ cells were plated in a 96-well plate and treated with NPs the next day. After 16 h, NPs were removed and fresh medium was added. After 72 h of incubation, 10% culture volume of MTT (Sigma Chemicals, St. Louis, Mo.; 5 mg/ml) was added to each well. After incubation for an additional 4 h, 200 µl of isopropanol-HCl solution was added to each well to dissolve the cell pellets. Absorbance was determined using a 96-well SpectraMax plate reader (Molecular Devices, Sunnyvale, Calif.) at 560 nm and 650 nm (background).

Apoptosis assay in vitro. Cells were seeded in 6-well plates until ~80% confluence and then treated with PTEN mRNA NPs. The next day, the NPs were removed (16 h post treatment) and kept in culture for another 24 h. The supernatant and the cell monolayer were collected, washed with PBS, and processed for detection of apoptotic cells using the Annexin V-PE/7AAD apoptosis detection kit (BD Biosciences) according to the manufacturer's instructions.

Western blot assay. Protein extracts were prepared using NP-40 lysis buffer (50 mM Tris-HCl [pH 7.5], 0.5% NP-40 substitute, 150 mM NaCl, and 12.5 mM NaF) supplemented with Complete Mini EDTA-free protease inhibitor tablets (Roche). Equal amounts of protein, as determined with a bicinchoninic acid (BCA) protein assay kit (Pierce/Thermo Scientific) according to the manufacturer's instructions, were separated by SDS-PAGE and transferred to nitrocellulose membranes. The blots were blocked with 5% non-fat dry milk in TBST (50 mM Tris-HCl at pH 7.4 and 150 mM NaCl, and 0.1% Tween 20) and then incubated with appropriate primary antibodies. Signals were detected with horseradish peroxidase-conjugated secondary antibodies and an enhanced chemiluminescence (ECL) detection system (Amersham/GE Healthcare). When indicated, membranes were subsequently stripped for reprobing.

Immunofluorescent staining and microscopy. For immunofluorescent staining, cells were plated onto coverslips in 6-well plates and grown overnight to 60-70% confluence. Cells were washed with ice-cold PBS and fixed with 4% paraformaldehyde (PFA, Electron Microscopy Sciences) in PBS for 15 min at room temperature (RT). Cells were then permeabilized by incubation in 0.2% Triton X-100-PBS for 8 min followed by blocking with PBS blocking buffer containing 2% normal goat serum, 2% BSA, and 0.2% gelatin for 1 h at RT. Then the samples were incubated in primary antibody (1:200 anti-HA rat antibody) for 1 h at RT, washed with PBS, and incubated in goat anti-rat-Alexa Fluor 488 (Molecular Probes) at 1:500 dilution in blocking buffer for 30 min at RT. Finally, stained cells were washed with PBS, counterstained with 500 nM DAPI, and mounted on slides with Prolong Gold antifade mounting medium (Life Technologies).

Animals. Six-week-old BALB/c male normal mice were used for pharmacokinetics (PK) and immune response studies. To evaluate the biodistribution (BioD) of mRNA NP in various organs including tumors and test the therapeutic efficacy of PTEN mRNA NP to suppress tumor growth, male athymic nude mice (6 weeks old) were obtained from Charles River Laboratories. All animal studies were performed under strict regulations and pathogen-free conditions in the animal facility of Brigham and Women's Hospital and in accordance with National Institutes of Health animal care guidelines. The animals had free access to sterile food pellets and water and were kept in the laboratory animal facility with temperature and relative humidity maintained at 23±2° C. and 50±20%, respectively, under a 12-h light/dark cycle. Mice were kept for at least one week to acclimatize them to the food and environment of the animal facility. The animal protocol was approved by the Institutional Animal Care and Use Committees at Harvard Medical School.

Pharmacokinetic (PK) study. For in vivo PK study, healthy BALB/c male mice (6 weeks) were divided into three groups (n=3 per group) and intravenously administered (i) naked Cy5 EGFP mRNA, (ii) Cy5-EGFP-mRNA-PGCP NP or (iii) Cy5-EGFP-mRNA-PGDP NP through the tail vein at a mRNA dose of 700 µg per kg of animal weight. At various predetermined time intervals (0, 5, 15, 30, 60, 120, 180, and 240 min), retro-orbital vein blood was withdrawn using a heparin-coated capillary tube, and the wound was gently pressed for a few seconds to stop the bleeding. Fluorescence intensity of Cy5 was measured at emission and excitation wavelengths of 640 and 670 nm, respectively, using a microplate reader. PK was calculated by calculating the percentage of Cy5 EGFP mRNA in blood at various time periods, normalized with the initial (0 min) time point.

PC3-xenograft tumor model preparation. To prepare the PC3-xenograft tumor mice model, about $4 \times 10^6$ cells in 100 µL of culture medium mixed with 100 µL of matrigel (BD Biosciences) were implanted subcutaneously on the right flank of 6-week-old male athymic nude mice. Mice were monitored for tumor growth every other day according to the animal protocol.

Biodistribution (BioD) of mRNA NP in PCa xenograft tumor model. For the BioD study, PC3 xenograft-bearing male athymic nude mice received intravenous injection of naked Cy5 EGFP mRNA, Cy5-EGFP-mRNA-PGCP NP, and Cy5-EGFP-mRNA-PGDP NP via tail vein injection at an mRNA dose of 700 µg per kg of animal weight. Twenty-four hours later, organs and tumors were harvested and imaged with the IVIS Lumina III In Vivo Imaging System (Perkin Elmer). To evaluate in vivo BioD specifically for PTEN mRNA in a tumor xenograft model, Cy5-tagged PTEN mRNA was prepared by substitution of 25% psedu-UTP with Cy5-UTP when conducting IVT reactions. The Cy5-PTEN-mRNA and its PGCP and PGDP NPs were then injected (i.v. via tail vein) for BioD analysis as described above.

In vivo therapeutic efficacy of PTEN mRNA NP in PCa xenograft tumor model. For in vivo therapeutic efficacy, PGDP NP was used as a delivery system for PTEN mRNA and EGFP mRNA as a negative control. PC3 xenograft-bearing athymic nude mice were treated when the tumors were first palpable. The mice were randomly divided into three groups, which received (i) PBS (n=7), (ii) EGFP-mRNA-PGDP NP (n=9), or (iii) PTEN-mRNA-PGDP NP (n=8). Mice were injected with the above samples via tail vein at a mRNA dose of 700 µg per kg of animal weight at days 10, 13, 16, 19, 22, and 25 after tumor induction. Tumor size was measured using a caliper every three days through day 43, and average tumor volume (mm³) was calculated as: ½(length×width×height). The body weights of the mice were also determined. At day 28 (three days after the last injection), mice (1 mouse for PBS and 2 mice for each EGFP-mRNA-PGDP NP and PTEN-mRNA-PGDP NP group) were selected randomly for harvest of tumors to monitor PTEN expression and tumor cell apoptosis, and various organs to examine in vivo toxicity. The mice were imaged at day 35, and the image backgrounds were removed using Adobe Photoshop software. At day 43, mice were sacrificed and various organs (lung, heart, liver, kidney, and spleen) were collected to assess toxicity by immunohistochemical analysis. Blood serum was also collected at the two time points of days 28 and 43 for hematological assays.

In vivo therapeutic efficacy of PTEN mRNA NPs in advanced PCa models. To assess the in vivo therapeutic efficacy of PTEN mRNA NP in advanced PCa, we prepared two different advanced PCa mice models: (1) an experimental metastasis model employing intravenous inoculation of luciferase-expressing PC3 (PC3-luc) prostate cancer (PCa) cells, and (2) a bone colonization of intratibial (IT) inoculation of PC3-luc cells as an orthotopic model of PCa established metastases. For experimental metastatic PCa model, $2.5 \times 10^6$ PC3-luc cells in 100 μL of PBS were implanted through i.v. tail vein injection into immunocompromised, male athymic nude mice (78 in total). Two weeks after implantation, mice were monitored for tumor growth every three days using an In-Vivo Xtreme imaging system (Bruker) for initial screening of PC3-luc disseminated mice for treatments. Four weeks post tumor inoculation, 24 mice (incidence rate of ~30%) with i.v. disseminated PCa (detected using an In-Vivo Xtreme imaging system [Bruker] after mice were injected intraperitoneally with 150 mg/kg luciferin substrate [PerkinElmer, Catalog #122799]) were randomly divided into three groups (n=8 per treatment group), which received (i) PBS, (ii) EGFP-mRNA-PGDP NP, or (iii) PTEN-mRNA-PGDP NP. To prepare IT orthotopic PCa model, immunocompromised, male athymic nude mice were anesthetized with isoflurane, and $5 \times 10^4$ PC3-luc cells in 10 μL of PBS were injected in tibiae of each mouse (40 mice [80 tibae] in total). Note that the establishment of IT orthotopic PCa model had a ~90% success rate. The mice were then randomly divided into the above three groups (n=12 mice [n=24 tibae] per treatment group) and treatments were started next day (considered as day 0) post tumor cell inoculation. Treatments were performed via i.v. tail vein injection at mRNA dose of 700 μg per kg of animal weight. Initial treatment was performed at day 0, followed by another four injections in every three days (in total, five injections). Tumor images were also obtained every three days using an In-Vivo Xtreme imaging system (Bruker) as mentioned above, using a charge-coupled device (CCD) camera (exposure time 30 sec, binning of 1, field of vision [FOV] of 19 cm, f/stop of 1.10, and no filter). Regions of interest (ROI) were quantified as average radiance (photon/ $sec/cm^2/sr$) using Bruker MI SE software, and the fold change of ROI in each measurement (day 3, 6, 9, 12 and 15) was compared to day 0 of the same tibia and plotted using GraphPad software (Version 7). The body weights of the mice were also determined every three days and plotted using GraphPad software (Version 7).

Immunohistochemical staining to detect in vivo PTEN expression. The expression of HA-PTEN protein in tumor tissue section was assessed by immunohistochemistry. Sections (5 μm thick) were obtained from tumors treated with PBS, PTEN-mRNA-PGDP NP, or EGFP-mRNA-PGDP NP. Paraffin-embedded sections were deparaffinized, rehydrated, and washed in distilled water. Samples were then incubated for 20 min with 0.3% hydrogen peroxide ($H_2O_2$) at room temperature to quench endogenous peroxidase activity followed by antigen retrieval in citrate buffer (pH 6.0) using a microwave for 10 min (2 times, each time 5 min). After washing with PBS (pH 7.4), the samples were treated with the Avidin/Biotin Blocking kit (Vector) to quench endogenous biotin, and then immersed in blocking buffer (1% BSA, 5% normal goat serum) for 60 min. Tissue sections were then incubated with primary rabbit anti-HA antibody at 4° C. overnight in a humid chamber. After being rinsed with PBS, the samples were incubated with biotinylated secondary antibody for 30 min at room temperature, followed by incubation with the avidin-biotin-horseradish peroxidase complex (ABC kit, Vector Laboratories, Inc). Staining was developed with the diaminobenzidine peroxidase substrate kit (Impact DAB, Vector Laboratories, Inc) for 3 min. Sections were then counterstained with hematoxylin (Sigma), dehydrated, and mounted.

TUNEL apoptosis assay. Tumors were extracted and fixed in formalin, embedded in paraffin, and sectioned at a thickness of 5 μm. Tumor cell apoptosis was determined by terminal deoxynucleotidyl transferase-mediated deoxyuridine triphosphate nick-end labeling (TUNEL) assay (In Situ Cell Death Detection Kit, TMR red; Roche, #12-156-792-910) according to the manufacturer's protocol. DAPI stain was used to assess total cell number.

In vivo toxicity evaluation: hematologic examination, histology, and immune response. To evaluate in vivo toxicity, blood was drawn retro-orbitally and serum was isolated from PC3 xenograft athymic nude mice three days after the final injection (day 28), and at the end of the efficacy experiment (day 43). Aspartate aminotransferase (AST), alanine aminotransferase (ALT), blood urea nitrogen (BUN), creatinine, and troponin-1 were measured using assay kits for AST (BioVision), ALT and Creatinine (Cayman Chemical), BUN (Arbor Assays), and troponin-1 (Life Diagnostics) according to the manufacturers' protocols. For histological examination, various organs (lung, heart, liver, kidney, and spleen) were also collected three days after the final NP injection (day 28), and at the end point of the experiment (day 43). The organs were then fixed with 4% paraformaldehyde and embedded in paraffin followed by sectioning (34 μm) and staining with H&E. The slides were assessed using an EVOS Cell Imaging System (Thermo Fisher Scientific). Next, to check immunological response, male Balb/c immunocompetent male mice (n=3) received intravenous injection of PBS, naked PTEN mRNA (700 μg mRNA per kg), empty PGDP NP, and PTEN-mRNA PGDP NP. Six or twenty-four hours post injection, serum samples were collected and processed to measure the representative cytokine (i.e., TNF-α) by enzyme-linked immunosorbent assay (ELISA) (Affymetric eBioscience) according to the manufacturer's protocol.

Statistical analysis. All graphs were prepared using GraphPad Prism 7 software, and statistical analysis was also carried out using GraphPad Prism 7 software to perform One-Way ANOVA or Mann-Whitney test. Mann-Whitney tests were performed for experiments in which the data was determined to be nonparametric by the normality test[75-77] (i.e., for both disseminated metastatic and IT orthotopic experiments). All experiments were performed in triplicate unless otherwise stated. Error bars indicate standard deviation (SD), unless otherwise noted specifically as standard error means (SEM). A P<0.05 value is considered statistically significant, where all statistically significant values shown in various Figures are indicated as: *P<0.05, P<0.01, *P<0.001, and ****P<0.0001.

Example 1. Preparation and Characterization of mRNA NP

Figure 1B:
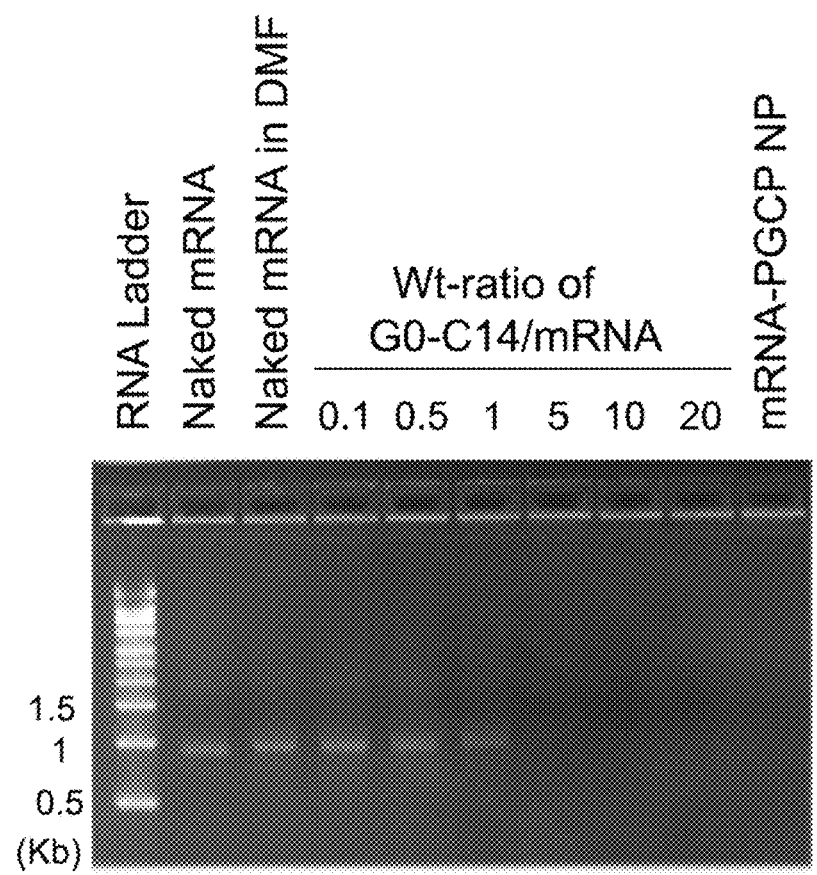
FIG. 1B. Preparation and characterization of mRNA NP. Agarose gel electrophoresis assay of mRNA stability in organic solvent, naked or complexed with cationic G0-C14, at various weight ratios (from 1~20). The formulated mRNA PLGA/G0-C14/ceramide-PEG (PGCP) NP was also run through gel to detect any mRNA leaching from the NP. About 0.125 µg of EGFP-mRNA was used for all groups in this assay.
Figure 1C:
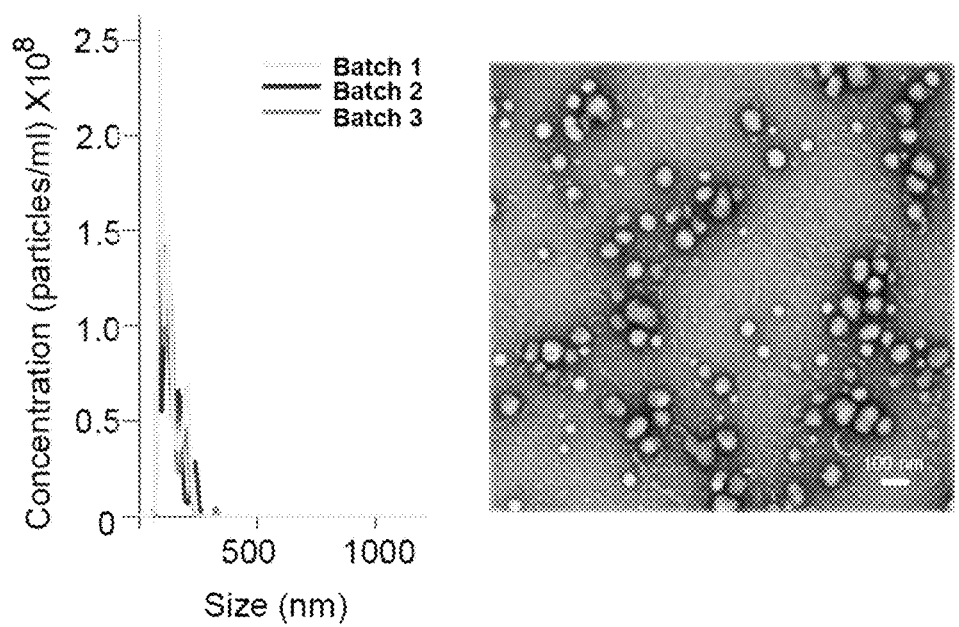
FIG. 1C. Preparation and characterization of mRNA NP. The mRNA-PGCP NP was characterized with NanoSIGHT to check size distribution (n=3 batches, 121.5±2.3 nm), and transmission electron microscopy (TEM) to observe morphology. A weight ratio of 1:15 for mRNA: G0-C14 was used for the NP preparation.
Figure 1D:
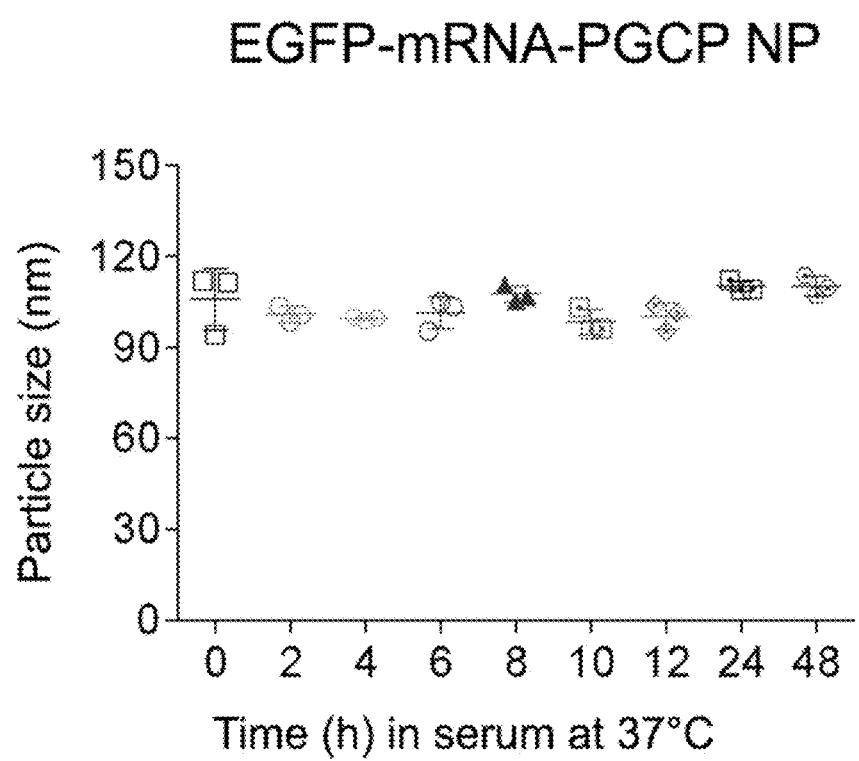
FIG. 1D. Preparation and characterization of mRNA NP. Stability of mRNA-PGCP NP in 10% serum condition at 37° C. was evaluated by measuring particle size changes determined with NanoSIGHT at various time points up to 48 h (mean±SD, n=3).

A robust self-assembly approach was employed to prepare the hybrid mRNA NPs using the cationic lipid-like compound G0-C14 and poly(lactic-co-glycolic acid) (PLGA) polymer coated with a lipid-poly(ethylene glycol) (lipid-PEG) shell[45] (FIG. 1A). G0-C14 was used for mRNA complexation, and PLGA, a widely clinically used biodegradable and biocompatible polymer, was used to make a stable NP core. EGFP mRNA was used as a model mRNA, and the EGFP mRNA NP coated with ceramide-PEG is herein referred as to EGFP-mRNA-PGCP NP. We observed no effect of organic solvent (DMF) on the integrity or stability of EGFP mRNA, whether naked, complexed with G0-C14, or encapsulated in NPs (FIG. 1B). FIG. 1B also shows that G0-C14 effectively condensed EGFP mRNA at a weight ratio of 5 or above. The NPs were prepared at a G0-C14/mRNA weight ratio of 15, with no leaching of mRNA shown by electrophoresis, suggesting that most mRNA was encapsulated. The hybrid EGFP-mRNA-PGCP NPs were ~120 nm in size and spherical, as characterized by NanoSIGHT and transmission electron microscopy (TEM), respectively (FIG. 1C). Essential to the hybrid NP, the solid PLGA polymer core allowed formation of a stable and rigid nanostructure. The average surface charge measured by dynamic light scattering (DLS) was near neutral (5.96±0.76 mV), since the NPs have an outer lipid-PEG shell. In addition, the serum stability test showed no obvious changes in the particle size over 48 h, suggesting the stability of the EGFP-mRNA-PGCP NPs (FIG. 1D).

Figure 9C:
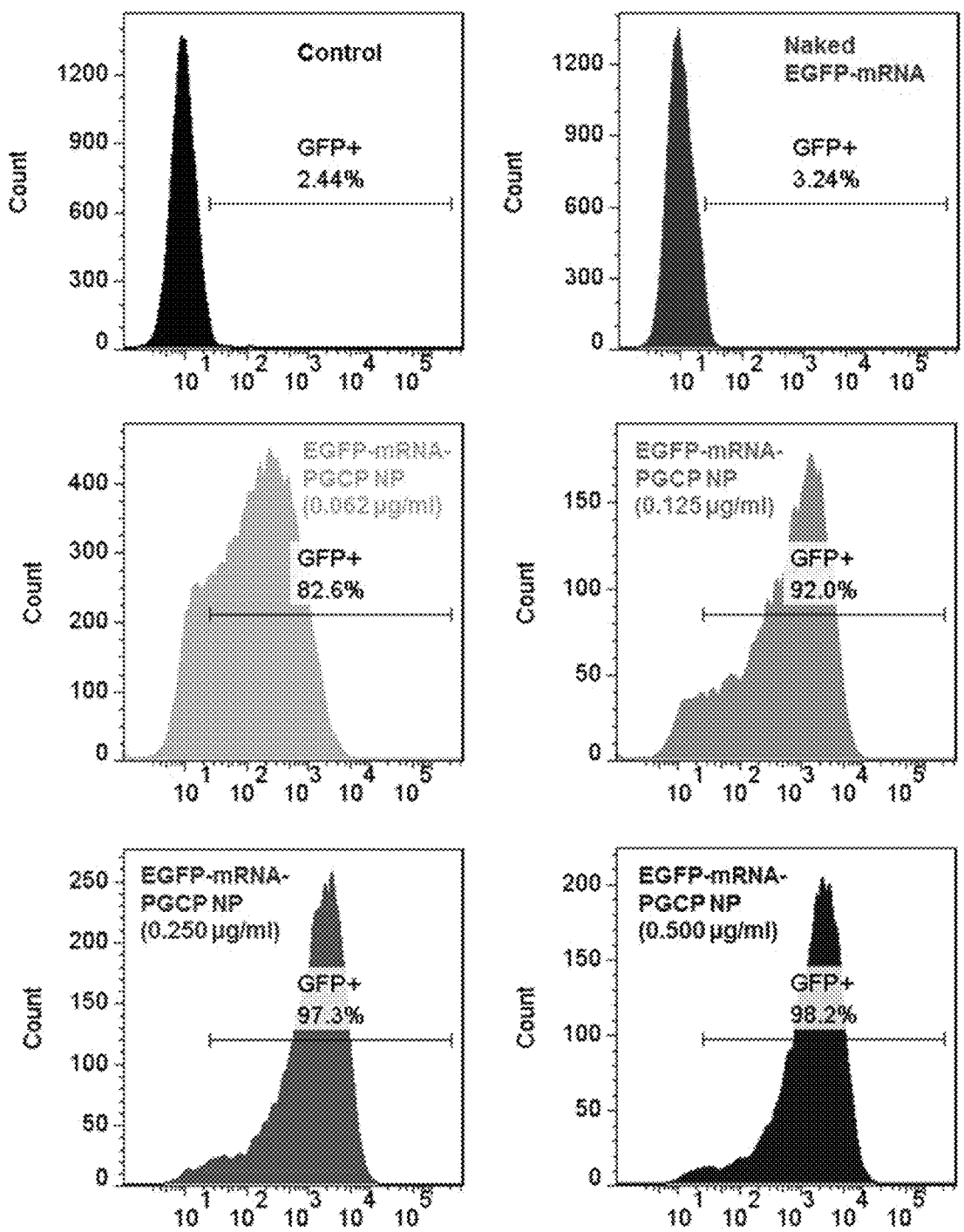
FIG. 9C. The histograms for the respective groups were generated after analysis using Flowjo software.
Figure 10A:
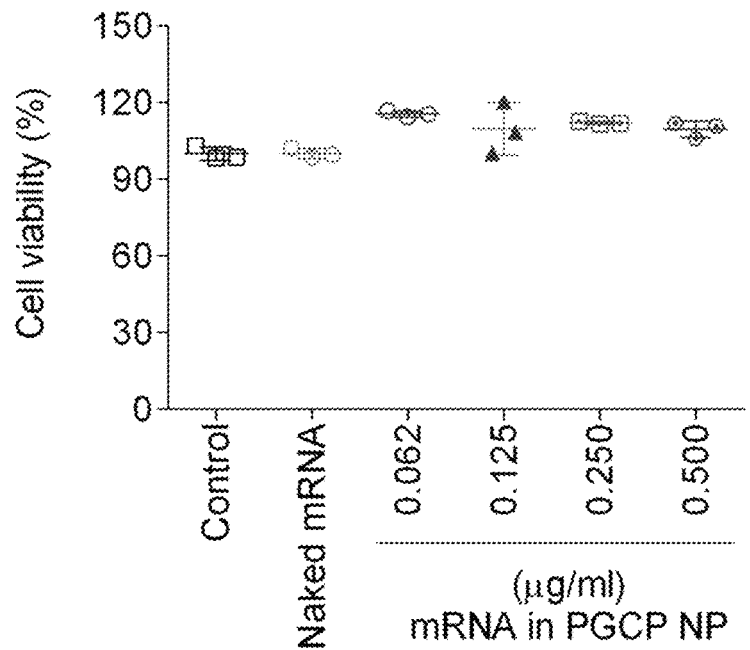
FIG. 10A. In vitro toxicity and transfection efficiency of mRNA NP in LNCaP cells. The cells were treated with various mRNA concentrations (at 0.062, 0.125, 0.250, 0.500 μg/mL) of EGFP-mRNA-PGCP NP. AlamarBlue cytotoxicity assay. The cell viability percentages were normalized with the untreated control group (mean±SD, n=3).

Example 2. mRNA NPs Exhibit Low Cytotoxicity and Potent Transfection Efficiency In Vitro, and Protect mRNA Activity from RNase Degradation To evaluate in vitro cytotoxicity, cells were treated with EGFP-mRNA-PGCP NPs for 16 h and further incubated with fresh culture medium for 24 h; nearly 80% of PC3 cells were still viable at the highest EGFP mRNA concentration of 0.5 µg/ml (FIG. 2a). AlamarBlue toxicity assay was further extended for DU145 and LNCaP cells with no notable reduction in cell viability, maintaining ~90-100% viable cells at various EGFP mRNA concentrations from 0.062 to 0.5 µg/ml in DU145 cells and 100% cell viability at all concentrations in LNCaP cells (FIG. 9A and FIG. 10A, respectively).

Figure 2B:
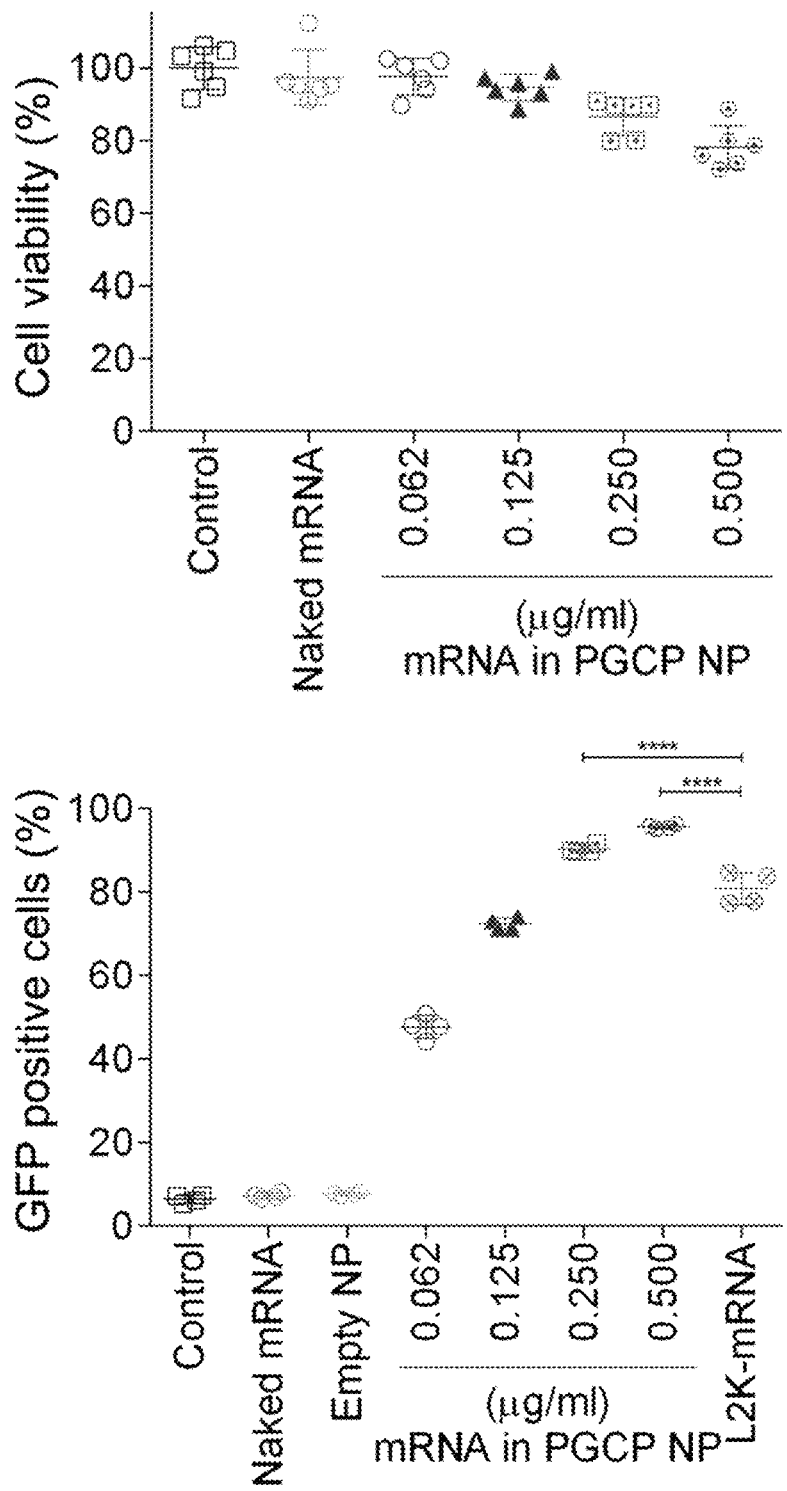
FIG. 2B. In vitro toxicity and transfection efficiency of mRNA NPs in PC3 cells. Transfection efficiency (% GFP positive cells) was determined using flow cytometry (mean±SD, n=4, ****P<0.0001)
Figure 2C:
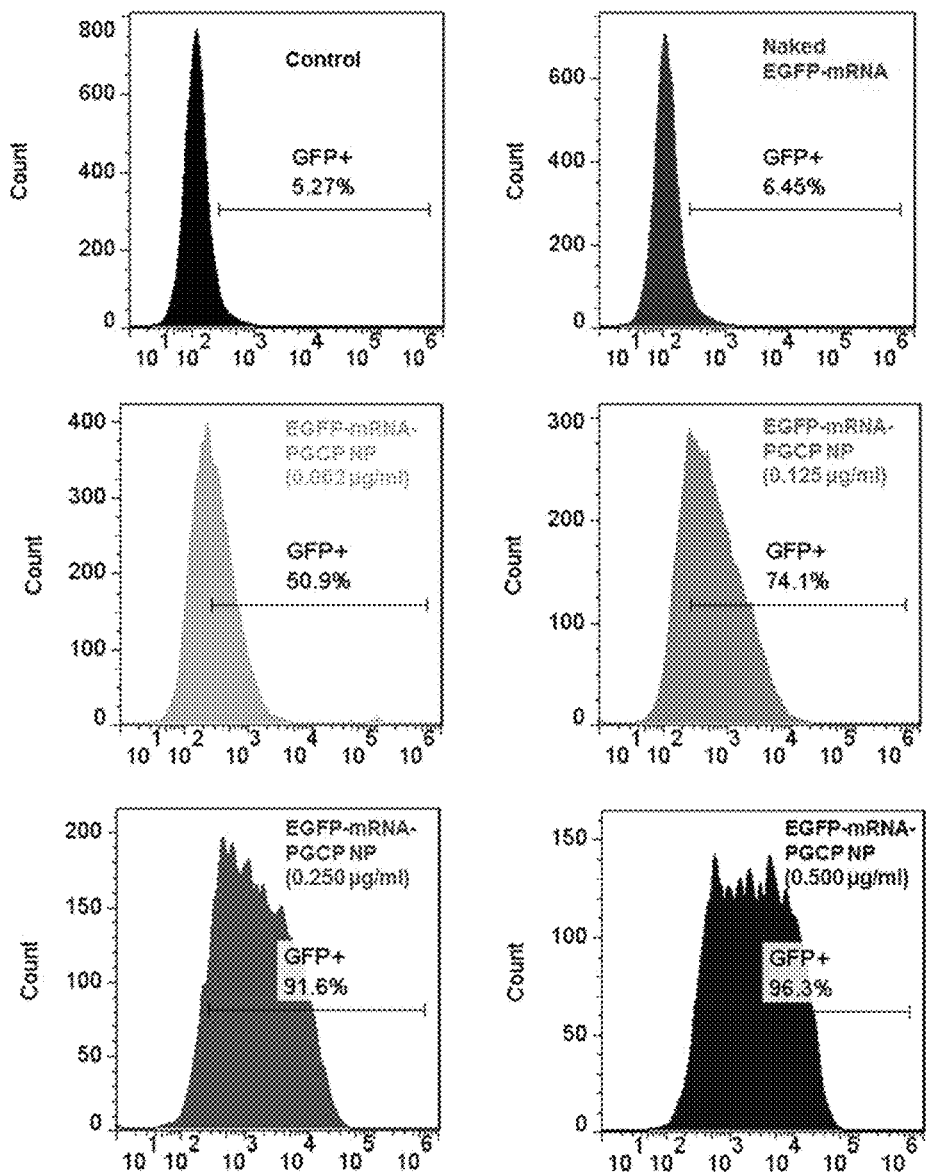
FIG. 2C. In vitro toxicity and transfection efficiency of mRNA NPs in PC3 cells. Transfection efficiency was analyzed with the histograms for the respective groups using Flowjo software FIG. 2D. In vitro toxicity and transfection efficiency of mRNA NPs in PC3 cells. Fluorescence microscopy images of PC3 cells transfected with naked EGFP mRNA, EGFP-mRNA-PGCP NP, and Lipofectamine 2000 (L2K)-EGFP-mRNA (magnification at 20×).
Figure 2D:
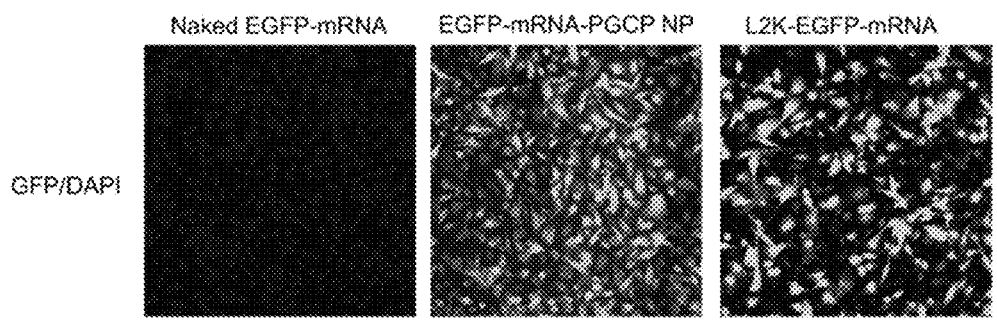
FIG. 2A. In vitro toxicity and transfection efficiency of mRNA NPs in PC3 cells. Cells were treated with various mRNA concentrations (at 0.062, 0.125, 0.250, 0.500 µg/mL) of EGFP-mRNA-PGCP NPs for 16 h and further incubated for 24 h in standard cell culture incubation conditions. AlamarBlue cytotoxicity assay; cell viability was normalized with the untreated control group (n=6 per group).
FIG. 2E. In vitro toxicity and transfection efficiency of mRNA NPs in PC3 cells. Mechanism of cellular uptake and endosomal escape of mRNA NPs in PC3 cells. The cells were pre-incubated for 30 min in serum-free medium containing inhibitors (Filipin, CPZ, EIPA, and BafA1 were used as the inhibitor for caveolae-mediated endocytosis, clathrin-mediated endocytosis, macropinocytosis, and intracellular proton pump effects, respectively) or combinations of inhibitors (Filipin, CPZ, or EIPA mixed with Baf A1) prior to transfection with EGFP-mRNA PGCP NPs at mRNA concentration of 0.250 µg/ml. Transfection efficiency (% GFP positive cells) was determined using flow cytometry (mean±SD, n=5, *P<0.001 and **P<0.0001).
FIG. 2F. In vitro toxicity and transfection efficiency of mRNA NPs in PC3 cells. The mechanism of cellular uptake and intracellular transport of the hybrid mRNA NPs is schematically illustrated.
Figure 10B:
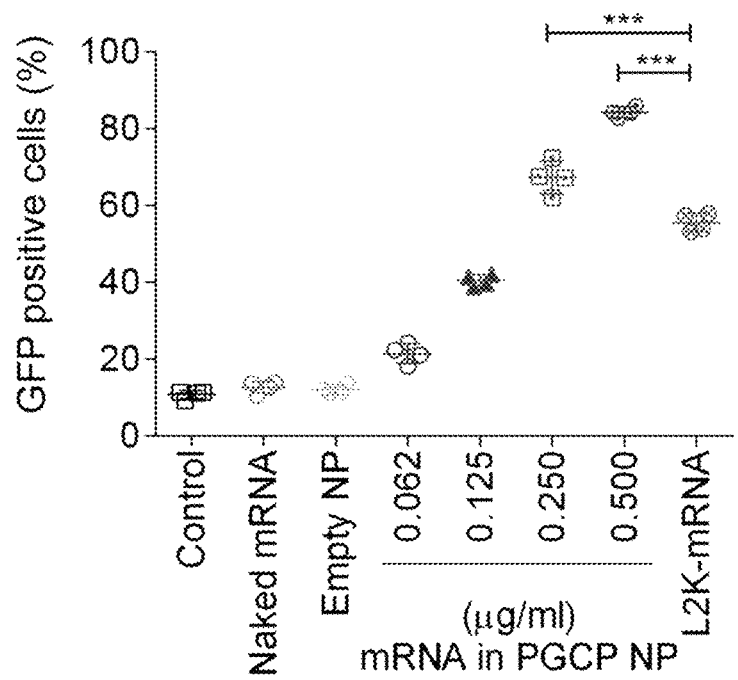
FIG. 10B. Transfection efficiency percentages were determined using flow cytometry (mean±SD, n=4, ***P<0.001).
Figure 10C:
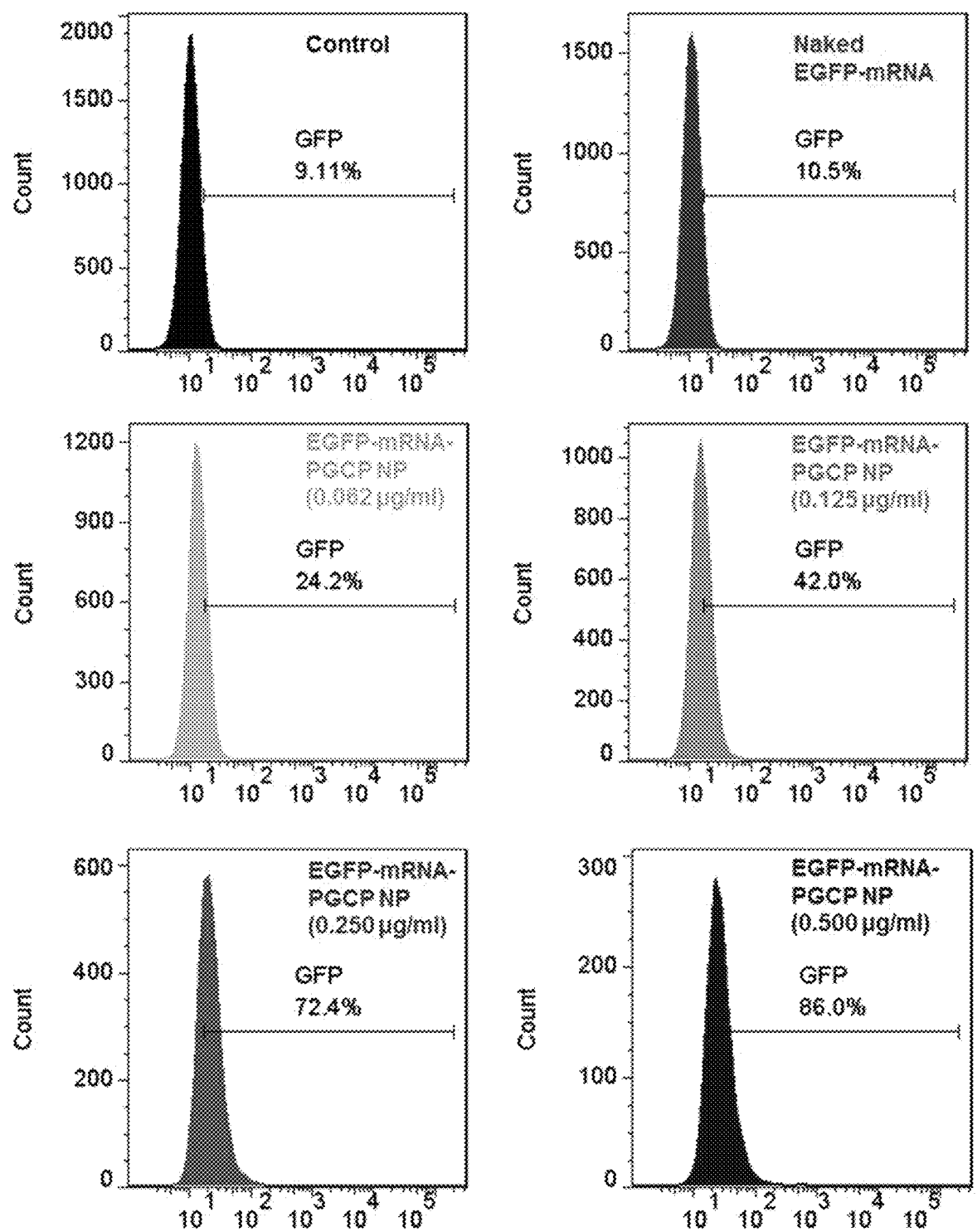
FIG. 10C. The histograms for the respective groups were generated after analysis using Flowjo software.

We next examined transfection efficacy in vitro. The EGFP-mRNA-PGCP NP mediated highly efficient transfection of PC3 cells, showing a dose-dependent linear increase of EGFP expression correlated with increasing EGFP mRNA concentrations (from 0.062 to 0.5 µg/ml) (FIG. 2B,C). The transfection efficacy (in terms of percentile of EGFP-positive cells) of the NPs at mRNA concentrations of 0.25 and 0.5 µg/ml was demonstrably greater than that mediated by the commercial transfection agent lipofectamine 2000 (L2K) at mRNA concentration of 0.5 µg/ml. This high transfection activity was confirmed by confocal microscopy (FIG. 2D), although L2K-mRNA-transfected PC3 cells exhibited a slightly higher fluorescent intensity. We found similar highly effective transfection activity of EGFP-mRNA-PGCP NPs in two other PCa cell lines (DU145 and LNCaP); >98% and 86% efficiency at the 0.5 µg/ml concentration, respectively (FIG. 9B,C and FIG. 10B,C). While the transfection activity of our mRNA NP was comparable to that of L2K-mRNA in DU145 cells, the NP group showed significantly greater transfection efficacy relative to L2K-mRNA in LNCaP cells, especially at EGFP mRNA concentrations of 0.25 and 0.5 µg/ml.

Figure 11A:
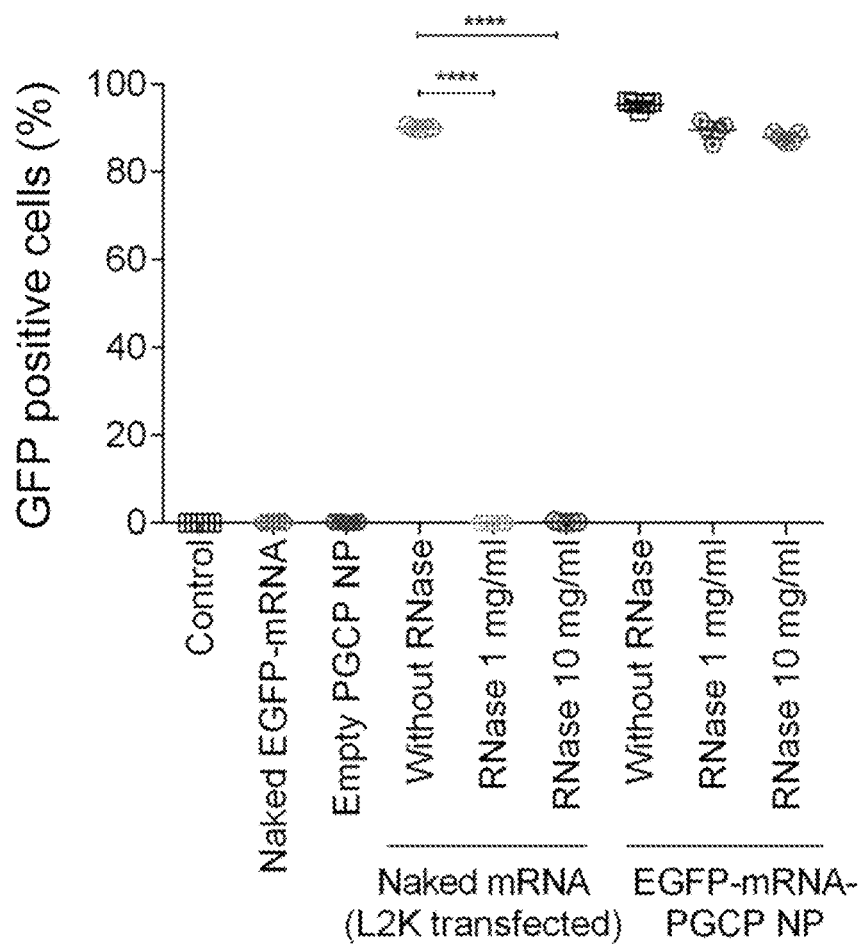
FIG. 11A. The effect of RNase on the activity of mRNA NPs. Transfection efficiency percentages of naked mRNA (complexed with L2K) and EGFP-mRNA-PGCP NPs in the presence of two RNase concentrations (1 mg/ml and 10 mg/ml) were determined using flow cytometry (mean±SD, n=4, ****P<0.0001).
Figure 11B:
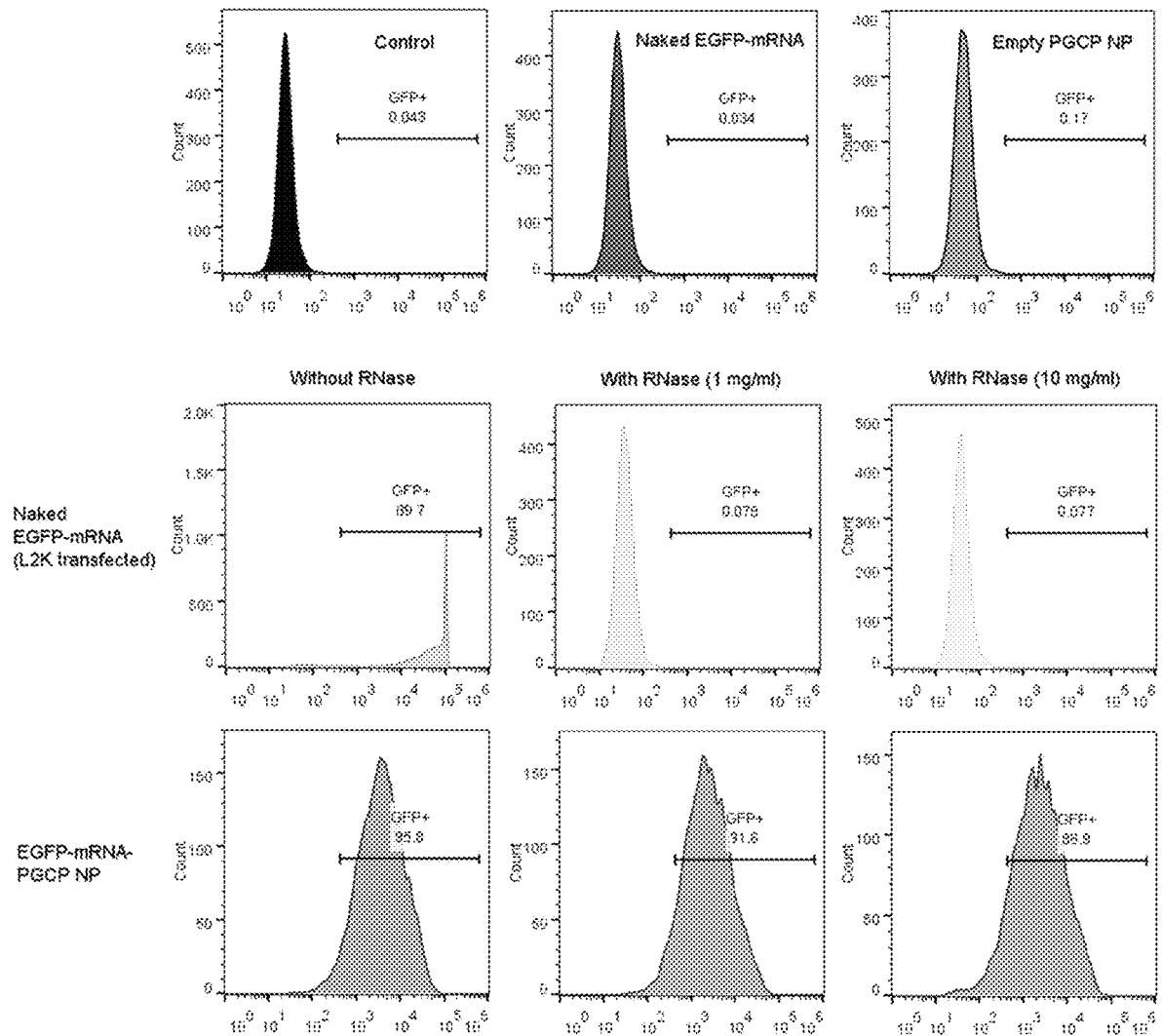
FIG. 11B. The histograms for the respective groups were generated after analysis using Flowjo software.

To investigate the ability of the NPs to protect mRNA from RNase degradation, we incubated EGFP-mRNA-PGCP NP at two ratios of mRNA to RNase weight (1:1 and 1:10) for 30 min and then evaluated transfection activity in PC3 cells. A concentration of 0.250 µg/ml EGFP mRNA was used. Naked EGFP mRNA (without or with RNase incubation) complexed with L2K was used as a control. The transfection of naked EGFP mRNA (without RNAse incubation) complexed with L2K showed ~85% efficiency, whereas transfection was drastically reduced to <0.1% (similar to untreated control) in the RNase-treated groups. In contrast, EGFP-mRNA-PGCP NP notably maintained the integrity and activity of the mRNA at both RNase concentrations, consistently showing ~90% transfection capacity, comparable to the transfection in the absence of RNAse (FIG. 11A,B).

Example 3. Mechanisms of Cellular Uptake and Endosomal Escape of mRNA NPs

Figure 2E:
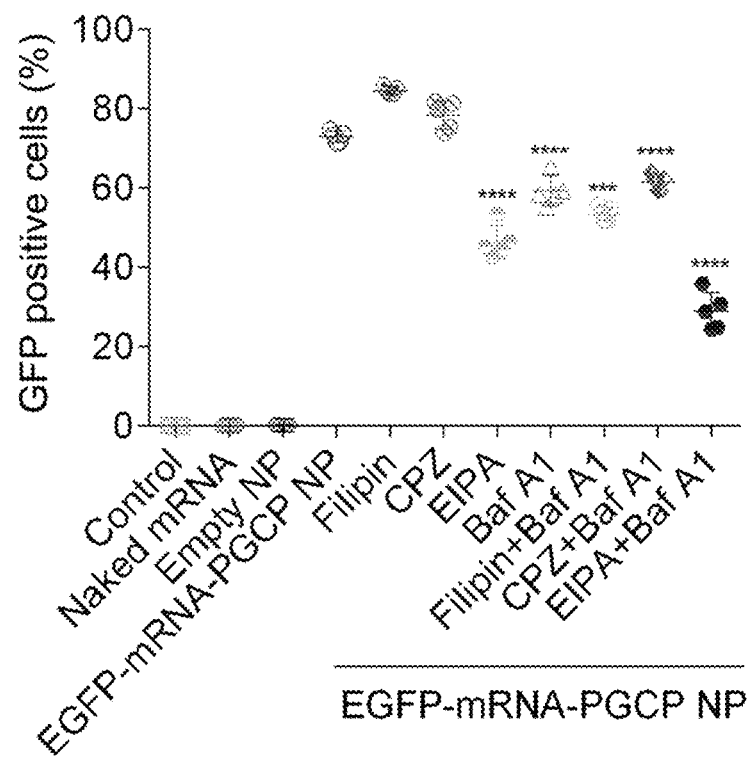
Figure 2F:
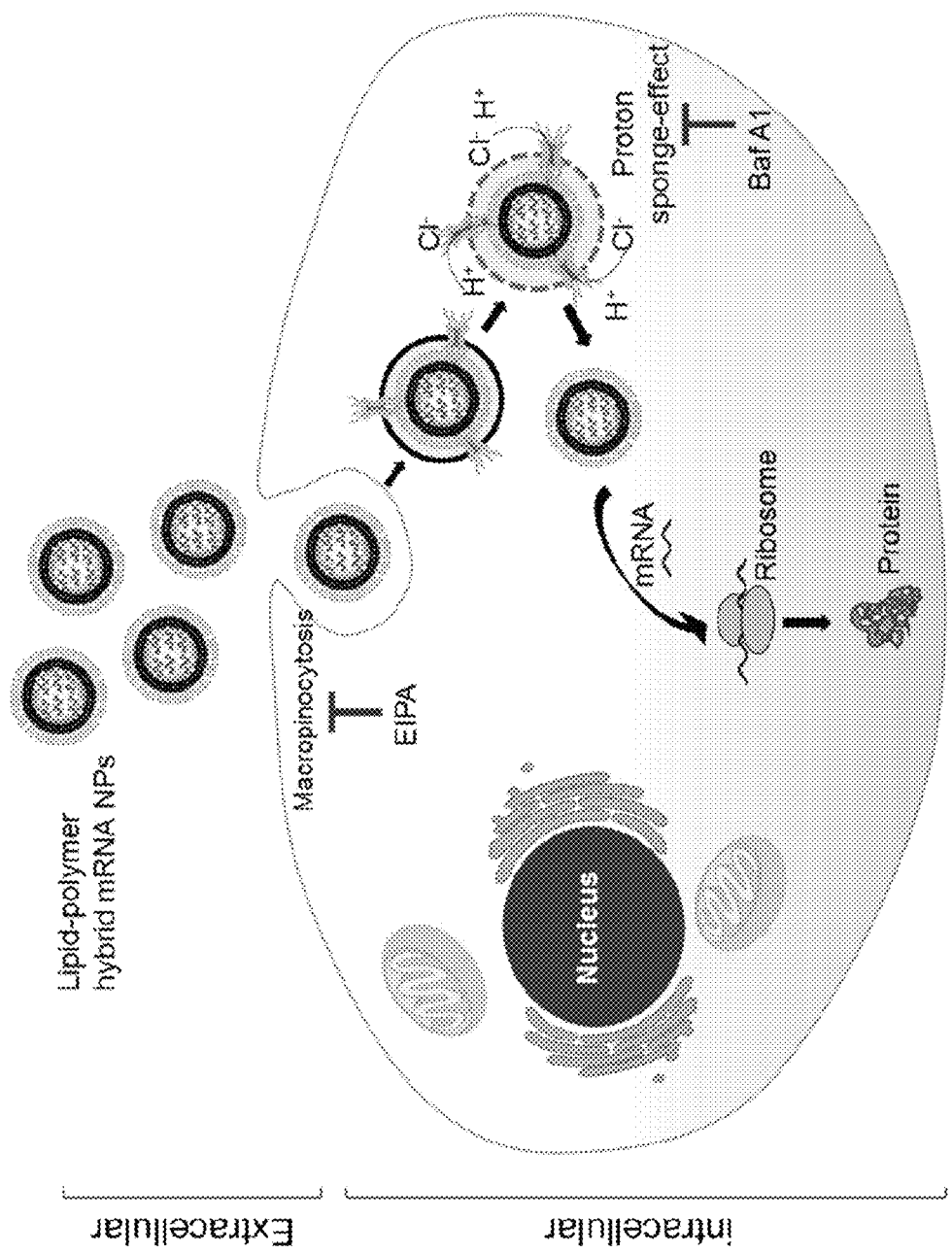

To evaluate the cellular uptake mechanisms and intracellular transport of mRNA NPs, we studied the transfection efficiency of EGFP-mRNA-PGCP NPs in PC3 cells pretreated with different inhibitors. NP transfection was not affected by either caveolae- or clathrin-mediated inhibitors (Filipin and CPZ, respectively). In contrast, uptake was significantly decreased from ~80% (without inhibitor) to ~40% in the presence of EIPA, a macropinocytosis inhibitor. Transfection of mRNA NPs was also markedly decreased from ~80% (without inhibitor) to ~58% in the presence of the proton-pump inhibitor Bafilomycin A1 (Baf A1)[46, 47]. We further tested transfection activity using combinations of Filipin, CPZ, or EIPA with Baf A1. Filipin+Baf A1 and CPZ+Baf A1 exhibited low transfection efficiency similar to Baf A1 alone, whereas EIPA+Baf A1 showed a combinatorial effect, exhibiting superior inhibition of transfection activity (FIG. 2E,F). These results suggest that cellular internalization of the EGFP-mRNA-PGCP NP is partly mediated by macropinocytosis, and after entering into the cells, the NPs were able to induce a proton-sponge effect to release the cargo cytosolically. All the above inhibitors are used commonly to investigate the cellular uptake/transport pathways of NP[45-47]. The results thus suggest that this combinatorial cellular uptake and endosomal escape mechanism, together with mRNA's inherent properties, could constitute one potential advantage of this mRNA delivery system.

Example 4. Functional NP Delivery of PTEN mRNA to PTEN-Null PCa Cells In Vitro

Figure 12A:
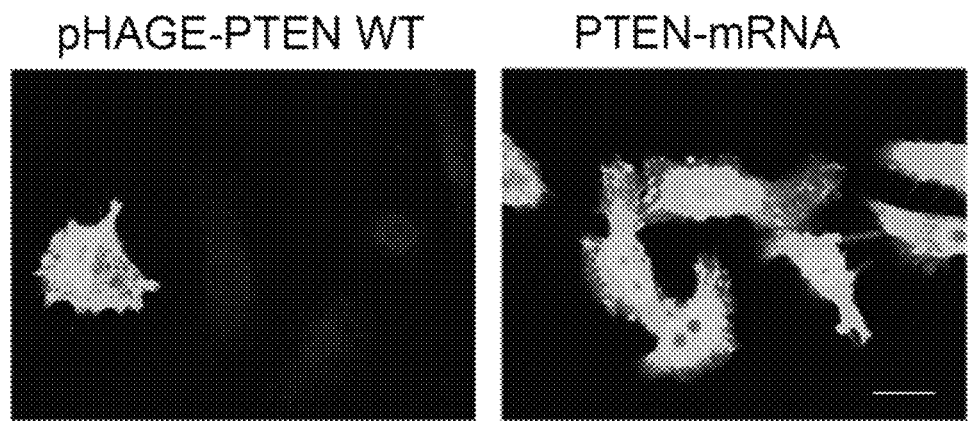
FIG. 12A. The effect of PTEN-mRNA in PC3 cells transfected by Lipofectamine 2000 (L2K). Immunofluorescence staining of HA-PTEN expression in cells after transfection with PTEN mRNA or pHAGE-PTEN WT.
Figure 12B:
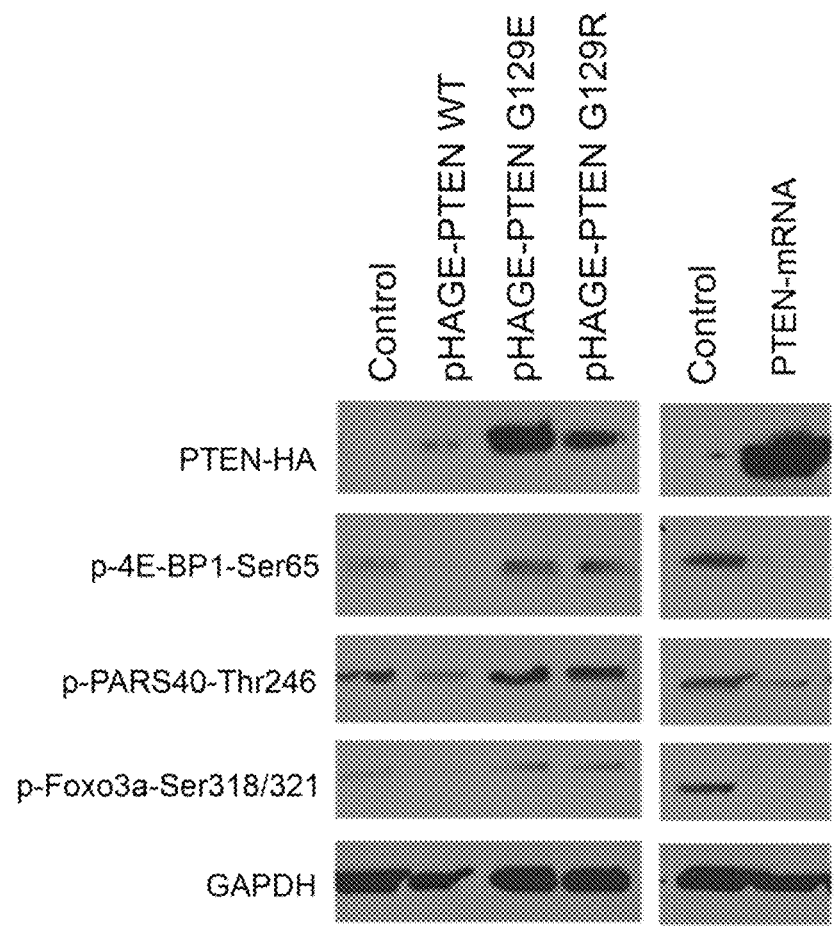
FIG. 12B. Downregulation of PI3K-AKT pathway after treatment with PTEN mRNA.
Figure 12C:
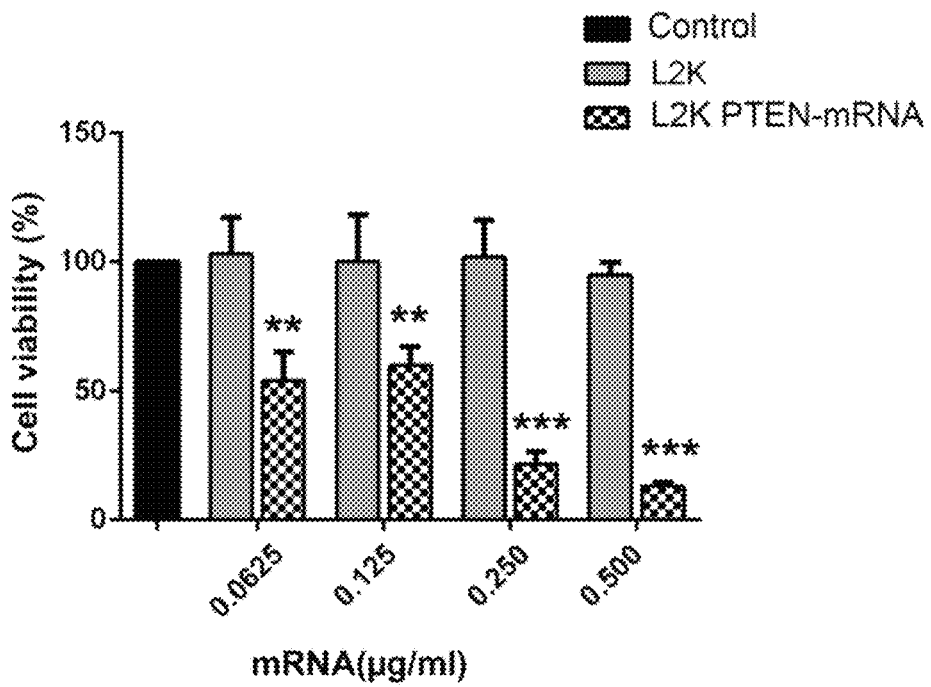
FIG. 12C. Cell viability of PC3 cells after PTEN mRNA treatment determined by CyQUANT assay (mean±SD, n=3, P<0.01 and *P<0.001).

We prepared PTEN mRNA by in vitro transcription (IVT) as previously described[48, 49]. PTEN mRNA was modified with ARCA capping and enzymatic polyadenylation and was fully substituted with Pseudo-UTP, 5'-Methyl-CTP, followed by DNase and phosphatase treatment. Substitution with Pseudo-UTP and 5'-Methyl-CTP in replacement of regular UTP and CTP was applied to reduce mRNA immunostimulation.[43, 49, 50] The PTEN mRNA was also hemagglutinin (HA)-tagged to ensure easy detection and separation from endogenous message. We first transfected PTEN mRNA into PTEN-null PCa (PC3) cells using L2K to assess the facilitation of protein expression, diminish cancer cell viability, and suppress the PI3K-AKT pathway. PC3 cells transfected with L2K-PTEN-mRNA showed markedly higher PTEN-HA expression than pHAGE-PTEN WT (MSCV-N-Flag-HA-IRES-PURO gateway destination vector with long terminal repeat [LTR]-driven expression of PTEN wildtype) by immunofluorescence staining (FIG. 12A). Western blotting also showed that PTEN-HA expression was significantly higher than plasmid PTEN transfection. The difference in Akt-Ser473 level between empty PGCP NP and PTEN-mRNA-PGCP NP was masked by relatively high background levels of Akt-Ser473 generated by growth factors contained in fetal bovine serum. However, when compared to the basal level of Akt-Ser473 in serum starvation conditions, there was a significant decrease in Akt-Ser473 levels when PTEN-mRNA-PGCP NPs were added to induce PTEN expression. Furthermore, PTEN mRNA treatment downregulated the PI3K-AKT pathway, showing decreased in phosphorylation of 4E-BP1-Ser65, PARS40-Thr246, and Foxo3a-Ser318/321 as determined by western blotting (FIG. 12B). Accordingly, PTEN mRNA NP treatment dramatically decreased cell viability as measured by CyQUANT assay (FIG. 12C).

Figure 3A:
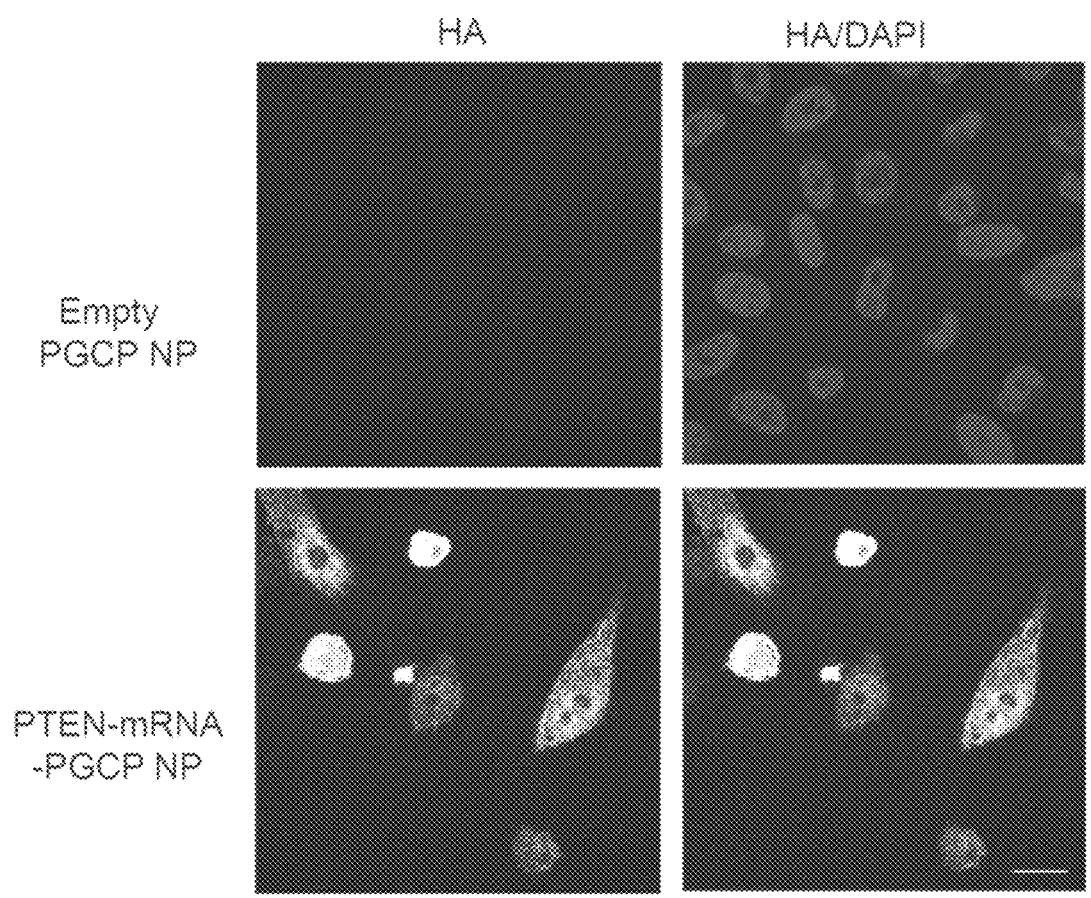
FIG. 3A. In vitro mechanism of PTEN-mRNA-PGCP NP treatment in PC3 cells and its therapeutic effect. Immunofluorescence staining of HA-PTEN after empty PTEN NP and PTEN-mRNA-PGCP NP treatment.
Figure 3B:
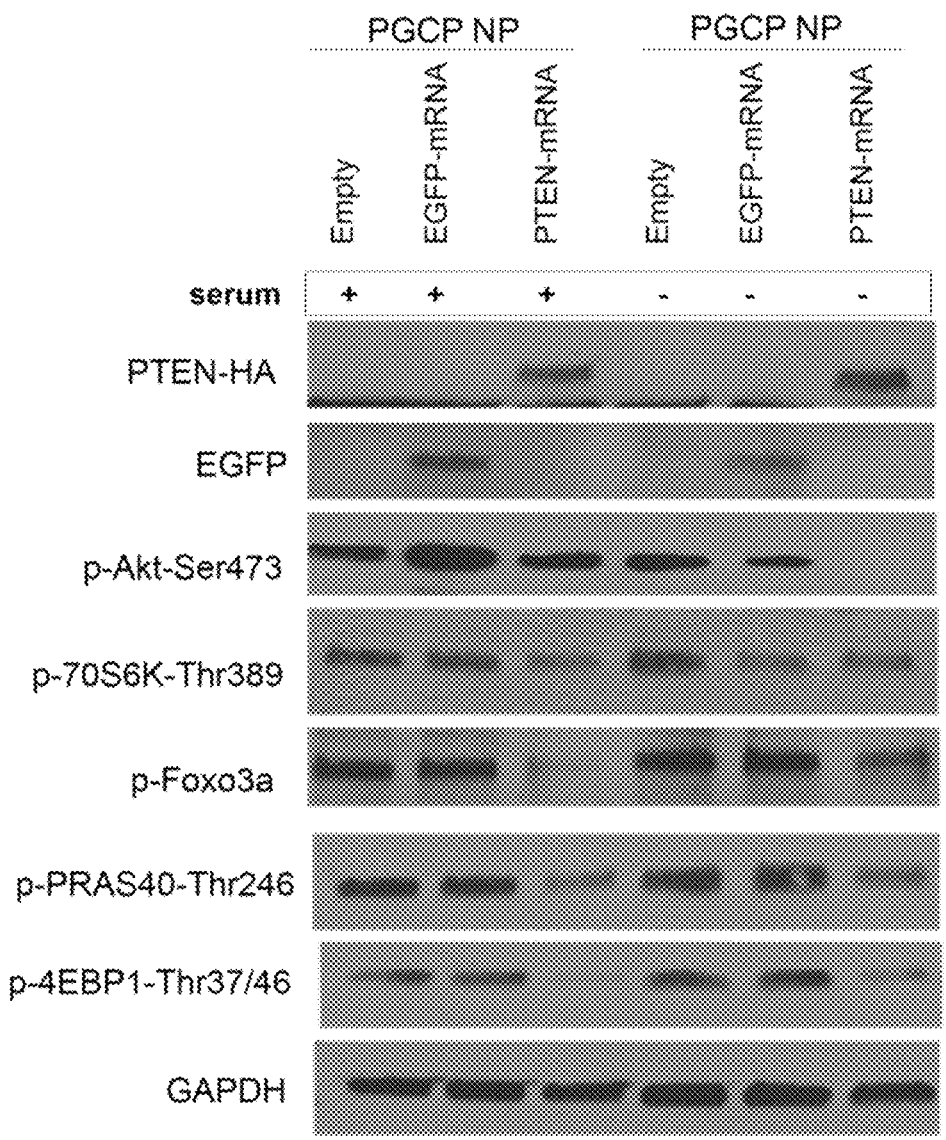
FIG. 3B. In vitro mechanism of PTEN-mRNA-PGCP NP treatment in PC3 cells and its therapeutic effect. Western blot analysis of PI3K-AKT pathway signaling after mRNA-PGCP NP treatment in the presence (+) or absence (−) of serum.
Figure 3C:
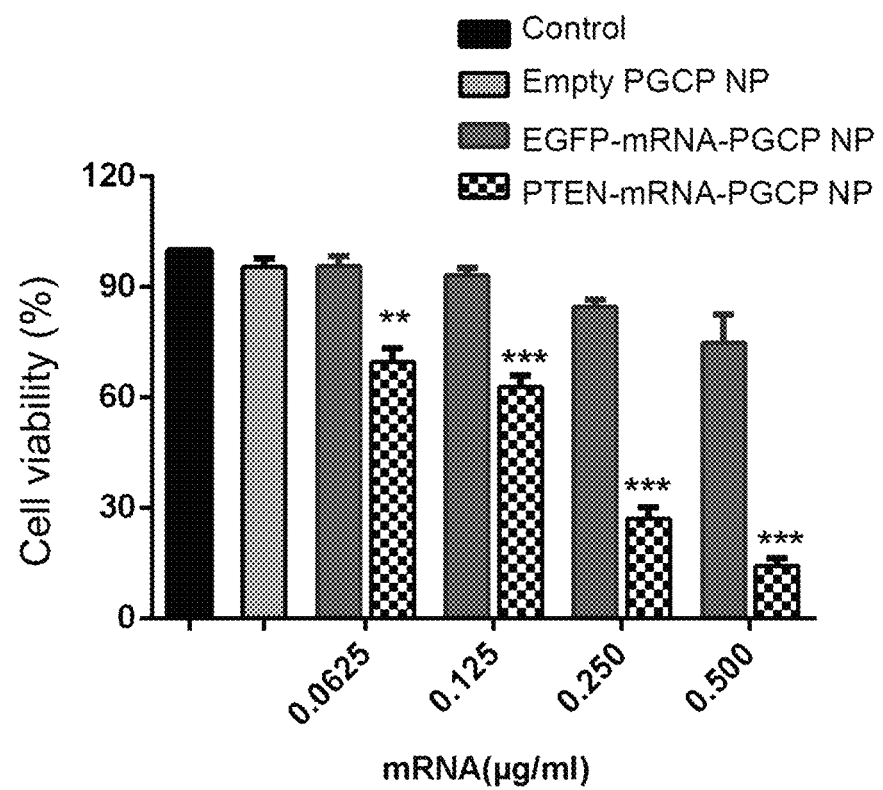
FIG. 3C. In vitro mechanism of PTEN-mRNA-PGCP NP treatment in PC3 cells and its therapeutic effect. The percent cell viability of PC3 cells after treatment with empty PGCP NP, EGFP-mRNA-PGCP NP, or PTEN-mRNA-PGCP NP measured by MTT assay (mean±SD, n=3, P<0.01 and *P<0.001).
Figure 3D:
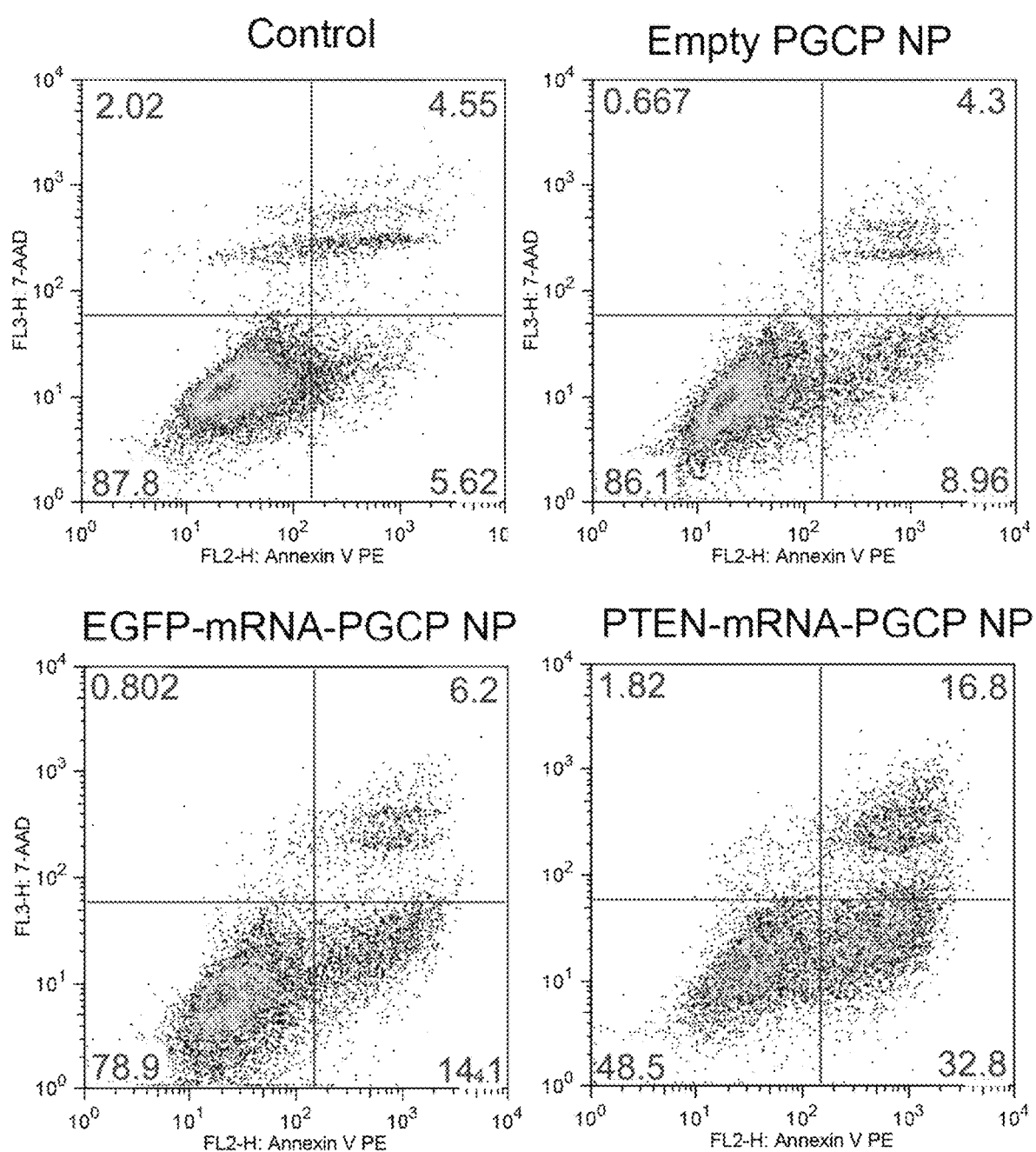
FIG. 3D. In vitro mechanism of PTEN-mRNA-PGCP NP treatment in PC3 cells and its therapeutic effect. Apoptosis was determined by flow cytometry after empty PGCP NP, EGFP-mRNA-PGCP NP, or PTEN-mRNA-PGCP NP treatment of PC3 cells.

Next, we applied the NP platform optimized above to determine whether our PTEN-mRNA-PGCP NP could restore the therapeutic functionality of tumor-suppressor PTEN to PCa cells. Both immunofluorescence staining (FIG. 3A) and western blot (FIG. 3B) confirmed the restoration of PTEN-HA expression transduced by PTEN-mRNA-PGCP NP treatment. It is worth noting that since PTEN-mRNA-PGCP NP treatment reduced cell viability, the cell density of this group was considerably lower than that of the group treated with control empty PGCP NP (FIG. 3A). Next, PTEN-mRNA-PGCP NP treatment significantly decreased cell viability in a dose-dependent manner compared to both empty PGCP NP and EGFP-mRNA-PGCP NP groups, as measured by MTT assay (FIG. 3C). We further found that after 48 h treatment, PTEN-mRNA-PGCP NP efficiently inhibited PI3K-AKT signaling as indicated by the greater decrease in phosphorylation of Akt-Ser473, p70S6K-Thr389, 4E-BP1-Thr37/46, PARS40-Thr246, and Foxo3a-Ser318/321. PTEN-mRNA-PGCP NP treatment also reduced basal phosphorylation of the above proteins under serum-starvation conditions (FIG. 3B). Moreover, early apoptosis was increased after treatment with PTEN-mRNA-PGCP NP, as indicated by elevated numbers of Annexin-V-positive cells via flow cytometry (FIG. 3D). A ~4-fold increase in cell death was noted in PC3 cells after PTEN-mRNA-PGCP NP treatment relative to control empty PGCP NP. We also noticed a slight increase in apoptosis in the EGFP-mRNA-PGCP NP-treated group; this was in part a possible consequence of inducing exogenous RNA into PC3 cells. However, this effect was very modest in comparison to the increase in apoptosis observed with the PTEN-mRNA-PGCP NP group. These results indicate that our mRNA NP platform has the potential to effectively deliver PTEN mRNA and restore functional PTEN activity to tumor cells.

Figure 13A:
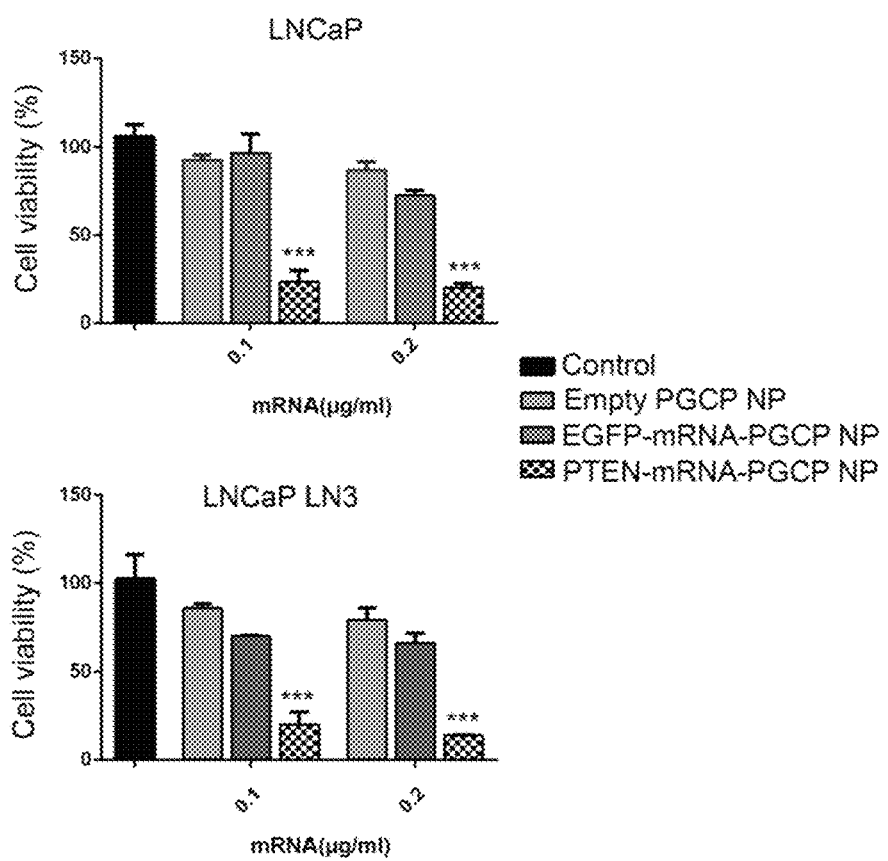
FIG. 13A. In vitro therapeutic effect of PTEN-mRNA-PGCP NP in LNCaP prostate cancer cells. Cell viability of LNCaP and its invasive subclone LNCaP LN3 cells after empty PGCP NP, EGFP-mRNA-PGCP NP, or PTEN-mRNA-PGCP NP treatment, measured by MTT assay (mean±SD, n=3, ***P<0.001).
Figure 13B:
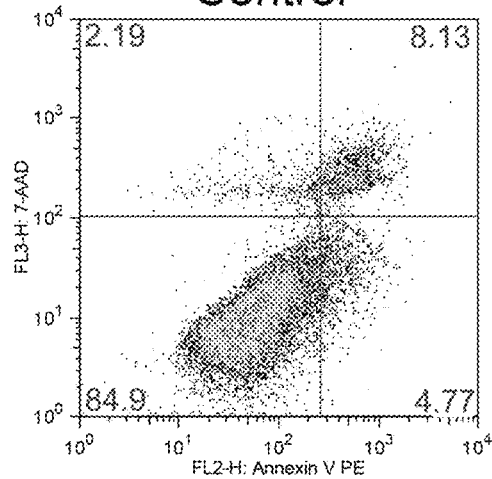
FIG. 13B. Apoptosis assay of LNCaP cells after empty PGCP NP, EGFP-mRNA-PGCP, or PTEN-mRNA-PGCP NP treatment.
Figure 13B:
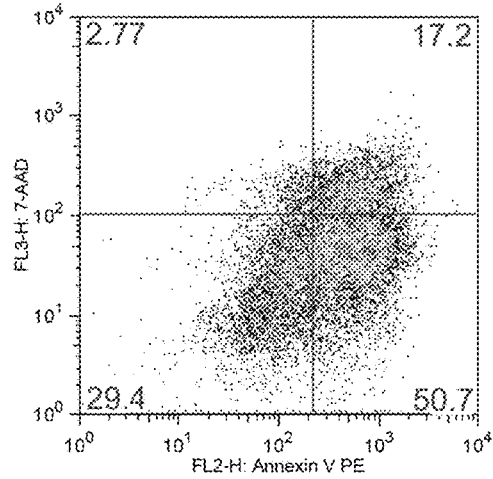
Figure 13B:
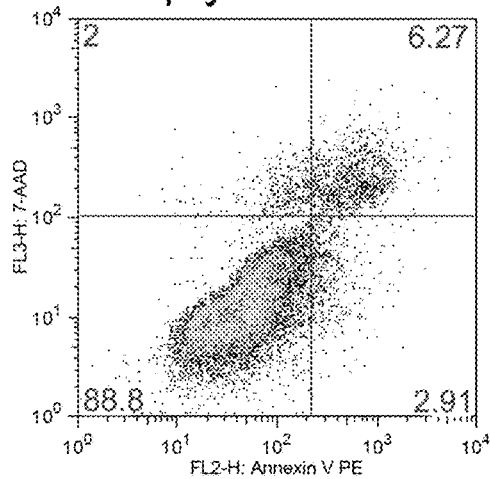
Figure 13B:
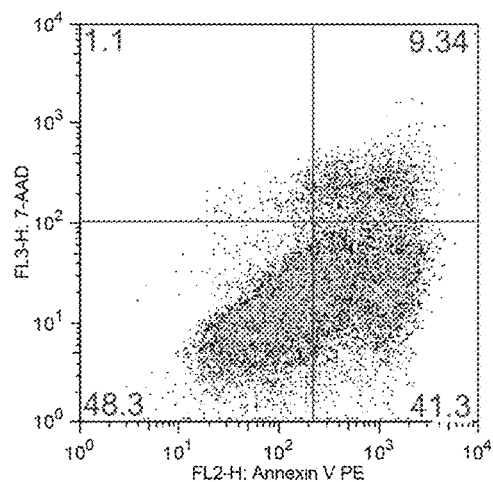
Figure 14A:
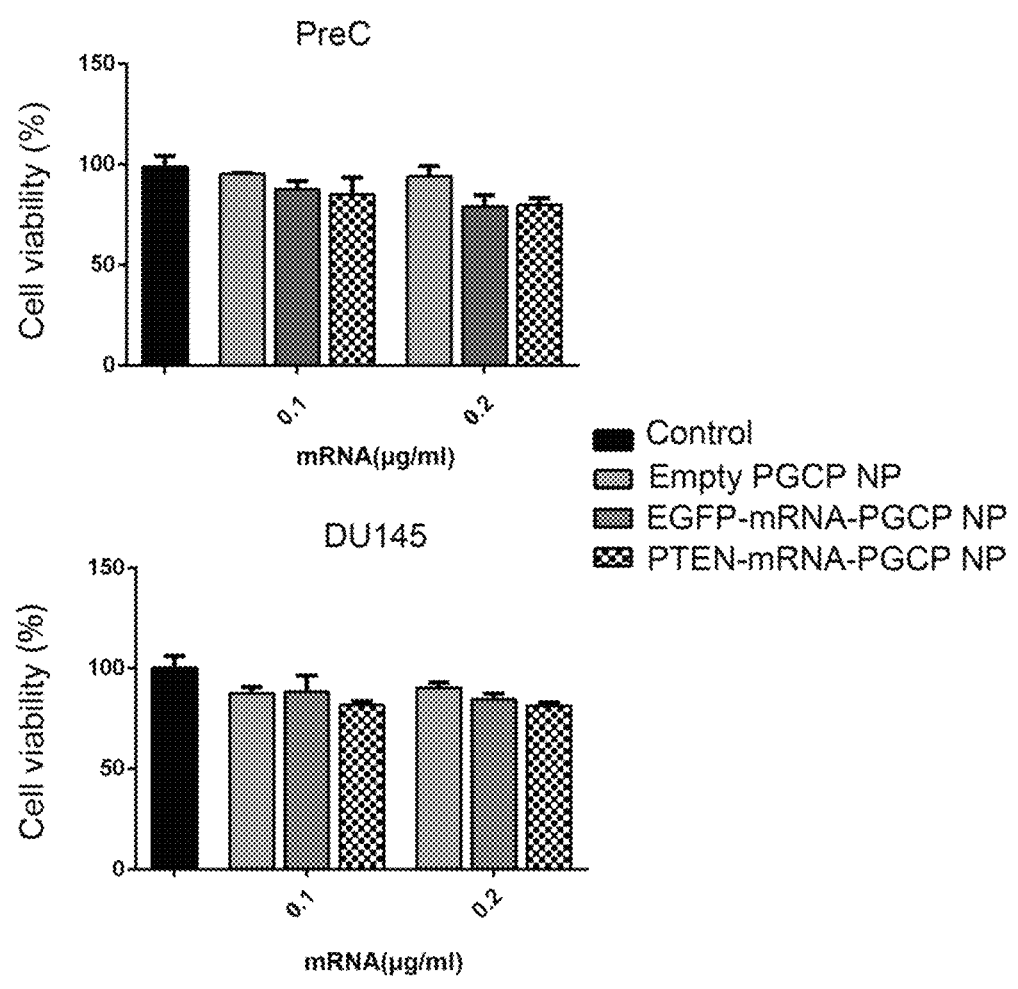
FIG. 14A. In vitro therapeutic effect of PTEN-mRNA-PGCP NP in prostate epithelial cells (PreC) and DU145 prostate cancer cells. Cell viability of PreC and DU145 cells after empty PGCP NP, EGFP-mRNA-PGCP, or PTEN-mRNA-PGCP NP treatment measured by MTT assay.
Figure 14B:
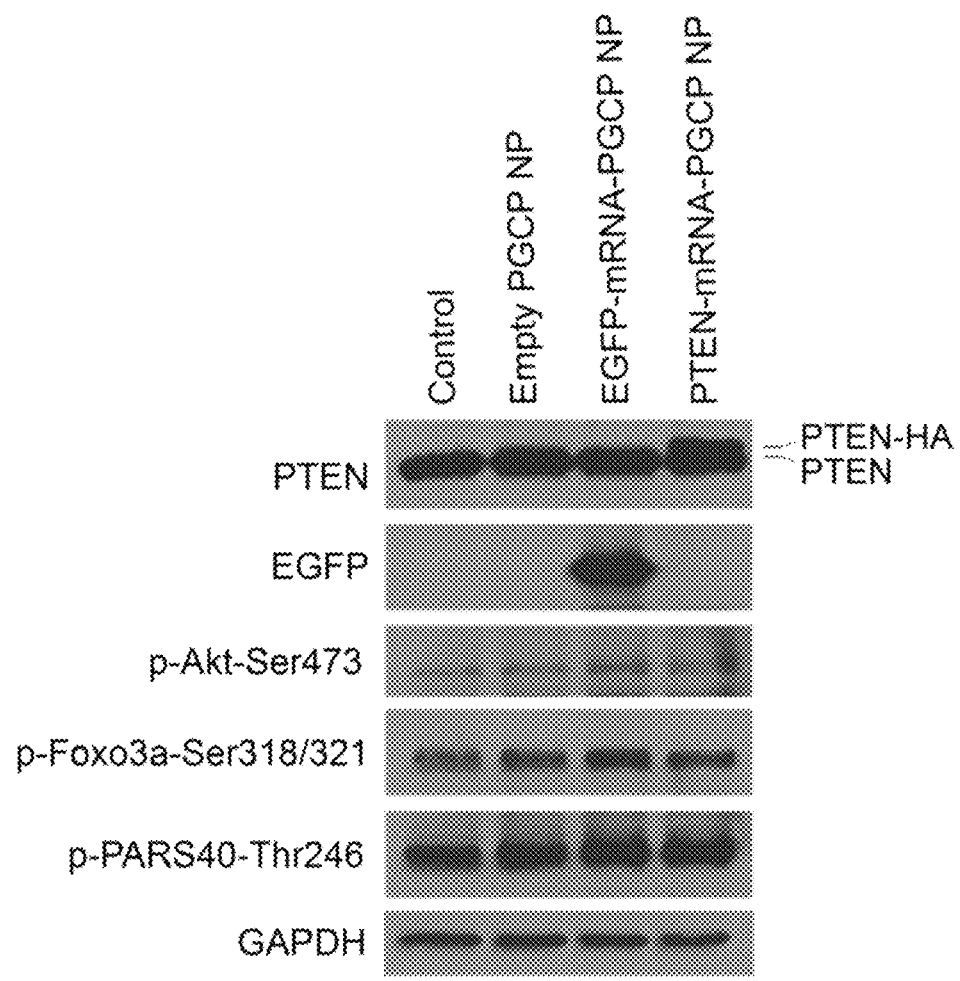
FIG. 14B. Western blot analysis of PI3K-AKT pathway in DU145 cells under different PGCP NP treatment conditions.
Figure 15A:
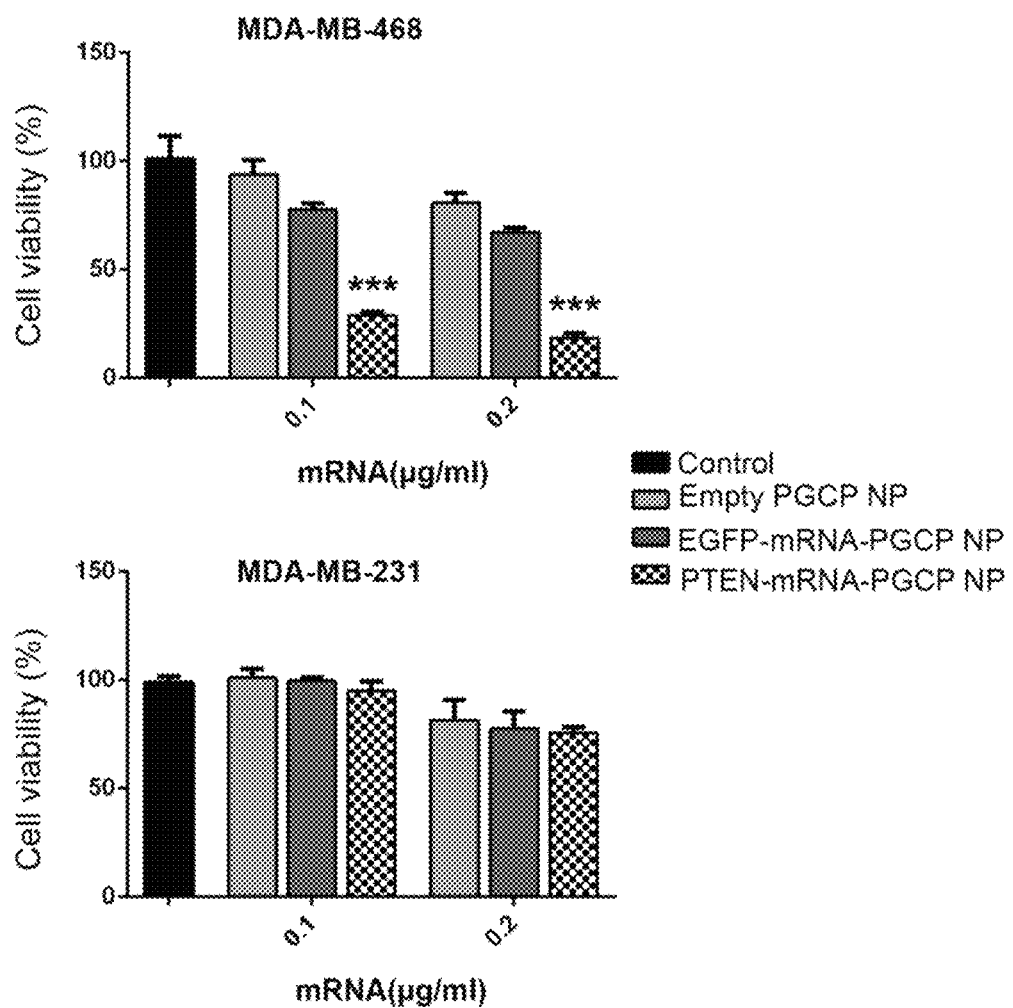
FIG. 15A. In vitro therapeutic validation of PTEN-mRNA-PGCP NP in MDA-MB-468 and MDA-MB-231 breast cancer cells. Cell viability of MDA-MB-468 and MDA-MB-231 cells after empty PGCP NP, EGFP-mRNA-PGCP NP, or PTEN-mRNA-PGCP NP treatment measured by MTT assay (mean±SD, n=3, ***P<0.001).
Figure 15B:
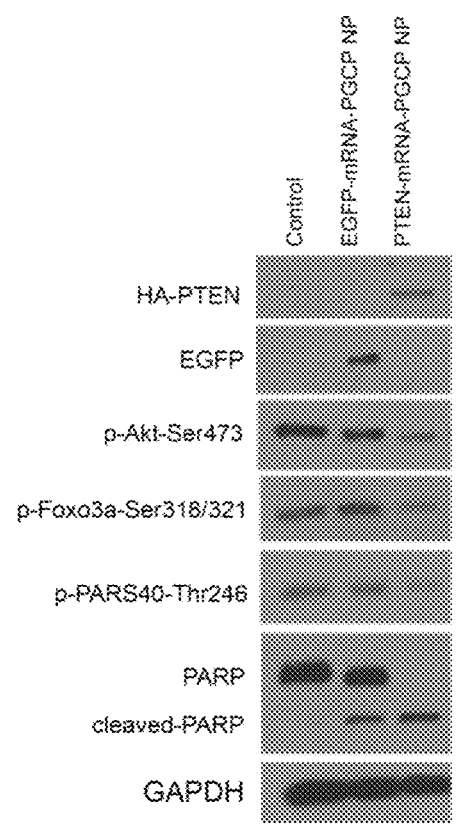
FIG. 15B. Western blot analysis of PI3K-AKT pathway signaling.
Figure 15C:
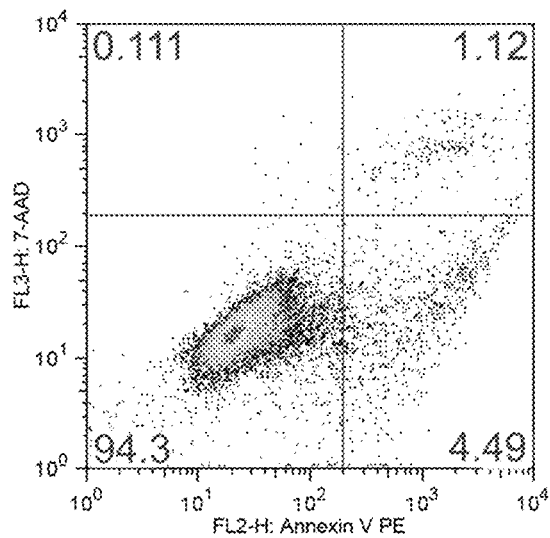
FIG. 15C. Apoptosis assay of MDA-MB-468 cells after empty, EGFP-mRNA, or PTEN-mRNA-PGCP NP treatment.
Figure 15C:
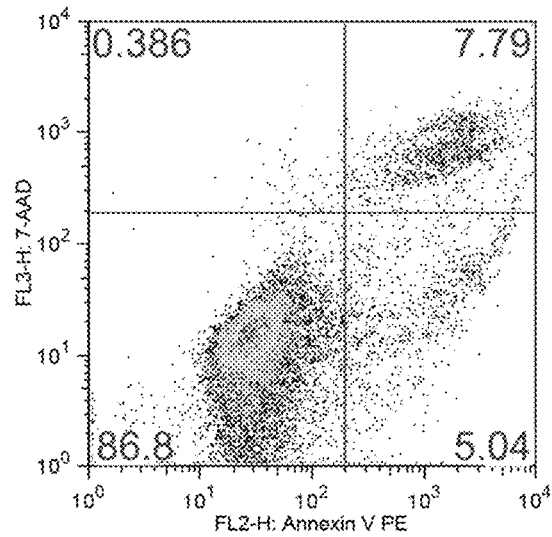
Figure 15C:
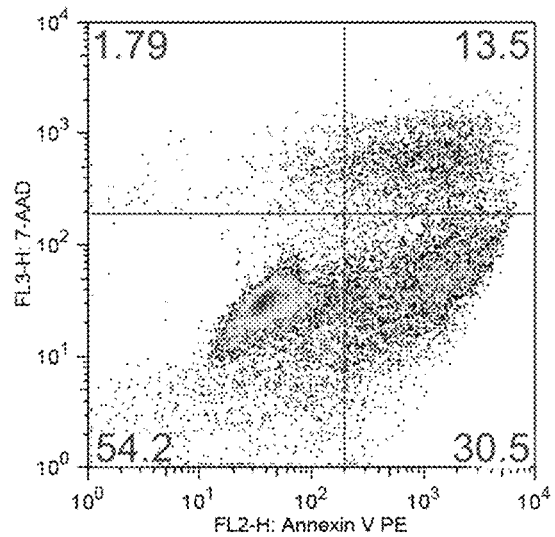

Consistent with the above results, PTEN-mRNA-PGCP NP treatment remarkably reduced the cell viability of androgen receptor (AR)-positive PCa LNCaP cells as well as the invasive LNCaP LN3 subclone, both PTEN-deficient (FIG. 13A). Cell apoptosis was also increased in LNCaP cells by PTEN-mRNA-PGCP NP treatment relative to empty PGCP NP or EGFP-mRNA-PGCP NP control groups (FIG. 13B). In contrast, delivery of PTEN-mRNA with our PGCP NP into normal prostate epithelial cells (PreC) or to PTEN-competent DU145 cells did not significantly affect cell viability (FIG. 14A), nor was there any significant change in PI3K-AKT signaling (FIG. 14B). This is consistent with earlier results[51] showing that PTEN[+/−] DU145 was refractory to conventional transfection with PTEN plasmid and suggests that restoration of PTEN may most effectively suppress growth and survival of tumor cells with defective PTEN expression. Similar to the results with PCa cells, PTEN-mRNA-PGCP NP treatment restored PTEN protein and growth-suppressive activity in PTEN-null MDA-MB-468 breast cancer cells, with treated cells showing reduced cell viability and PI3K-AKT signaling as well as induced apoptosis via PARP cleavage and Annexin V staining. PTEN-competent MDA-MB-231 cells showed no effect on those phenotypes after PTEN-mRNA-PGCP NP treatment (FIG. 15A-C). Together, our results indicate the potential of PTEN-mRNA-PGCP NPs to restore the tumor-suppressive activity of PTEN in PTEN-defective cells of different tumor origins.

Example 5. In Vivo Pharmacokinetics and Biodistribution of mRNA NPs

Figure 4A:
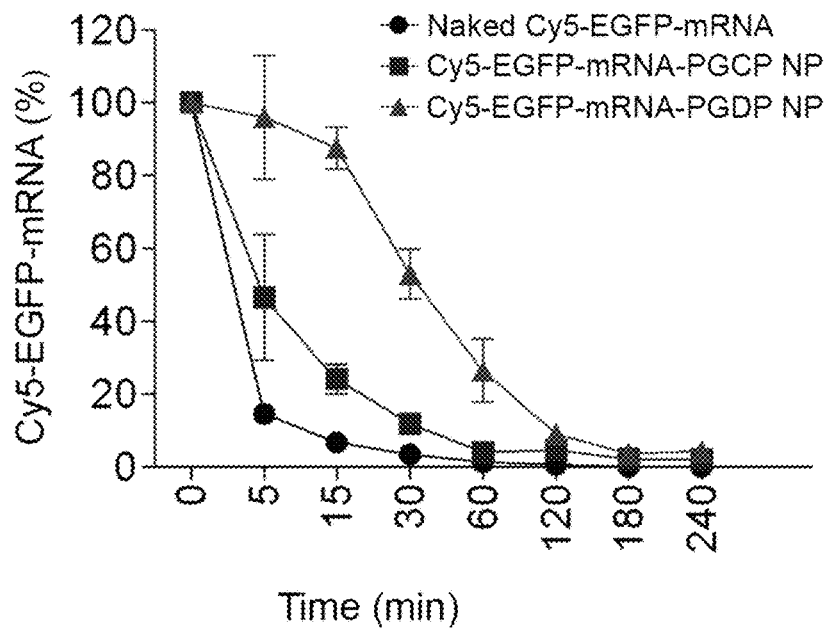
FIG. 4A. Effect of lipid-PEG on pharmacokinetics and biodistribution of mRNA NP. Circulation profile of naked Cy5 EGFP mRNA, and two different mRNA NP formulations with ceramide-PEG (termed as Cy5-EGFP-mRNA-PGCP NP) and DSPE-PEG (termed as Cy5-EGFP-mRNA-PGDP NP) in normal Balb/c male mice after injection (i.v., tail vein) (n=3, mean±SEM).
Figure 4B:
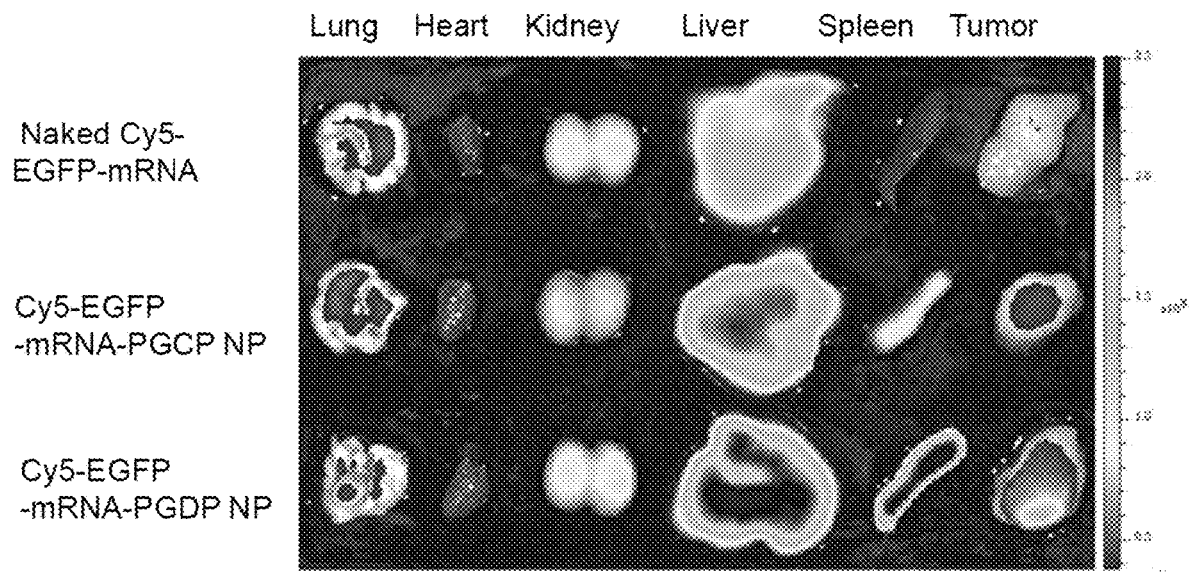
FIG. 4B. Effect of lipid-PEG on pharmacokinetics and biodistribution of mRNA NP. Biodistribution of naked Cy5 EGFP mRNA, Cy5-EGFP-mRNA-PGCP NP, and Cy5-EGFP-mRNA-PGDP NP in different organs including tumors in athymic nude mice bearing PC3-xenograft tumor 24 h post-injection.
Figure 16A:
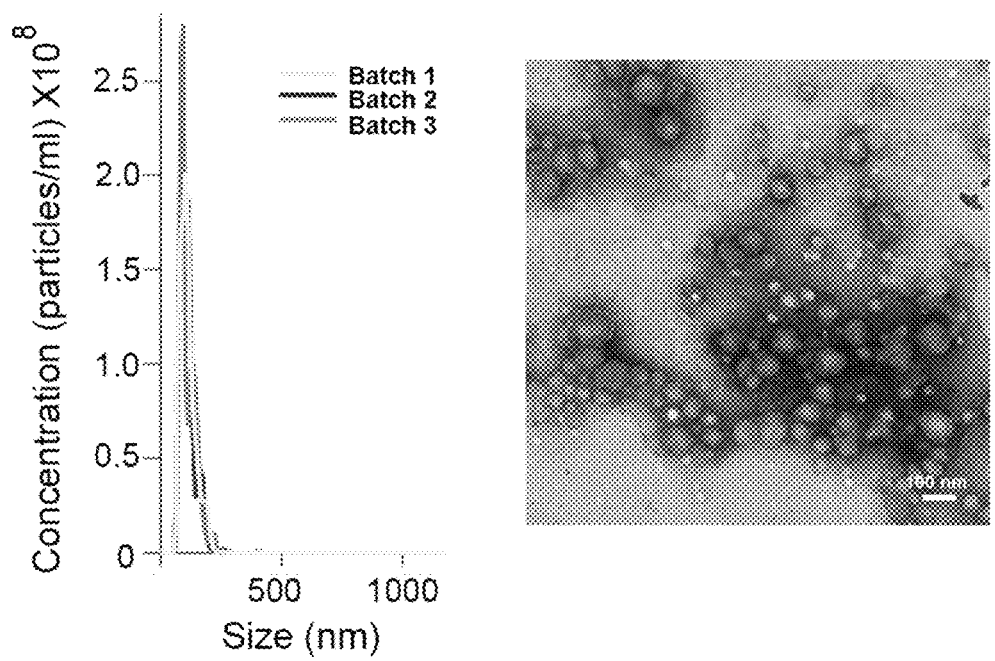
FIG. 16A. Effect of DSPE-PEG on mRNA NP formulation. The mRNA-PGDP NP (prepared with DSPE-PEG) was characterized with NanoSIGHT to check size distribution (112.7±1.3 nm), transmission electron microscopy (TEM) to observe morphology, and dynamic light scattering (DLS) to measure surface charge (5.22±0.43 mV). A weight ratio of 1:15 for mRNA: G0-C14 was the best formulation.
Figure 16B:
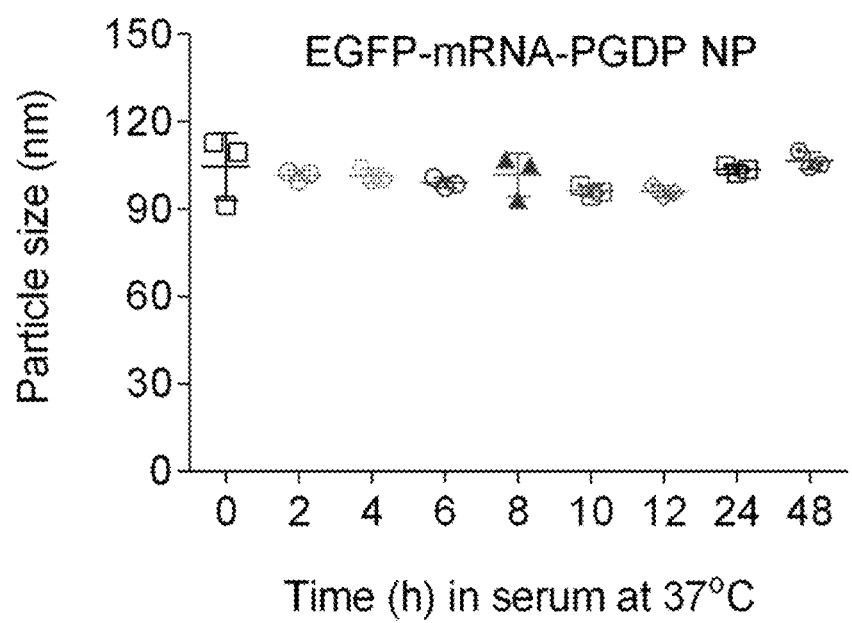
FIG. 16B. Stability of EGFP-mRNA-PGDP NP in 10% serum condition was evaluated by measuring particle size changes determined by NanoSIGHT at various time periods until 48 h.
Figure 17:
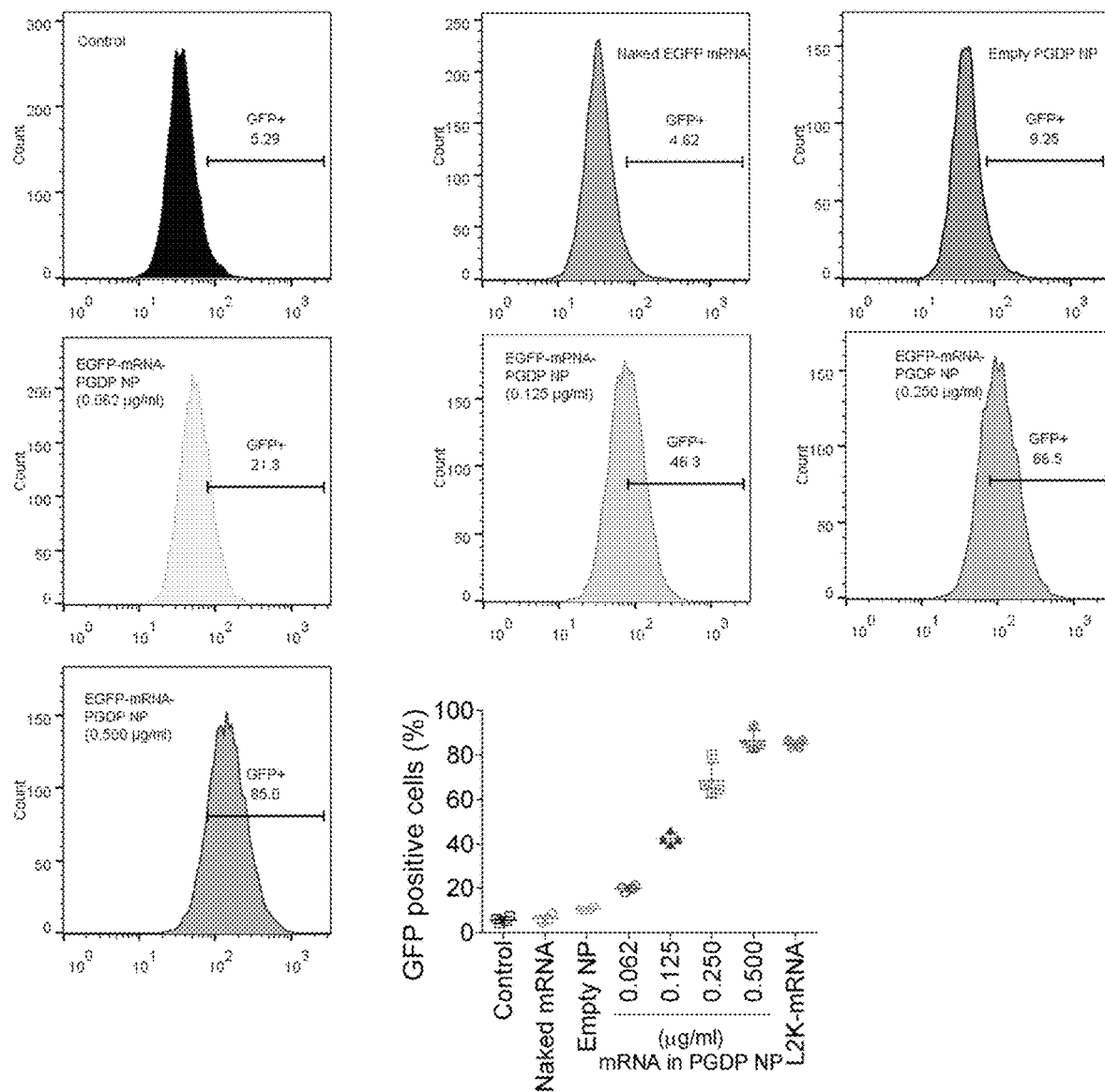
FIG. 17. In vitro transfection efficiency of EGFP-mRNA-PGDP NP in PC3 cells. Cells were treated with various mRNA concentrations (at 0.062, 0.125, 0.250, 0.500 μg/ml) of EGFP-mRNA-PGDP NP for 16 h and further incubated for 24 h under standard cell-culture incubation conditions. Transfection efficiency (% GFP positive cells) was determined using flow cytometry (mean±SD, n=4) and analyzed with the histograms for the respective groups using Flowjo software.

To predict the in vivo performance of our mRNA NPs for systemic delivery, we first evaluated pharmacokinetics (PK) by administering Cy5-EGFP-mRNA NPs prepared with two different lipid-PEGs (ceramide-PEG and DSPE-PEG, termed PGCP and PGDP, respectively) into healthy BALB/c mice via tail-vein intravenous (i.v.) injection and comparing the PK with that of naked Cy5-EGFP-mRNA. The EGFP-mRNA-PGDP NP possessed excellent physicochemical properties, with particle size and surface charge of 112.7±1.3 nm and 5.22±0.43 mV, respectively (FIG. 16A) along with good stability in serum conditions and stable particle size over 48 h at 37° C. (FIG. 16B). Notably, the in vitro transfection efficiency in PC3 cells was greater than 80% at an mRNA concentration of 0.500 µg/ml as measured by GFP fluorescence, which is comparable to that observed with lipofectamine administration of GFP mRNA in vitro (FIG. 17). The PK results showed that naked mRNA was cleared rapidly with a dramatic decrease to ~10% after 5 min. Cy5-EGFP-mRNA-PGCP NP slightly extended the circulation of Cy5-EGFP-mRNA at various time points compared to that of naked mRNA with a half-life ($t_{1/2}$) of >5 min, whereas Cy5-EGFP-mRNA-PGDP NP had an even longer circulation profile ($t_{1/2}$>30 min). Moreover, ~30% of the Cy5-EGFP-mRNA-PGDP NP was still circulating after 60 min, while naked mRNA and Cy5-mRNA-PGCP NP dropped to 1% and 4%, respectively. At 240 min, 5% of the Cy5-EGFP-mRNA-PGDP NP could still be detected (FIG. 4A). To evaluate biodistribution (BioD) and tumor accumulation, athymic nude mice carrying human PC3 xenograft tumor were injected with naked Cy5-EGFP-mRNA and Cy5-EGFP-mRNA NPs (both PGCP and PGDP) via tail vein. A high percentage of NPs accumulated in spleen and liver after i.v. administration. However, most importantly, Cy5-EGFP-mRNA-PGDP NP exhibited high tumor accumulation in the PC3-xenograft, whereas no or minimal signals in tumor were detected for naked Cy5-EGFP-mRNA or Cy5-EGFP-mRNA-PGCP NP (FIG. 4B). We also examined the BioD of PGCP or PGDP NP encapsulating Cy5-tagged PTEN mRNA to specifically assess the distribution of PTEN mRNA in vivo. The result explicitly reproduced similar BioD, exhibiting higher Cy5-PTEN-mRNA distribution in tumor by the PGDP NP, compared to naked Cy5-PTEN-mRNA or Cy5-PTEN-mRNA-PGCP NP (FIG. 18A,B). This high tumor accumulation led us to advance this platform into in vivo efficacy studies with tumor-bearing mice.

Figure 5A:
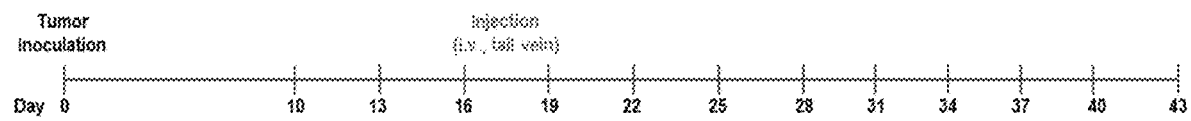
FIG. 5A. In vivo therapeutic validation of PTEN restoration using PTEN-mRNA NP in PCa xenograft model. Scheme of tumor inoculation and systemic injection (i.v., tail-vein) of PBS, EGFP-mRNA-PGDP NP, or PTEN-mRNA-PGDP NP in PC3 tumor-bearing male athymic nude mice. Mice were injected at day 10 post tumor inoculation. Injections were performed every three days for 6 times.
Figure 5B:
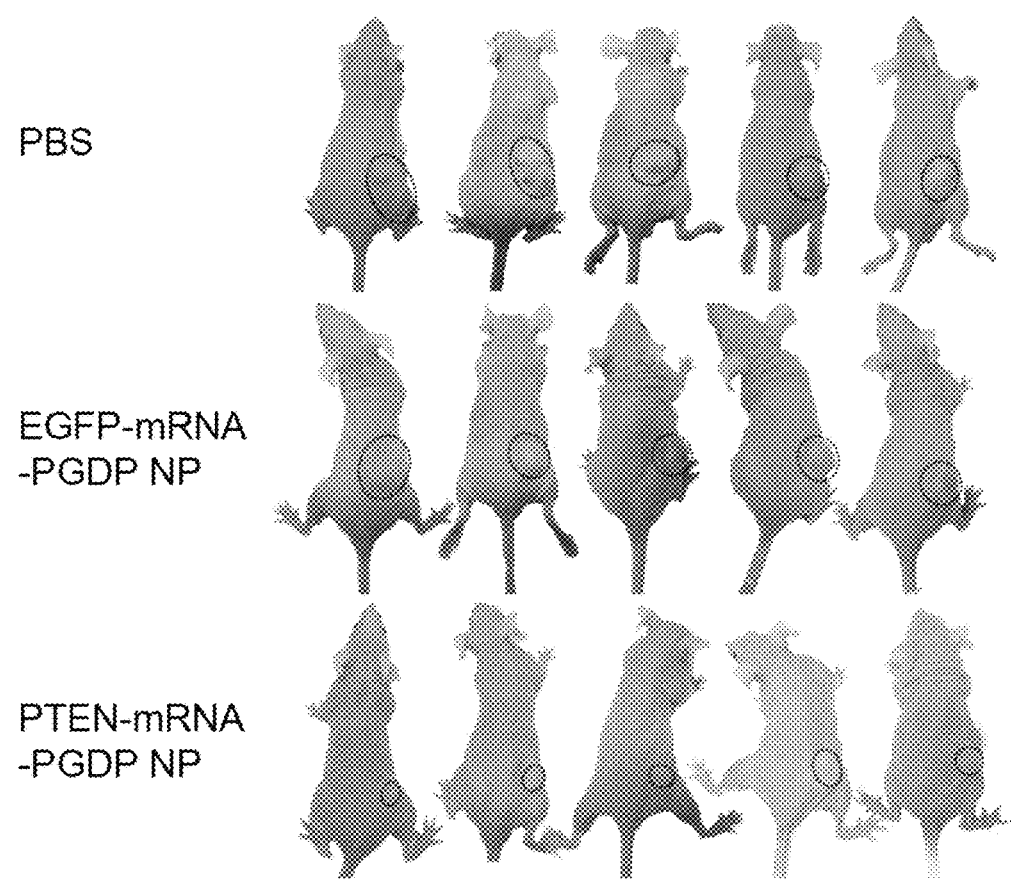
FIG. 5B. In vivo therapeutic validation of PTEN restoration using PTEN-mRNA NP in PCa xenograft model. Whole-body images of mice bearing PC3-xenograft tumors treated with PBS, EGFP-mRNA-PGDP NP, and PTEN-mRNA-PGDP NP (at day 35).
Figure 5C:
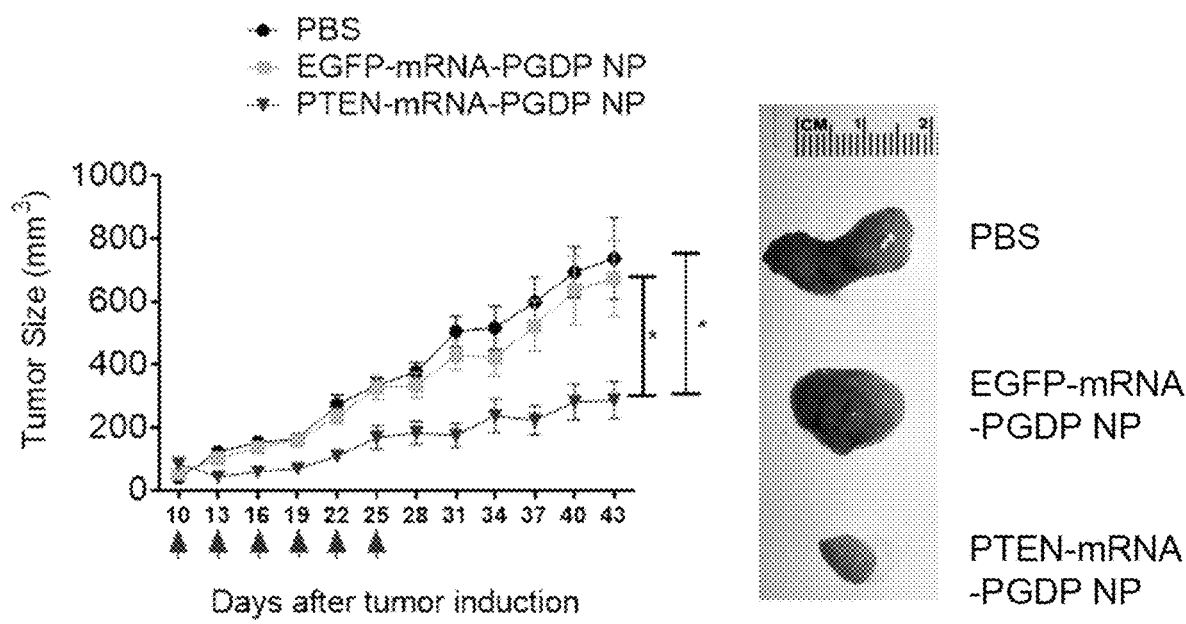
FIG. 5C. In vivo therapeutic validation of PTEN restoration using PTEN-mRNA NP in PCa xenograft model. Tumor growth to show in vivo therapeutic efficacy of PTEN-mRNA-PGDP NP (n=8) as compared to PBS (n=7) and EGFP-mRNA-PGDP NP (n=9) (mean±SEM; *P<0.05 vs. PBS or EGFP-mRNA-PGDP NP. The arrows indicate i.v., tail vein injections. Tumor size measurement began on day 10 and continued every three days until day 43. The representative excised tumor images are also shown on the right.
Figure 5D:
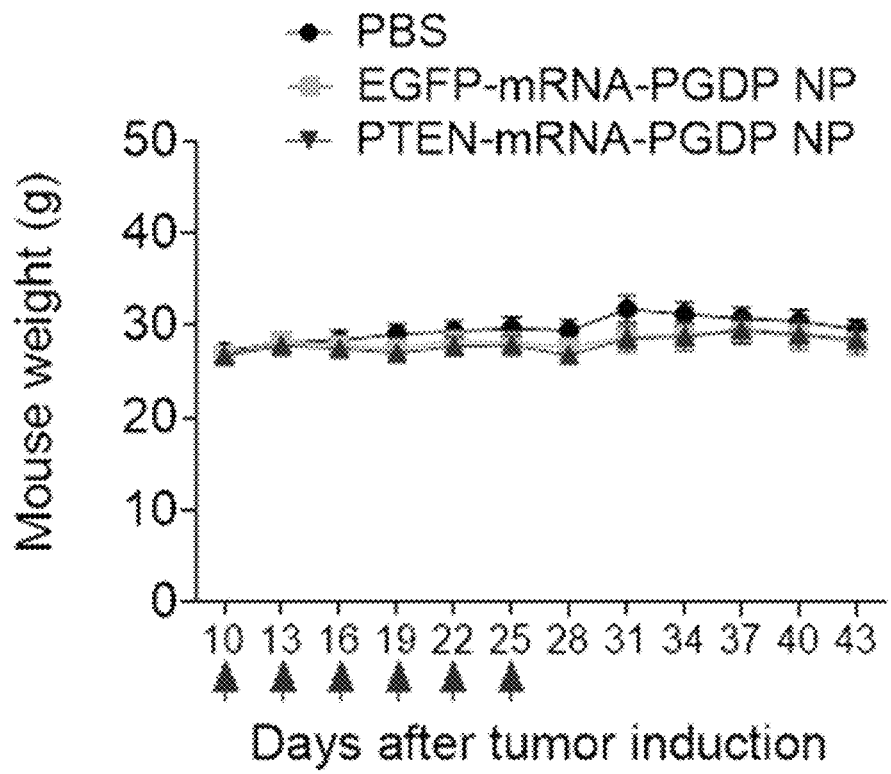
FIG. 5D. In vivo therapeutic validation of PTEN restoration using PTEN-mRNA NP in PCa xenograft model. The average body weight of the PC3 tumor-bearing xenograft mice over the course of therapy (mean±SEM).
Figure 18C:
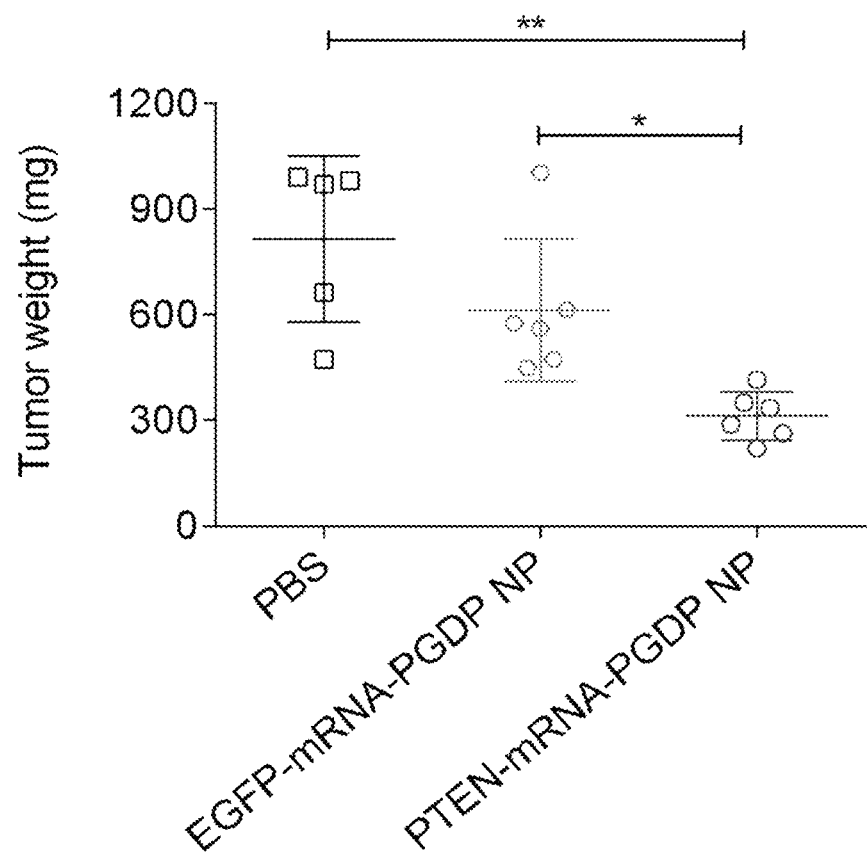
FIG. 18C. The average tumor weight of the PC3 tumor-bearing xenograft mice over the course of therapy with PBS (n=5), EGFP-mRNA-PGDP NP (n=6), and PTEN-mRNA-PGDP NP (n=6) (mean±SEM, *P<0.05 vs. EGFP-mRNA-PGDP NP and **P<0.01 vs. PBS).

Example 6. In Vivo Therapeutic Efficacy and Mechanism of PTEN mRNA NP in PCa Xenograft Model To validate the in vivo therapeutic efficacy of PTEN mRNA NP in PCa xenograft model, we systemically (i.v. via tail vein) injected PTEN-mRNA-PGDP NP every three days for six injections (FIG. 5A) in immunocompromised athymic nude mice bearing subcutaneous PC3 xenograft tumors. Tumor-bearing mice injected with PBS and EGFP-mRNA-PGDP NP were used as controls. Both PBS and EGFP-mRNA-PGDP NP groups showed rapid tumor growth, while PTEN-mRNA-PGDP NP treatment notably suppressed tumor growth compared to controls (FIG. 5B,C). The average tumor sizes rapidly increased to ~674 mm$^3$ and ~738 mm$^3$ for the controls, EGFP-mRNA-PGDP NP and PBS, respectively, which were significantly higher compared to ~288 mm³ for PTEN-mRNA-PGDP NP treatment at day 43 post tumor induction (FIG. 5C). Moreover, the average tumor weight for the PTEN-mRNA-PGDP NP treatment group was also significantly lower than that of control groups (FIG. 18C). No treatment group underwent significant changes in body weight, suggesting minimal toxicity (FIG. 5D). These results demonstrate the feasibility of using systemic mRNA NP delivery to reverse the effects of tumor suppressor loss in prostate tumors in vivo.

To further understand the mechanisms underlying the therapeutic activity of PTEN-mRNA-PGDP NP, we assessed HA-PTEN expression in tumor sections obtained on the third day after the last injection by immunohistochemistry analysis using HA antibody. PTEN-mRNA-PGDP NP treatment resulted in HA-PTEN protein expression in tumor, whereas PBS and EGFP-mRNA-PGDP NP controls did not show any background PTEN-HA expression (FIG. 5E). Next, TUNEL assay in tumor sections revealed that PTEN-mRNA-PGDP NP increased tumor cell apoptosis significantly more than either EGFP-mRNA-PGDP NP or PBS. These results suggest that the effective systemic restoration and efficient expression of PTEN in tumors mediated by NP delivery of PTEN mRNA leads to enhanced tumor-cell apoptosis and decreased tumor cell survival. Consequently, this approach may represent a viable treatment strategy for restoring tumor suppression to PCa tumors in vivo.

Example 7. In Vivo Therapeutic Efficacy of PTEN mRNA NPs in Advanced PCa Models

Figure 6C:
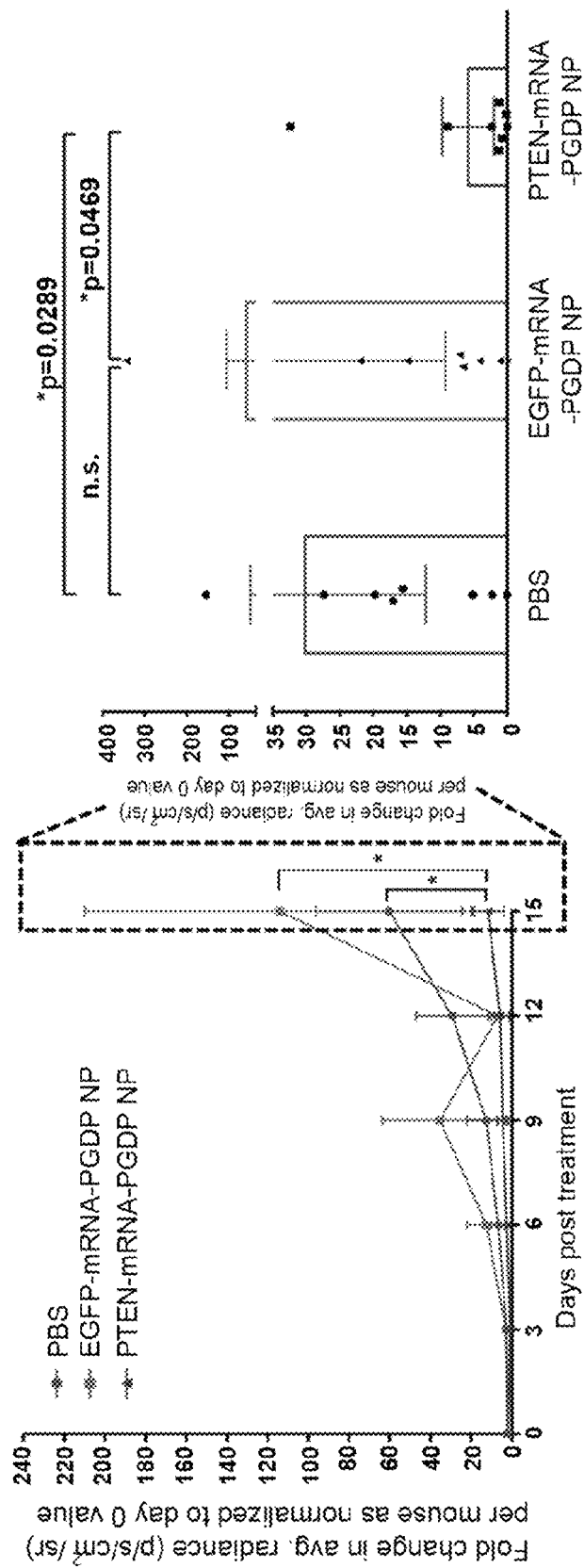
FIG. 6C. In vivo therapeutic validation of PTEN restoration using PTEN-mRNA NPs in disseminated metastatic PCa model. Fold change in average radiance per mouse by normalizing to day 0 tumor burden as determined by bioluminescent imaging; inset: fold change in average radiance per mouse at experimental endpoint (day 15) for each treatment group (mean±SEM).
Figure 19A:
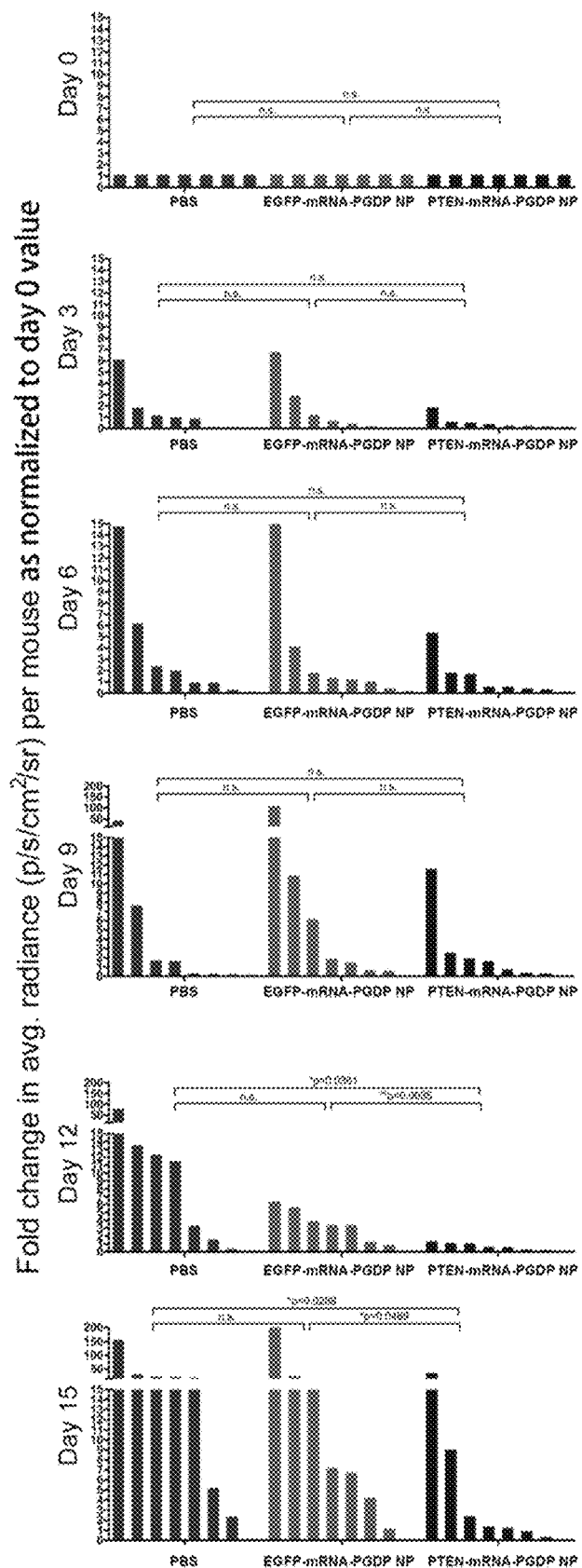
FIG. 19A. In vivo therapeutic validation of PTEN restoration using PTEN-mRNA NPs in advanced PCa (PC3-disseminated metastatic and IT orthotopic) models. Fold change in average radiance per mouse as normalized to day 0 tumor burden determined by bioluminescent imaging, represented as a waterfall plot with each bar representing one mouse (n=8 mice per cohort).

To validate the in vivo therapeutic efficacy of PTEN mRNA NP in advanced PCa models, we first established a disseminated PC3 metastatic model by injecting luciferase-tagged PC3 (PC3-luc) cells into the tail vein of immunocompromised, male athymic nude mice. Tumor metastases were detected in the lung and other organs of the mice, by bioluminescence imaging (Bruker Xtreme). Four weeks post tumor challenge, we systemically (i.v. via tail vein) injected PTEN or EGFP mRNA-loaded PGDP NPs every three days for five injection doses and compared to PBS. Based on the fold change of bioluminescence of PC3-luc cells in mice, it was found that the PTEN-mRNA-PGDP NP significantly prevented the progression of metastatic cancer when compared to PBS and EGFP-mRNA-PGDP NP treatment groups used as controls (FIG. 6A). Quantitative analysis demonstrated a significant difference of the fold change in average radiance at the experimental endpoint (day 15) in the PTEN-mRNA-PGDP NP vs. the PBS cohort (*p=0.0289), as well as the PTEN-mRNA-PGDP NP vs. the EGFP-mRNA-PGDP NP cohort (*p=0.0469) (FIG. 6B,C, FIG. 19A). These results demonstrate the efficacy of the systemic delivery of PTEN mRNA-loaded NPs in a disseminated metastatic PCa model.

Figure 7A:
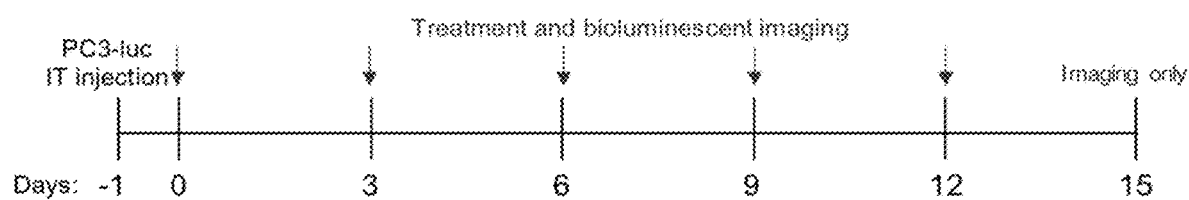
FIG. 7A. In vivo therapeutic validation of PTEN restoration using PTEN-mRNA NPs in IT orthotopic PCa model. Scheme of IT tumor inoculation and systemic injection (i.v., tail-vein) of PBS, EGFP-mRNA-PGDP NP, or PTEN-mRNA-PGDP NP (n=12 mice; n=24 tibiae per cohort) in IT PC3-luc-bearing male athymic nude mice.
Figure 7B:
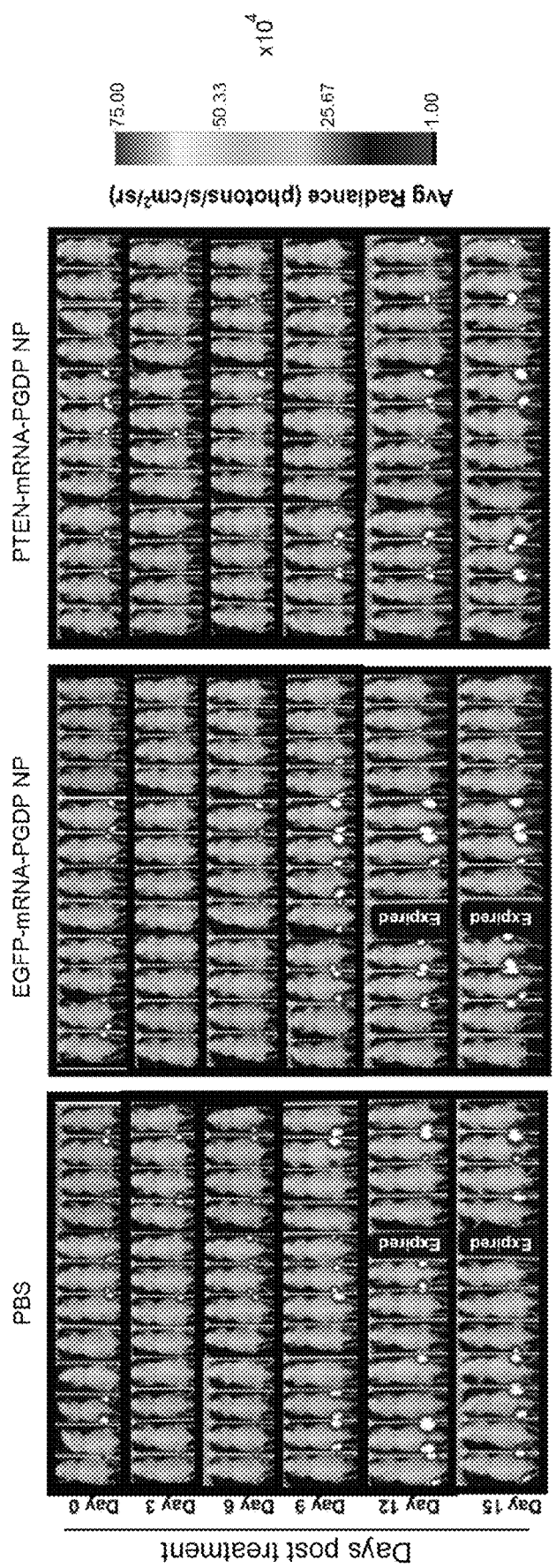
FIG. 7B. In vivo therapeutic validation of PTEN restoration using PTEN-mRNA NPs in IT orthotopic PCa model. Bioluminescent imaging of total radiance of PC3-luc at time points post IT injections and treatments.
Figure 7C:
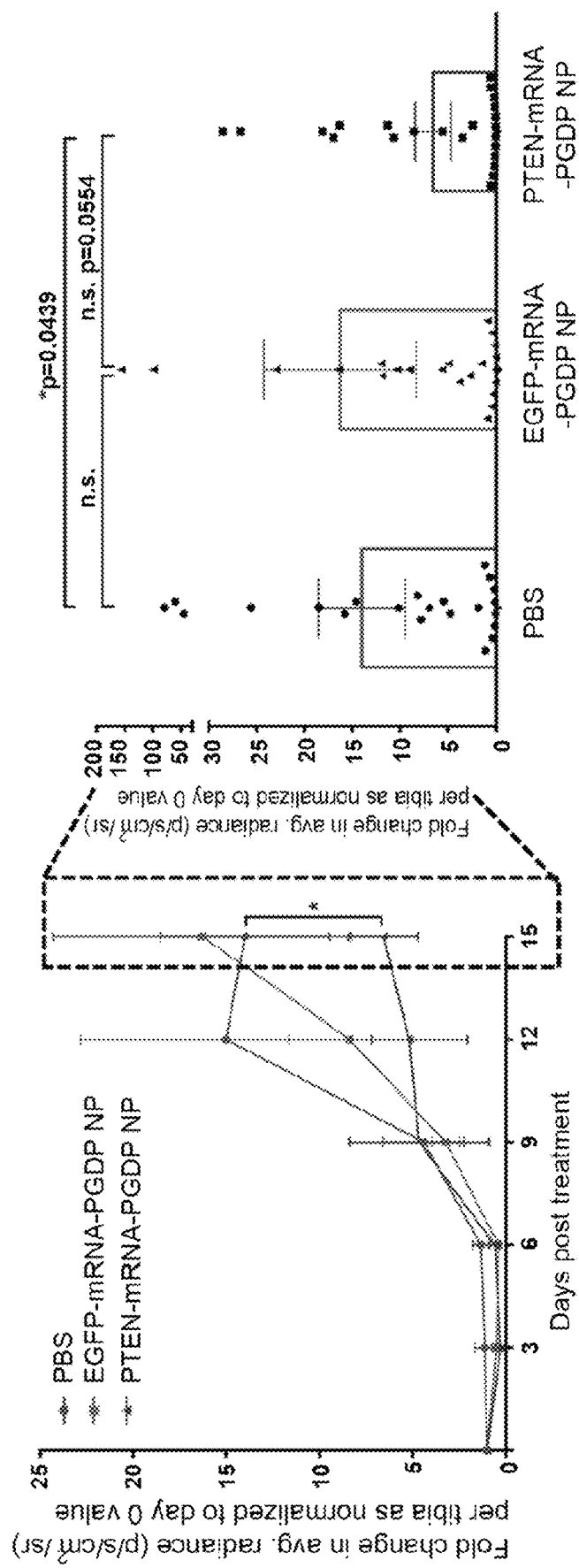
FIG. 7C. In vivo therapeutic validation of PTEN restoration using PTEN-mRNA NPs in IT orthotopic PCa model. Fold change in average radiance per tibia as normalized to day 0 tumor burden as determined by bioluminescent imaging; inset: fold change in average radiance per tibia at experimental endpoint (day 15) for each treatment group (mean±SEM).
Figure 19B:
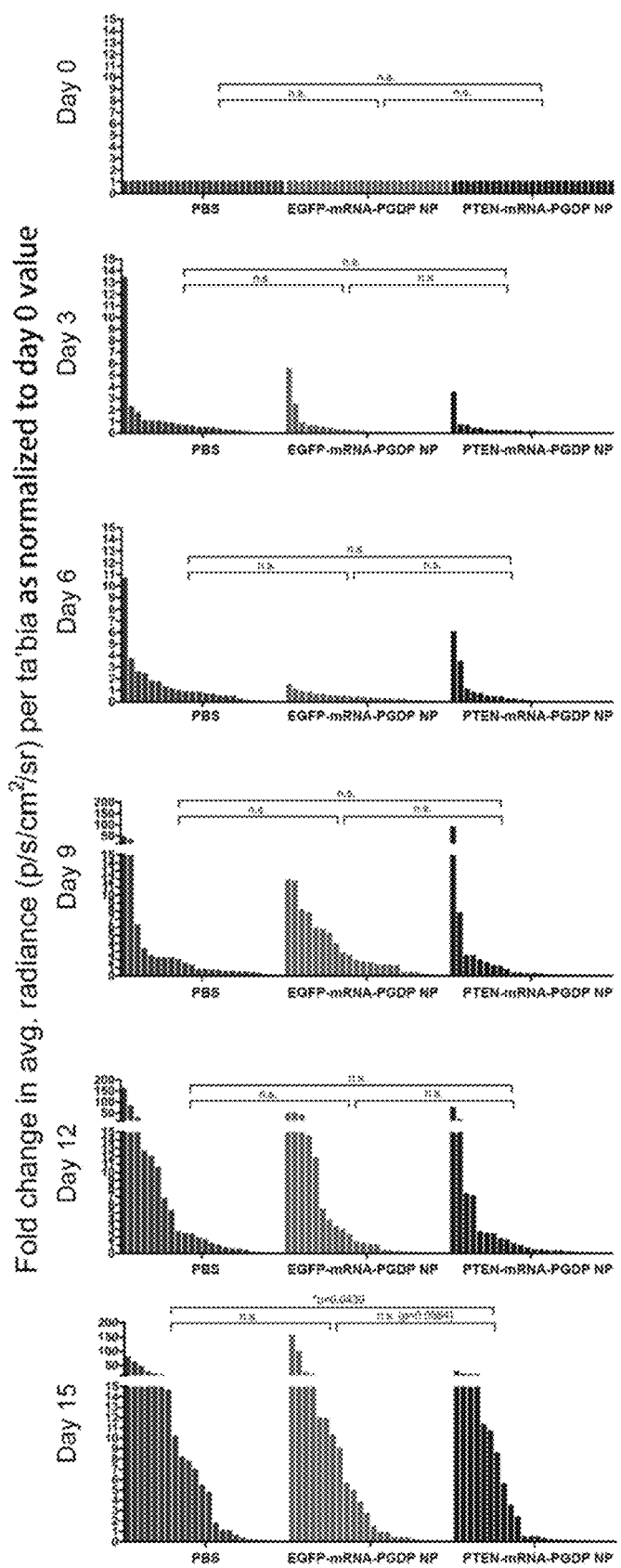
FIG. 19B. Fold change in average radiance per tibia post IT injection of PC3-luc cells as normalized to day 0 tumor burden determined by bioluminescent imaging, represented as a waterfall plot with each bar representing one tibia (n=12 mice; n=24 tibae per cohort).
Figure 20A:
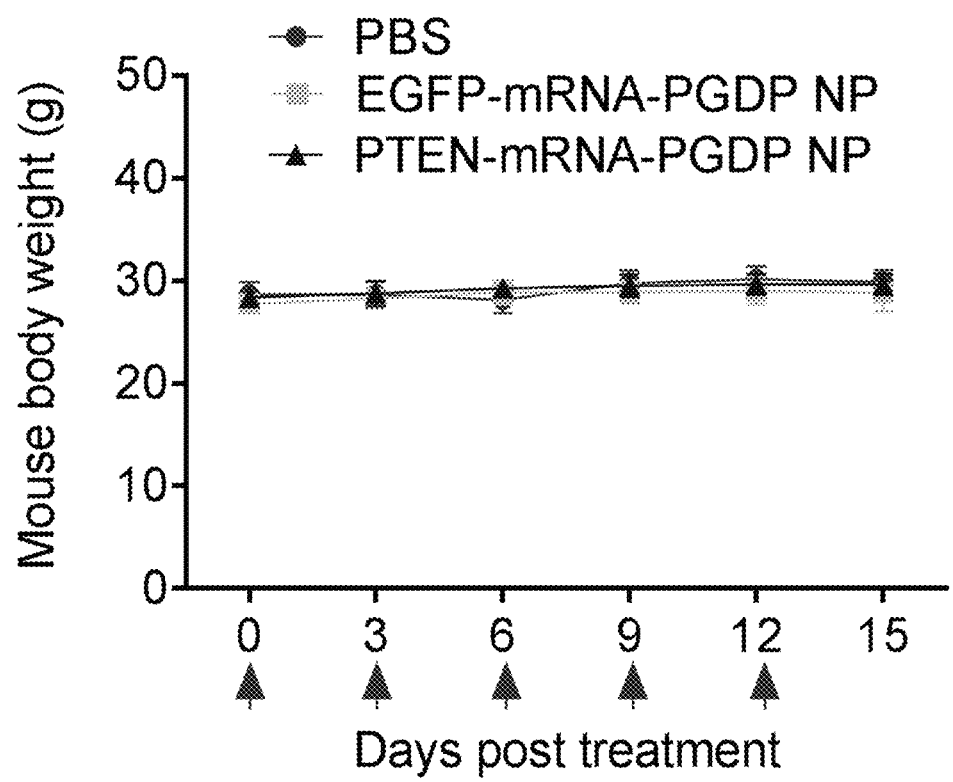
FIG. 20A. The average mouse body weight of the PC3-luc disseminated metastatic mice (n=8 mice per cohort).
Figure 20B:
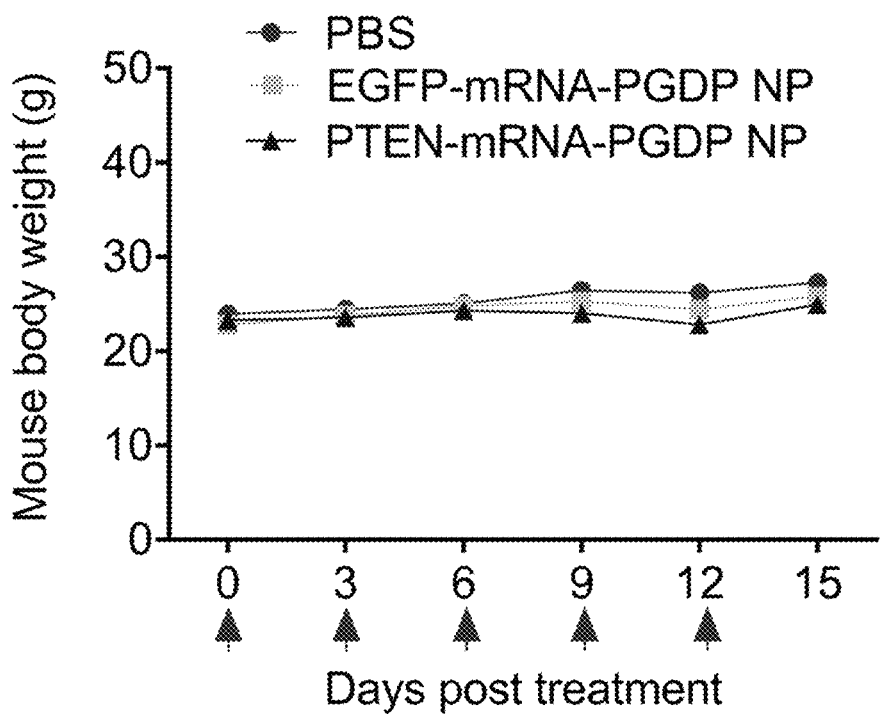
FIG. 20B. IT orthotopic PC3-luc-bearing mice (n=12 mice per cohort), over the course of therapy (mean±SEM).

We also tested the mRNA NPs in a PCa bone model given that bone is the most common site of PCa metastasis[52]. We performed the orthotopic, intratibial (IT) injections with the PC3-luc cells in immunocompromised, male athymic nude mice, and systemically injected PTEN-mRNA-PGDP NPs one day post tumor inoculation and every three days for five injections in total (FIG. 7A). Both PBS and EGFP-mRNA-PGDP NP control groups demonstrated rapid tumor growth (FIG. 7B,C), whereas mice receiving PTEN-mRNA-PGDP NP as compared to PBS treatment showed a significant decrease in fold change in average radiance at the experimental endpoint (per tibia as normalized to day 0 tibia value, day 15, *p=0.0439) (FIG. 7C, FIG. 19B). At the IT orthotopic model experimental endpoint (day 15), cohorts which received PTEN-mRNA-PGDP NP treatment experienced approximately a 60% reduction in the fold change in average radiance per tibia (normalized to day 0) compared to mice receiving control EGFP-mRNA-PGDP NP treatment (fold change for PTEN-mRNA-PGDP NPs in tibia tumor burden was 6.6, and fold change for EGFP-mRNA-PGDP NPs in tibia tumor burden was 16.3; p=0.0554). These findings indicate an ability of PTEN-mRNA-PGDP NPs to reduce tibia tumor burden (FIG. 7C, FIG. 19B). These results are further indicative of the ability of PTEN mRNA NP delivery to decrease tumor outgrowth in an orthotopic site of PCa metastasis. Notably, no treatment group showed any significant changes of body weight in both the disseminated metastatic and IT orthotopic PCa models, suggesting safety of this therapeutic platform (FIG. 20).

Example 8. In Vivo Safety Profile of PTEN mRNA NP

Figure 8A:
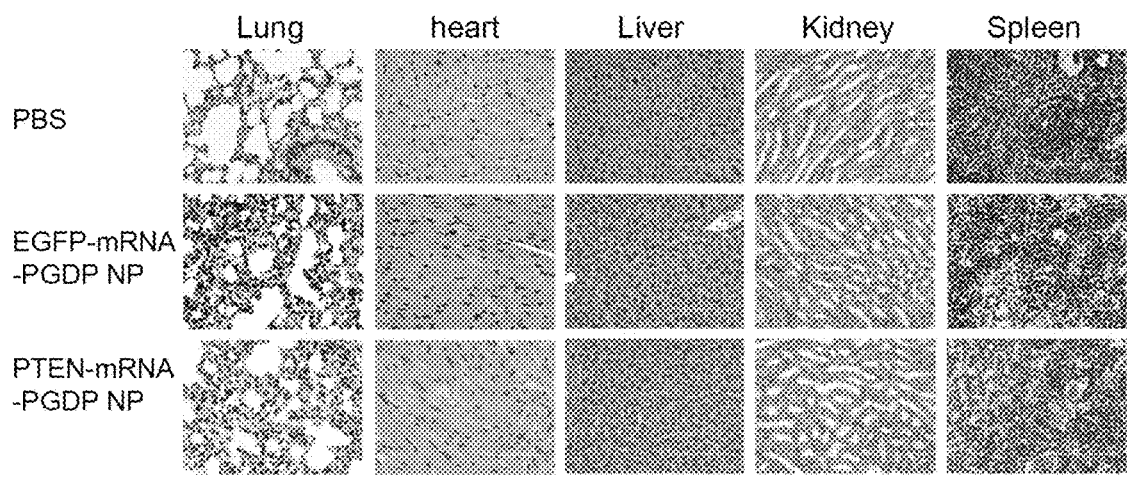
FIG. 8A. In vivo toxicity studies by histopathological and hematological analysis after treatment of mRNA NPs vs. PBS. For histopathological assay, H&E staining of tissue sections of major organs was analyzed three days after the last injection of PBS, EGFP-mRNA-PGDP NP, and PTEN-mRNA-PGDP NP at day 28 post tumor inoculation as shown in the scheme of FIG. 6A. Images were taken at 20× magnification. For hematological assay, the levels of aspartate aminotransferase (AST), alanine aminotransferase (ALT), blood urea nitrogen (BUN), creatinine, and troponin-1 in serum were measured at day 28 (a) and at day 43 (b) post tumor inoculation (mean±SD, n=5, n.d.: not detectable).
Figure 8A:
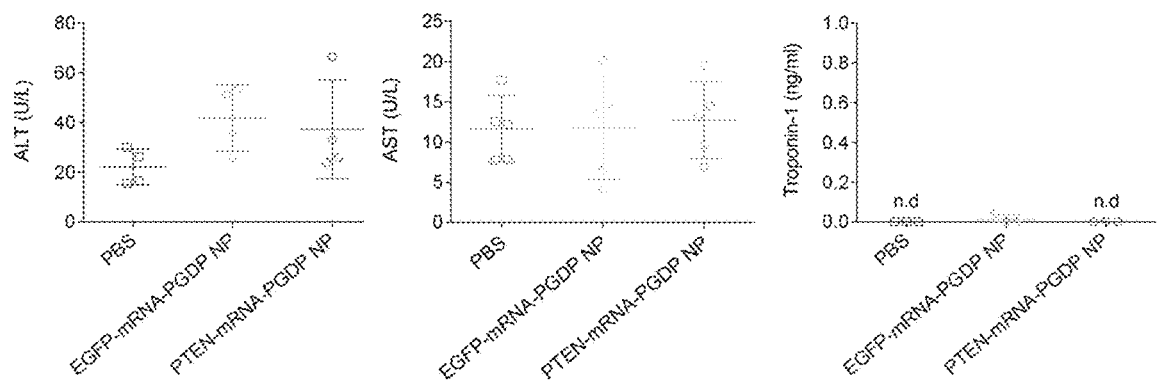
Figure 8A:
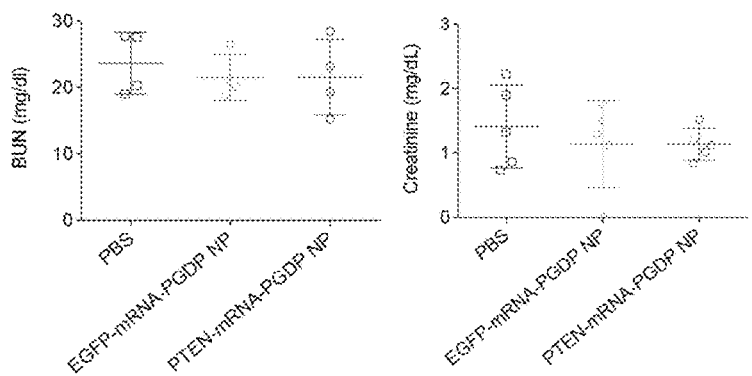
Figure 8B:
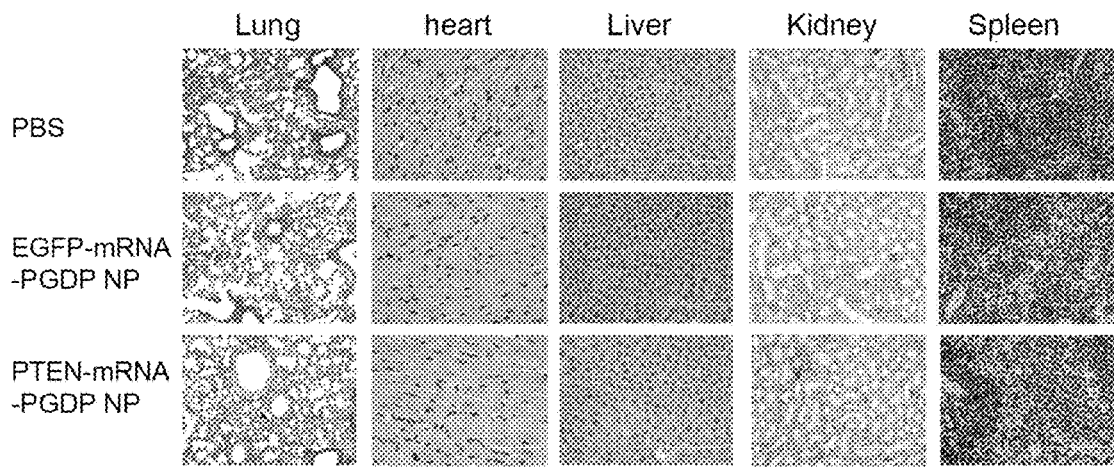
FIG. 8B. In vivo toxicity studies by histopathological and hematological analysis after treatment of mRNA NPs vs. PBS. For histopathological assay, H&E staining of tissue sections of major organs was analyzed three days after the last injection of PBS, EGFP-mRNA-PGDP NP, and PTEN-mRNA-PGDP NP at the endpoint of day 43 post tumor inoculation as shown in the scheme of FIG. 6A. Images were taken at 20× magnification. For hematological assay, the levels of aspartate aminotransferase (AST), alanine aminotransferase (ALT), blood urea nitrogen (BUN), creatinine, and troponin-1 in serum were measured at day 28 (a) and at day 43 (b) post tumor inoculation (mean±SD, n=5, n.d.: not detectable).
Figure 8B:
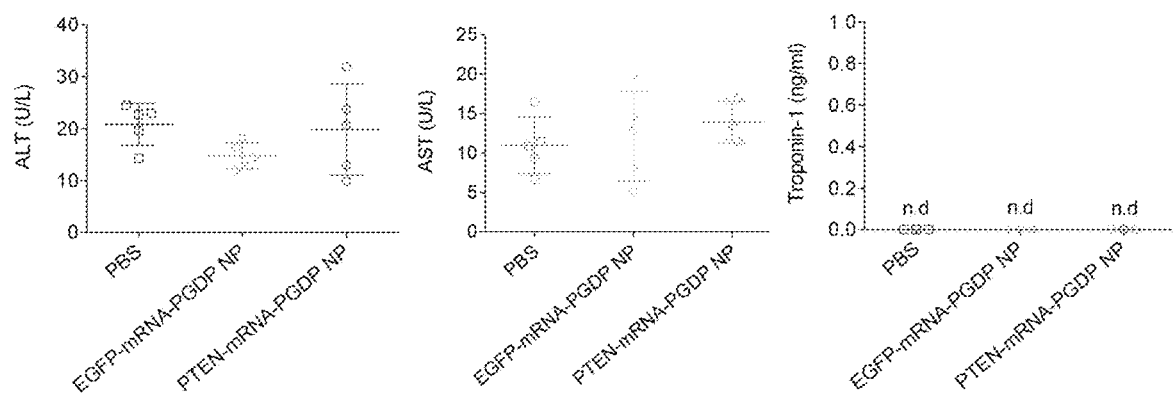
Figure 8B:
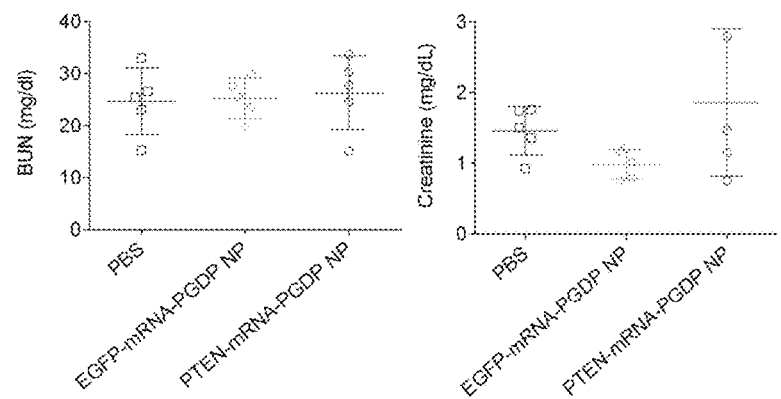

To evaluate the in vivo side effects of mRNA NPs, various organs and blood serum were harvested three days after the last injection (day 28) and at the end point (day 43) of the PCa xenograft experiment (FIG. 8A,B). Organs were sectioned and H&E stained. We found no histological differences in the tissues from lung, heart, liver, spleen, or kidney between PBS and NP treatment groups, suggesting no notable toxicity. For hematological analysis (days 28 and 43), we checked parameters including aspartate aminotransferase (AST) & alanine aminotransferase (ALT) to assess liver function, creatinine and blood urea nitrogen (BUN) to evaluate kidney activity, and troponin-1 to assess cardiac function using appropriate assay kits. We found no obvious changes in these parameters in serum from mice after treatment with the mRNA NPs, further indicating negligible side effects.

Figure 21:
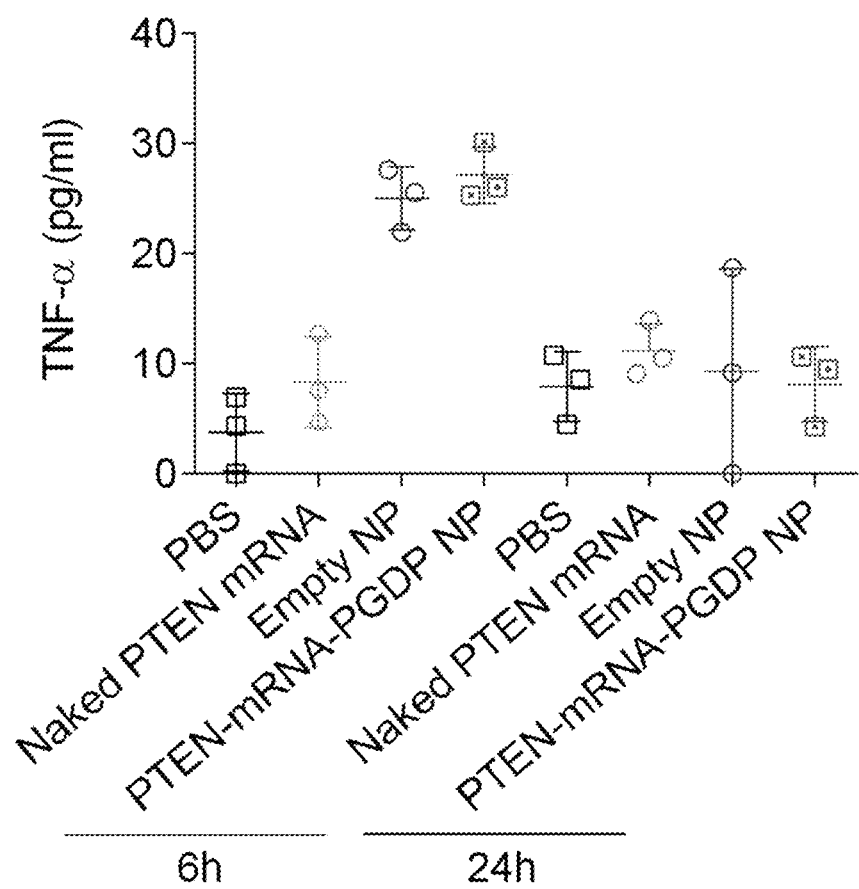
FIG. 21. In vivo toxicity assessment by measuring immune stimulation after treatment of immunocompetent BALB/c male normal mice with PBS, naked PTEN mRNA, empty PGDP NP, and PTEN-mRNA-PGDP NP. Serum levels of TNF-α were measured 6 and 24 h post injection (i.v., tail vein) of the above groups (n=3, mean±SEM).

We also investigated whether mRNA NPs mediated any in vivo immune response in immunocompetent mice to exclude the possibility that the anti-tumor efficacy of PTEN mRNA NP might be caused by an immunostimulatory effect. There was a similarly modest increase in levels of proinflammatory cytokine TNF-α for both the empty PGDP NP and the PTEN-mRNA-PGDP NP at 6 h post-injection, suggesting that the cytokine response may be attributable to the NP itself rather than the effect of encapsulated PTEN-mRNA. PBS and naked PTEN mRNA stimulated minimal TNF-α response as expected (FIG. 21). TNF-α levels for both empty PGDP NPs and PTEN-mRNA-PGDP NPs returned to baseline PBS levels 24 h post-injection, suggesting that immune stimulation (e.g., TNF-α) by the NP itself was transient and that the PTEN mRNA had no lasting adverse immune/inflammatory activity. In sum, our results demonstrate effective reversal of the PTEN-null phenotype in PCa and in breast cancer cells in vitro and in vivo after systemic delivery of PTEN-mRNA-PGDP NPs. The inhibitory effect is dependent on the presence of PTEN mRNA delivered by the NP and is not mediated by non-specific host responses to either the NP itself or to the introduction of other mRNA species.

REFERENCES

1. Song, M. S., Salmena, L. & Pandolfi, P. P. The functions and regulation of the PTEN tumour suppressor. Nat. Rev. Mol. Cell Biol. 13, 283-296 (2012).

2. McCall, P., Witton, C. J., Grimsley, S., Nielsen, K. V. & Edwards, J. Is PTEN loss associated with clinical outcome measures in human prostate cancer? Br. J. Cancer 99, 1296-1301 (2008).
3. Yoshimoto, M. et al. Interphase FISH analysis of PTEN in histologic sections shows genomic deletions in 68% of primary prostate cancer and 23% of high-grade prostatic intra-epithelial neoplasias. Cancer Genet. Cytogenet. 169, 128-137 (2006).
4. Han, B. et al. Fluorescence in situ hybridization study shows association of PTEN deletion with ERG rearrangement during prostate cancer progression. Mod Pathol 22, 1083-1093 (2009).
5. Verhagen, P. C. et al. The PTEN gene in locally progressive prostate cancer is preferentially inactivated by bi-allelic gene deletion. J. Pathol. 208, 699-707 (2006).
6. Yoshimoto, M. et al. FISH analysis of 107 prostate cancers shows that PTEN genomic deletion is associated with poor clinical outcome. Br. J. Cancer. 97, 678-685 (2007).
7. Sircar, K. et al. PTEN genomic deletion is associated with p-Akt and AR signalling in poorer outcome, hormone refractory prostate cancer. J. Pathol. 218, 505-513 (2009).
8. Schmitz, M. et al. Complete loss of PTEN expression as a possible early prognostic marker for prostate cancer metastasis. Int. J. Cancer 120, 1284-1292 (2007).
9. Lotan, T. L. et al. PTEN protein loss by immunostaining: analytic validation and prognostic indicator for a high risk surgical cohort of prostate cancer patients. Clin. Cancer Res. 17, 6563-6573 (2011).
10. Stambolic, V. et al. Negative regulation of PKB/Akt-dependent cell survival by the tumor suppressor PTEN. Cell 95, 29-39 (1998).
11. Furnari, F. B., Lin, H., Huang, H. S. & Cavenee, W. K. Growth suppression of glioma cells by PTEN requires a functional phosphatase catalytic domain. Proc. Natl. Acad. Sci. USA. 94, 12479-12484 (1997).
12. Sun, H. et al. PTEN modulates cell cycle progression and cell survival by regulating phosphatidylinositol 3,4,5-trisphosphate and Akt/protein kinase B signaling pathway. Proc. Natl. Acad. Sci. USA. 96, 6199-6204 (1999).
13. Suzuki, A. et al. High cancer susceptibility and embryonic lethality associated with mutation of the PTEN tumor suppressor gene in mice. Curr. Biol. 8, 1169-1178 (1998).
14. Maehama, T. & Dixon, J. E. The tumor suppressor, PTEN/MMAC1, dephosphorylates the lipid second messenger, phosphatidylinositol 3,4,5-trisphosphate. J Biol Chem 273, 13375-13378 (1998).
15. Engelman, J. A., Luo, J. & Cantley, L. C. The evolution of phosphatidylinositol 3-kinases as regulators of growth and metabolism. Nat. Rev. Genet. 7, 606-619 (2006).
16. Taylor, B. S. et al. Integrative genomic profiling of human prostate cancer. Cancer Cell 18, 11-22 (2010).
17. Grasso, C. S. et al. The mutational landscape of lethal castration-resistant prostate cancer. Nature 487, 239-243 (2012).
18. Backman, S. A. et al. Deletion of Pten in mouse brain causes seizures, ataxia and defects in soma size resembling Lhermitte-Duclos disease. Nat. Genet. 29, 396-403 (2001).
19. Liliental, J. et al. Genetic deletion of the Pten tumor suppressor gene promotes cell motility by activation of Rac1 and Cdc42 GTPases. Curr. Biol. 10, 401-404 (2000).
20. Tamura, M. et al. Inhibition of cell migration, spreading, and focal adhesions by tumor suppressor PTEN. Science 280, 1614-1617 (1998).
21. Hamada, K. et al. The PTEN/PI3K pathway governs normal vascular development and tumor angiogenesis. Genes Dev. 19, 2054-2065 (2005).
22. Jiang, B. H. & Liu, L. Z. PI3K/PTEN signaling in angiogenesis and tumorigenesis. Adv. Cancer Res. 102, 19-65 (2009).
23. Yin, H. et al. Non-viral vectors for gene-based therapy. Nat. Rev. Genet. 15, 541-555 (2014).
24. Quabius, E. S. & Krupp, G. Synthetic mRNAs for manipulating cellular phenotypes: an overview. Nat. Biotechnol. 32, 229-235 (2015).
25. Lee, J., Boczkowski, D. & Nair, S. Programming human dendritic cells with mRNA. Methods Mol. Biol. 969, 111-125 (2013).
26. Yamamoto, A., Kormann, M., Rosenecker, J. & Rudolph, C. Current prospects for mRNA gene delivery. Eur. J. Pharm. Biopharm. 71, 484-489 (2009).
27. Leonhardt, C. et al. Single-cell mRNA transfection studies: delivery, kinetics and statistics by numbers. Nanomedicine 10, 679-688 (2014).
28. Ligon, T. S., Leonhardt, C. & Radler, J. O. Multi-level kinetic model of mRNA delivery via transfection of lipoplexes. PloS one 9, e107148 (2014).
29. Islam, M. A. et al. Biomaterials for mRNA delivery. Biomater. Sci. 3, 1519-1533 (2015).
30. Davis, M. E. et al. Evidence of RNAi in humans from systemically administered siRNA via targeted nanoparticles. Nature 464, 1067-1070 (2010).
31. Zuckerman, J. E. et al. Correlating animal and human phase Ia/Ib clinical data with CALAA-01, a targeted, polymer-based nanoparticle containing siRNA. Proc. Natl. Acad. Sci. USA. 111, 11449-11454 (2014).
32. Tabernero, J. et al. First-in-humans trial of an RNA interference therapeutic targeting VEGF and KSP in cancer patients with liver involvement. Cancer Discov. 3, 406-417 (2013).
33. Strumberg, D. et al. Phase I clinical development of Atu027, a siRNA formulation targeting PKN3 in patients with advanced solid tumors. Int. J. Clin. Pharmacol. Ther. 50, 76 (2012).
34. Schultheis, B. et al. First-in-human phase I study of the liposomal RNA interference therapeutic Atu027 in patients with advanced solid tumors. J. Clin. Oncol. 32, 4141-4148 (2014).
35. Tolcher, A. W. et al. A phase 1 study of the BCL2-targeted deoxyribonucleic acid inhibitor (DNAi) PNT2258 in patients with advanced solid tumors. Cancer Chemother. Pharmacol. 73, 363-371 (2014).
36. Akinc, A. et al. A combinatorial library of lipid-like materials for delivery of RNAi therapeutics. Nat. Biotech. 26, 561-569 (2008).
37. Whitehead, K. A. et al. Degradable lipid nanoparticles with predictable in vivo siRNA delivery activity. Nat. Commun. 5 (2014).
38. Whitehead, K. A., Langer, R. & Anderson, D. G. Knocking down barriers: advances in siRNA delivery. Nat. Rev. Drug Discov. 8, 129-138 (2009).
39. Zuckerman, J. E. & Davis, M. E. Clinical experiences with systemically administered siRNA-based therapeutics in cancer. Nat. Rev. Drug Discov. 14, 843-856 (2015).
40. Yin, H. et al. Non-viral vectors for gene-based therapy. Nature Reviews Genetics 15, 541-555 (2014).
41. Conde, J., Oliva, N., Atilano, M., Song, H. S. & Artzi, N. Self-assembled RNA-triple-helix hydrogel scaffold for microRNA modulation in the tumour microenvironment. Nat. Mater. 15, 353-363 (2016).

42. Kauffman, K. J. et al. Optimization of Lipid Nanoparticle Formulations for mRNA Delivery in Vivo with Fractional Factorial and Definitive Screening Designs. Nano Lett. 15, 7300-7306 (2015).
43. Kormann, M. S. et al. Expression of therapeutic proteins after delivery of chemically modified mRNA in mice. Nat. Biotech. 29, 154-157 (2011).
44. Li, B. et al. An orthogonal array optimization of lipid-like nanoparticles for mRNA delivery in vivo. Nano Letters 15, 8099-8107 (2015).
45. Zhu, X. et al. Long-circulating siRNA nanoparticles for validating Prohibitin1-targeted non-small cell lung cancer treatment. Proc. Natl. Acad. Sci. USA. 112, 7779-7784 (2015).
46. Islam, M. A. et al. The role of osmotic polysorbitol-based transporter in RNAi silencing via caveolae-mediated endocytosis and COX-2 expression. Biomaterials 33, 8868-8880 (2012).
47. Islam, M. A. et al. Accelerated gene transfer through a polysorbitol-based transporter mechanism. Biomaterials 32, 9908-9924 (2011).
48. Warren, L. et al. Highly efficient reprogramming to pluripotency and directed differentiation of human cells with synthetic modified mRNA. Cell Stem Cell 7, 618-630 (2010).
49. Wang, Y. et al. Systemic delivery of modified mRNA encoding herpes simplex virus 1 thymidine kinase for targeted cancer gene therapy. Mol. Ther. 21, 358-367 (2013).
50. Luo, X. et al. Dual-functional lipid-like nanoparticles for delivery of mRNA and MRI contrast agents. Nanoscale 9, 1575-1579 (2017).
51. Huang, H. et al. PTEN induces chemosensitivity in PTEN-mutated prostate cancer cells by suppression of Bcl-2 expression. J. Biol. Chem. 276, 38830-38836 (2001).
52. Sturge, J., Caley, M. P. & Waxman, J. Bone metastasis in prostate cancer: emerging therapeutic strategies. Nature reviews. Clinical oncology 8, 357-368 (2011).
53. Smukste, I. & Stockwell, B. R. Restoring functions of tumor suppressors with small molecules. Cancer Cell 4, 419-420 (2003).
54. Guo, X. E., Ngo, B., Modrek, A. S. & Lee, W. H. Targeting tumor suppressor networks for cancer therapeutics. Curr. Drug Targets 15, 2-16 (2014).
55. Bettinger, T., Carlisle, R. C., Read, M. L., Ogris, M. & Seymour, L. W. Peptide-mediated RNA delivery: a novel approach for enhanced transfection of primary and postmitotic cells. Nucleic Acids Res. 29, 3882-3891 (2001).
56. Rejman, J., Tavernier, G., Bavarsad, N., Demeester, J. & De Smedt, S. C. mRNA transfection of cervical carcinoma and mesenchymal stem cells mediated by cationic carriers. J. Control. Release 147, 385-391 (2010).
57. Zou, S., Scarfo, K., Nantz, M. H. & Hecker, J. G. Lipid-mediated delivery of RNA is more efficient than delivery of DNA in non-dividing cells. Int. J. Pharm. 389, 232-243 (2010).
58. Read, M. L. et al. A versatile reducible polycation-based system for efficient delivery of a broad range of nucleic acids. Nucleic Acids Res. 33, e86 (2005).
59. Kong, G., Braun, R. D. & Dewhirst, M. W. Hyperthermia enables tumor-specific nanoparticle delivery: effect of particle size. Cancer Res. 60, 4440-4445 (2000).
60. Alexis, F., Pridgen, E., Molnar, L. K. & Farokhzad, O. C. Factors affecting the clearance and biodistribution of polymeric nanoparticles. Mol. Pharm. 5, 505-515 (2008).
61. Shi, J., Kantoff, P. W., Wooster, R. & Farokhzad, O. C. Cancer nanomedicine: progress, challenges and opportunities. Nat. Rev. Cancer 17, 20-37 (2017).
62. Knop, K., Hoogenboom, R., Fischer, D. & Schubert, U.S. Poly(ethylene glycol) in drug delivery: pros and cons as well as potential alternatives. Angew. Chem. Int. Ed. Engl. 49, 6288-6308 (2010).
63. Guo, X. & Huang, L. Recent advances in nonviral vectors for gene delivery. Acc. Chem. Res. 45, 971-979 (2012).
64. Liu, H. et al. Structure-based programming of lymph-node targeting in molecular vaccines. Nature 507, 519-522 (2014).
65. Li, J. et al. PTEN, a putative protein tyrosine phosphatase gene mutated in human brain, breast, and prostate cancer. Science 275, 1943-1947 (1997).
66. Steck, P. A. et al. Identification of a candidate tumour suppressor gene, MMAC1, at chromosome 10q23.3 that is mutated in multiple advanced cancers. Nat. Genet. 15, 356-362 (1997).
67. Di Cristofano, A., De Acetis, M., Koff, A., Cordon-Cardo, C. & Pandolfi, P. P. Pten and p27KIP1 cooperate in prostate cancer tumor suppression in the mouse. Nat. Genet. 27, 222-224 (2001).
68. Hopkins, B. D. et al. A secreted PTEN phosphatase that enters cells to alter signaling and survival. Science 341, 399-402 (2013).
69. Masson, G. R., Perisic, O., Burke, J. E. & Williams, R. L. The intrinsically disordered tails of PTEN and PTEN-L have distinct roles in regulating substrate specificity and membrane activity. Biochem. J. 473, 135-144 (2016).
70. Juric, D. et al. Convergent loss of PTEN leads to clinical resistance to a PI(3)Kalpha inhibitor. Nature 518, 240-244 (2015).
71. Peng, W. et al. Loss of PTEN Promotes Resistance to T Cell-Mediated Immunotherapy. Cancer Discov 6, 202-216 (2016).
72. Campeau, E. et al. A versatile viral system for expression and depletion of proteins in mammalian cells. PloS one 4, e6529 (2009).
73. Ramaswamy, S. et al. Regulation of G1 progression by the PTEN tumor suppressor protein is linked to inhibition of the phosphatidylinositol 3-kinase/Akt pathway. Proc. Natl. Acad. Sci. USA. 96, 2110-2115 (1999).
74. Xu, X. et al. Enhancing tumor cell response to chemotherapy through nanoparticle-mediated codelivery of siRNA and cisplatin prodrug. Proc. Natl. Acad. Sci. USA. 110, 18638-18643 (2013).
75. Cox, T. R. et al. The hypoxic cancer secretome induces pre-metastatic bone lesions through lysyl oxidase. Nature 522, 106-110 (2015).
76. Krzywinski, M. & Altman, N. Points of significance: Nonparametric tests. Nature methods 11, 467-468 (2014).
77. Tammela, T. et al. A Wnt-producing niche drives proliferative potential and progression in lung adenocarcinoma. Nature 545, 355-359 (2017).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a cancer associated with loss of PTEN expression or activity, the method comprising administering to a subject in need thereof a therapeutically effective amount of an mRNA encoding tumor suppressor protein phosphatase and tensin homolog on chromosome ten (PTEN) within a delivery vehicle that provides release of the PTEN-encoding mRNA in the cancer cell in combination with an immunotherapy that comprises administering to the subject at least one immune checkpoint inhibitor.

2. The method of claim 1, wherein the immune checkpoint inhibitor is an anti-PD1 antibody.

3. The method of claim 1, wherein the immune checkpoint inhibitor is an anti-PD-L1 antibody.

4. The method of claim 1, wherein the immune checkpoint inhibitor is an anti-CD137 antibody.

5. The method of claim 1, wherein the immune checkpoint inhibitor is an anti-CTLA-4 antibody.

6. The method of claim 1, wherein the immune checkpoint inhibitor is an anti-CD40 antibody.

7. The method of claim 1, wherein the cancer is selected from prostate cancer, breast cancer, glioblastoma, melanoma, pancreatic cancer, colorectal cancer, and leukemia.

8. The method of claim 1, wherein the delivery vehicle is a particle comprising:
   a water-insoluble polymeric core; and
   the PTEN encoding mRNA and a complexing agent within the core.

9. The method of claim 8, wherein the particle further comprises a shell comprising at least one amphiphilic material surrounding the water-insoluble polymeric core.

10. The method of claim 9, wherein the amphiphilic material is selected from a lecithin, a phospholipid, and a lipid-terminated PEG.

11. The method of claim 10, wherein the phospholipid is selected from phosphatidic acid, phosphatidyl choline, phosphatidyl ethanolamine, phosphatidylglycerol, phosphatidylserine, phosphatidylinositol, lysophosphatidyl, cardiolipin, and β-acyl-y-alkyl phospholipid.

12. The method of claim 10, wherein the lipid-terminated PEG is selected from ceramide-PEG and 2-distearoyl-sn-glycero-3-phosphoethanolamine (DSPE)-terminated PEG.

13. The method of claim 8, wherein the complexing agent is selected from a cationic lipid and a cationic lipid-like compound.

14. The method of claim 13, wherein the cationic lipid is lipofectamine 2000, and the cationic lipid-like compound is G0-C14.

15. The method of claim 8, wherein the water-insoluble polymer is a polyester selected from poly(lactic-co-glycolic acid) (PLGA), poly(lactic acid) (PLA), and poly(glycolic acid) (PGA).

16. The method of claim 8, wherein the water-insoluble polymer is an amphiphilic polymer.

17. The method of claim 16, wherein the amphiphilic polymer is a copolymer of polyethylene glycol (PEG) and a polyester selected from poly(lactic-co-glycolic acid) (PLGA), poly(lactic acid) (PLA), and poly(glycolic acid) (PGA).

* * * * *